US010821435B2

(12) United States Patent
Okada et al.

(10) Patent No.: US 10,821,435 B2
(45) Date of Patent: Nov. 3, 2020

(54) NUCLEIC ACID DETECTION CASSETTE

(71) Applicant: Toshiba Medical Systems Corporation, Otawara-shi (JP)

(72) Inventors: Jun Okada, Tokyo (JP); Masayuki Yumoto, Kawasaki (JP); Kenichi Arame, Fukushima (JP); Tetsuya Kuwabara, Kawasaki (JP); Hiroaki Kushima, Fujisawa (JP); Hirotaka Unno, Tokyo (JP)

(73) Assignee: Canon Medical Systems Corporation, Otawara-shi (JP)

( * ) Notice: Subject to any disclaimer, the term of this patent is extended or adjusted under 35 U.S.C. 154(b) by 130 days.

(21) Appl. No.: 15/448,122

(22) Filed: Mar. 2, 2017

(65) Prior Publication Data
US 2017/0252740 A1     Sep. 7, 2017

Related U.S. Application Data

(63) Continuation of application No. PCT/JP2015/074948, filed on Sep. 2, 2015.

(30) Foreign Application Priority Data

Sep. 2, 2014   (JP) ................. 2014-178420
Sep. 2, 2014   (JP) ................. 2014-178421
(Continued)

(51) Int. Cl.
*B01L 3/00*     (2006.01)
*C12M 1/34*     (2006.01)
(Continued)

(52) U.S. Cl.
CPC ........... *B01L 3/502* (2013.01); *B01L 3/50273* (2013.01); *B01L 7/52* (2013.01); *C12M 1/00* (2013.01);
(Continued)

(58) Field of Classification Search
CPC ............................ B01L 3/5027; B01L 7/52
See application file for complete search history.

(56) References Cited

U.S. PATENT DOCUMENTS

| 5,098,262 A | 3/1992 | Wecker et al. |
| 5,378,126 A | 1/1995 | Abrahamson et al. |
| (Continued) | | |

FOREIGN PATENT DOCUMENTS

| JP | 2001-235468 | 8/2001 |
| JP | 2004-125777 A | 4/2004 |
| (Continued) | | |

OTHER PUBLICATIONS

International Search Report dated Dec. 8, 2015 in PCT/JP2015/074948 filed Sep. 2, 2015 (with English translation).
(Continued)

*Primary Examiner* — William H. Beisner
(74) *Attorney, Agent, or Firm* — Oblon, McClelland, Maier & Neustadt, L.L.P.

(57) ABSTRACT

In a nucleic acid detection cassette, a predetermined syringe is crushed to supply a sample solution to an amplification unit via a channel and the amplification unit is heated from outside to amplify sample DNA in the sample solution. The sample solution containing an amplification product is supplied to a detection unit via the channel and a hybridization reaction occurs in the detection unit. Next, another syringe is crushed and an intercalating agent solution is supplied via another predetermined channel. Therefore, a nucleic acid detection cassette capable of automation from amplification of a sample to detection of an electrochemical reaction of the sample is provided.

7 Claims, 31 Drawing Sheets

Specification includes a Sequence Listing.

(30) Foreign Application Priority Data

| Sep. 2, 2014 | (JP) | ................................. | 2014-178422 |
| Sep. 2, 2014 | (JP) | ................................. | 2014-178423 |
| Sep. 2, 2014 | (JP) | ................................. | 2014-178424 |
| Apr. 30, 2015 | (JP) | ................................. | 2015-093317 |

(51) Int. Cl.
| *B01L 7/00* | (2006.01) |
| *C12Q 1/68* | (2018.01) |
| *C12M 1/00* | (2006.01) |
| *C12N 15/09* | (2006.01) |

(52) U.S. Cl.
CPC ............... *C12M 1/34* (2013.01); *C12N 15/09* (2013.01); *B01L 2200/04* (2013.01); *B01L 2200/0684* (2013.01); *B01L 2200/0689* (2013.01); *B01L 2200/10* (2013.01); *B01L 2200/16* (2013.01); *B01L 2300/0645* (2013.01); *B01L 2300/0816* (2013.01); *B01L 2300/0887* (2013.01); *B01L 2300/123* (2013.01); *B01L 2400/0481* (2013.01); *C12Q 1/68* (2013.01)

(56) References Cited

U.S. PATENT DOCUMENTS

| 2001/0016321 | A1 | 8/2001 | Tanaami |
| 2003/0057391 | A1 | 3/2003 | Krulevitch et al. |
| 2004/0137607 | A1 | 7/2004 | Tanaami et al. |
| 2005/0153430 | A1 | 7/2005 | Ohtaka |
| 2006/0216812 | A1 | 9/2006 | Okada et al. |
| 2009/0042256 | A1 | 2/2009 | Hanafusa et al. |
| 2009/0110605 | A1 | 4/2009 | Kido et al. |
| 2009/0186403 | A1 | 7/2009 | Tanaami et al. |
| 2011/0014606 | A1 | 1/2011 | Steinmetzer et al. |
| 2011/0120580 | A1 | 5/2011 | Takahashi et al. |
| 2014/0148359 | A1 | 5/2014 | Takahashi et al. |
| 2015/0132753 | A1 | 5/2015 | Ye et al. |
| 2015/0197822 | A1 | 7/2015 | Steinmetzer et al. |

FOREIGN PATENT DOCUMENTS

| JP | 2004-212361 | | 7/2004 | |
| JP | 2005-21866 | A | 1/2005 | |
| JP | 2005-176836 | | 7/2005 | |
| JP | 2005-261298 | | 9/2005 | |
| JP | 2005-274405 | | 10/2005 | |
| JP | 2006-503204 | A | 1/2006 | |
| JP | 2006-78500 | | 3/2006 | |
| JP | 2006-149215 | | 6/2006 | |
| JP | 2006-322850 | A | 11/2006 | |
| JP | 2008-49311 | | 3/2008 | |
| JP | 2008-151773 | A | 7/2008 | |
| JP | 2008-224651 | | 9/2008 | |
| JP | 2008-237029 | A | 10/2008 | |
| JP | 2008-241397 | | 10/2008 | |
| JP | 2008-261816 | | 10/2008 | |
| JP | 2008-263959 | A | 11/2008 | |
| JP | 2009-82834 | A | 4/2009 | |
| JP | 2009-109334 | | 5/2009 | |
| JP | 2009-119387 | A | 6/2009 | |
| JP | 2009-526969 | A | 7/2009 | |
| JP | 2010-68783 | A | 4/2010 | |
| JP | 2010-75072 | | 4/2010 | |
| JP | 2012-147751 | A | 8/2012 | |
| JP | 2013-51958 | | 3/2013 | |
| JP | 2013-66463 | | 4/2013 | |
| JP | 2013-116125 | A | 6/2013 | |
| JP | 2013-521780 | | 6/2013 | |
| JP | 2013-145217 | | 7/2013 | |
| JP | 2013-192521 | | 9/2013 | |
| JP | 2013-198443 | | 10/2013 | |
| JP | 2014-60925 | | 4/2014 | |
| JP | 2014-62870 | | 4/2014 | |
| JP | 2015-199028 | A | 11/2015 | |
| JP | 6400392 | B2 | 10/2018 | |
| WO | WO 97/27324 | A1 | 7/1997 | |
| WO | WO 2008/055915 | A2 | 5/2008 | |
| WO | WO 2008/055915 | A3 | 5/2008 | |
| WO | WO 2008/087828 | A1 | 7/2008 | |
| WO | WO 2008/096570 | A1 | 8/2008 | |
| WO | WO 2008/108027 | A1 | 9/2008 | |
| WO | WO 2010/050208 | A1 | 5/2010 | |
| WO | WO-2013021958 | A1 * | 2/2013 | ........ B01L 3/502761 |
| WO | WO 2013/166857 | A1 | 11/2013 | |

OTHER PUBLICATIONS

Written Opinion dated Dec. 8, 2015 in PCT/JP2015/074948 filed Sep. 2, 2015.
Masayoshi Takahashi, "Denryu Kenshutsugata DNA Chip o Mochiita Shokuchudoku Gen'inkin no Kan'l Jido Kensa Gijutsu no Kaihatsu", Japanese Society of Food Microbiology Gakujutsu Sokai Koen Yoshishu, 2012, vol. 33, 3 pgs.
Extended Search Report dated Feb. 21, 2018 in European Patent Application No. 15838168.1.
Japanese Office Action dated Jan. 8, 2019 in Patent Application No. 2014-178424 (with English translation), 23 pages.
Office Action dated May 22, 2018 in Japanese Patent Application No. 2014-178421 (with English language translation), 18 pages.
Office Action dated Dec. 25, 2018 in Japanese Patent Application No. 2014-178421, 9 pages (with English translation).
Office Action dated May 29, 2018 in Japanese Patent Application No. 2014-178422, with English translation, 15 pages.
Office Action dated May 29, 2018 in Japanese Patent Application No. 2014-178423, with English translation, 12 pages.
Dafeng Chen et al., "An integrated, self-contained microfluidic cassette for isolation, amplification, and detection of nucleic acids", Departmental Papers (MEAM), 2010, 271 (pp. 1-21), downloaded by the JPO on May 18, 2018 from: https://repository.upenn.edu/meam_papers/271[Postprint Version: Dafeng Chen et al., "An integrated, self-contained microfluidic cassette for isolation, amplification, and detection of nucleic acids", Biomedical Microdevices (vol. 14, No. 4) Aug. 2010, pp. 705-719.
Patrick M. Pilarski et al., "An adaptable microvalving system for on-chip polymerase chain reactions", Journal of Immunological Methods (vol. 305) Aug. 22, 2005, pp. 48-58.
Office Action dated May 7, 2019 in Japanese Patent Application No. 2015-093317 (with English translation), 32 pages.
Liu, C. et al., "A disposable, integrated loop-mediated isothermal amplification cassette with thermally actuated valves", Microfluid and Nanofluid, vol. 11, Mar. 18, 2011, pp. 209-220.
Watanabe, H. et al., "Development of "i-chip" for Microchip Electrophoresis System", Hitachi Chemical Technical Report, No. 40, Jan. 2003, pp. 29-32 (with English Abstract).
Zanoli, L. M. et al. "Isothermal Amplification Methods for the Detection of Nucleic Acids in Microfluidic Devices", Biosensors, vol. 3, Dec. 27, 2012, pp. 18-43.
Nakamura, N. et al., "Detection of Six Single-Nucleotide Polymorphisms Associated with Rheumatoid Arthritis by a Loop-Mediated Isothermal Amplification Method and an Electrochemical DNA Chip", Analytical Chemistry, vol. 79, No. 24, Nov. 7, 2007, pp. 9484-9493.
Nakamura, N. et al., "Simple and accurate determination of CYP2D6 gene copy number by a loop-mediated isothermal amplification method and an electrochemical DNA chip", Clinica Chimica Acta, vol. 411, Jan. 20, 2010, pp. 568-573.
Sun, Y. et al., "Pre-storage of gelified reagents in a lab-on-a-foil system for rapid nucleic acid analysis", Lab on a Chip, vol. 13, Jan. 7, 2013, pp. 1509-1514.
Japanese Office Action dated Sep. 3, 2019 in Japanese Patent Application No. 2014-178422 (with English translation), 11 pages.
Izuru Shinmura (Ed.), "Kojien", 5th edition, 1998, p. 337.
Combined Office Action and Search Report dated Mar. 29, 2019 in Chinese Patent Application No. 201580047234.4 (with English translation), 20 pages.

(56) References Cited

OTHER PUBLICATIONS

Izuru Shinmura (Ed.), "Kojien", 5th Edition, 1998, pp. 563, 1672 & 2519.
Japanese Office Action dated Feb. 18, 2020, in corresponding Japanese Patent Application No. 2015-093317 filed Apr. 30, 2015 (with English translation).

* cited by examiner

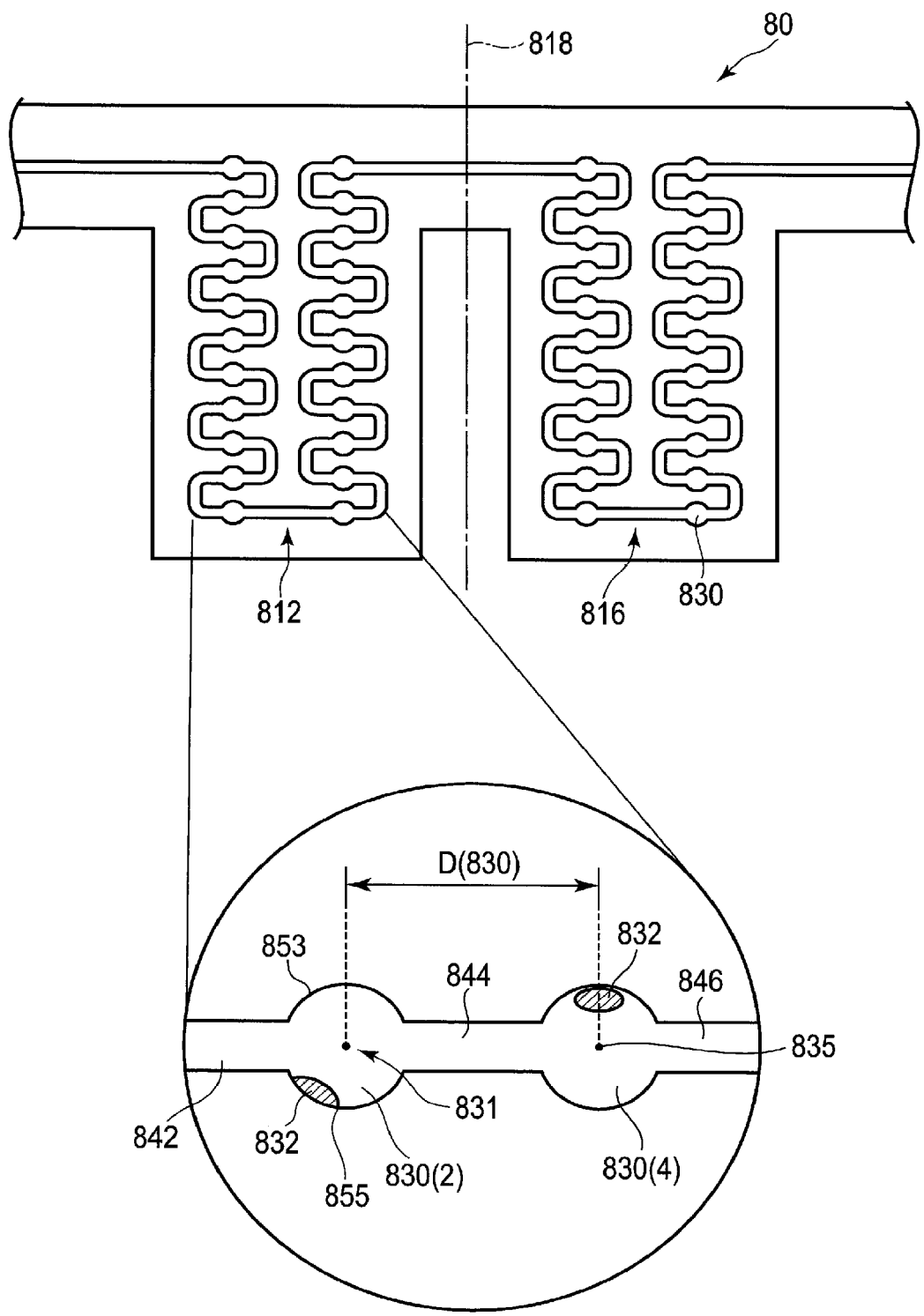
F I G. 7

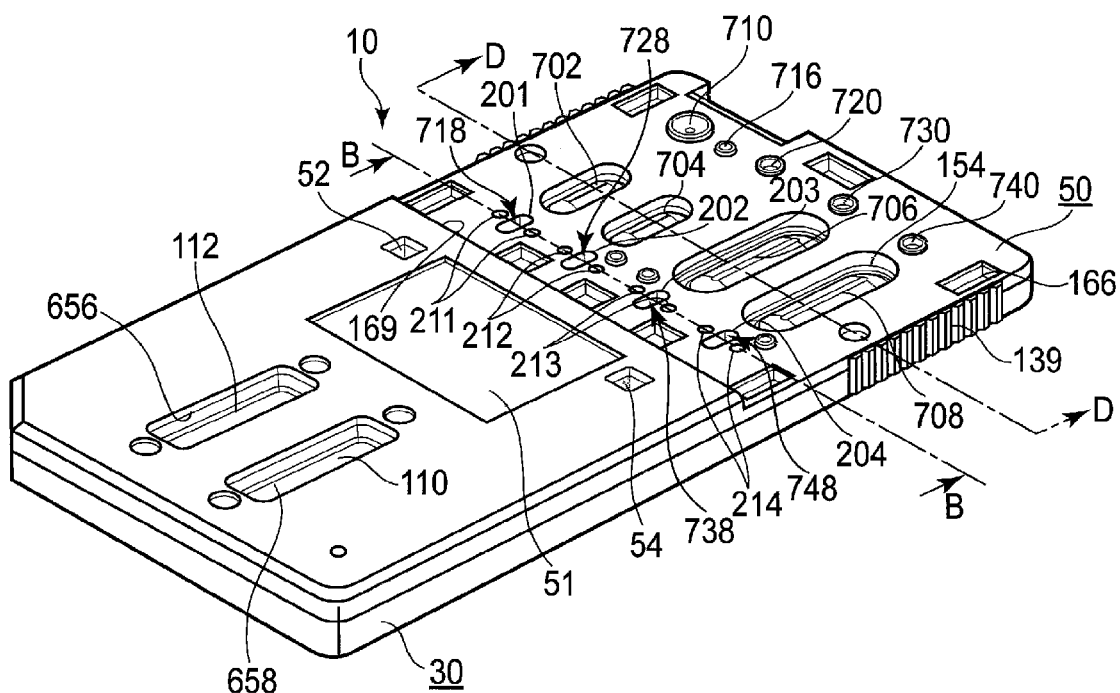
F I G. 9
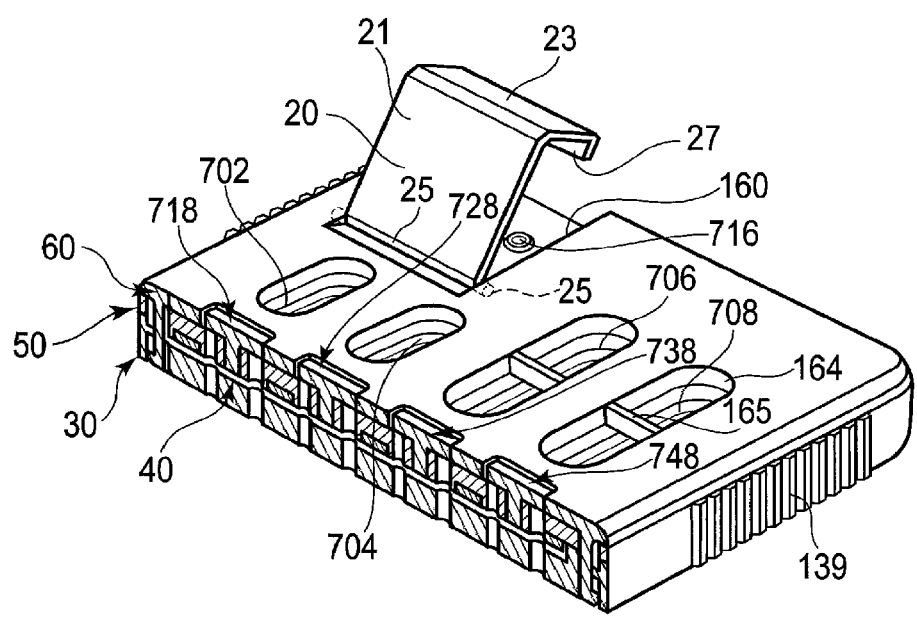
F I G. 10

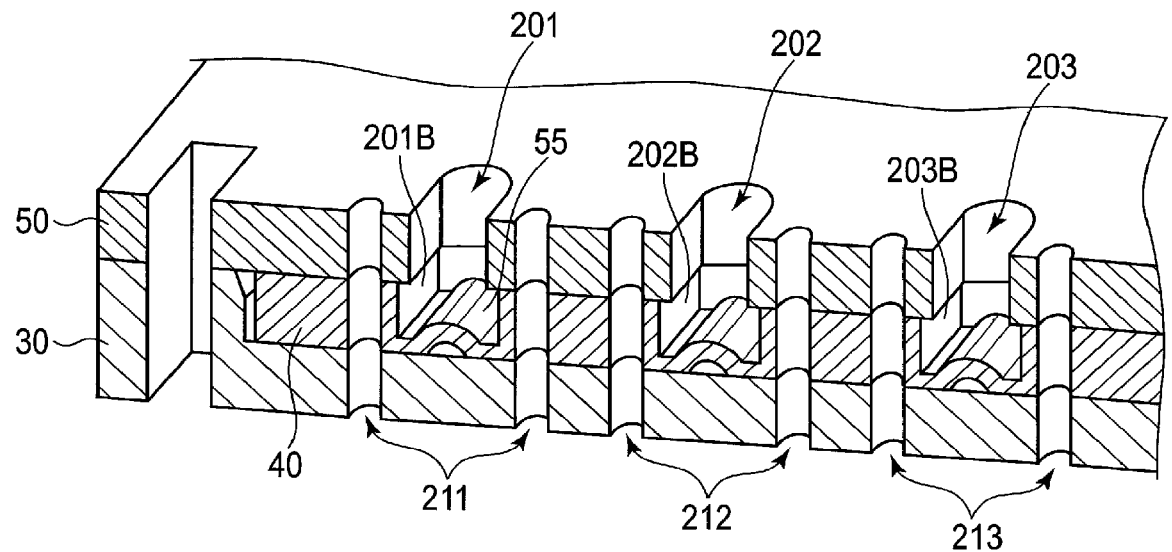
F I G. 15
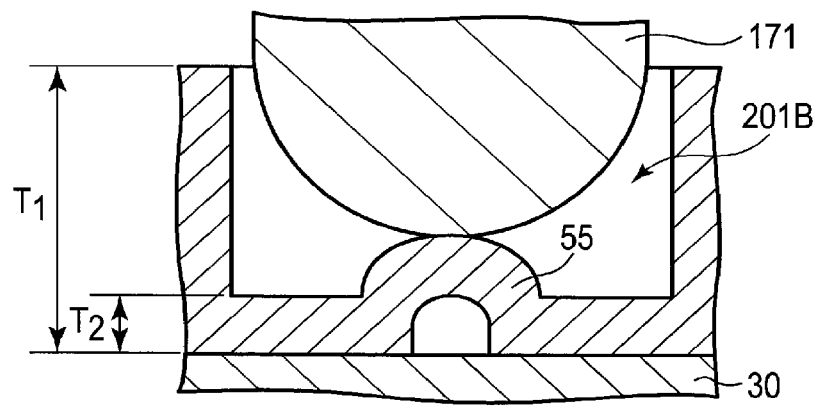
F I G. 16

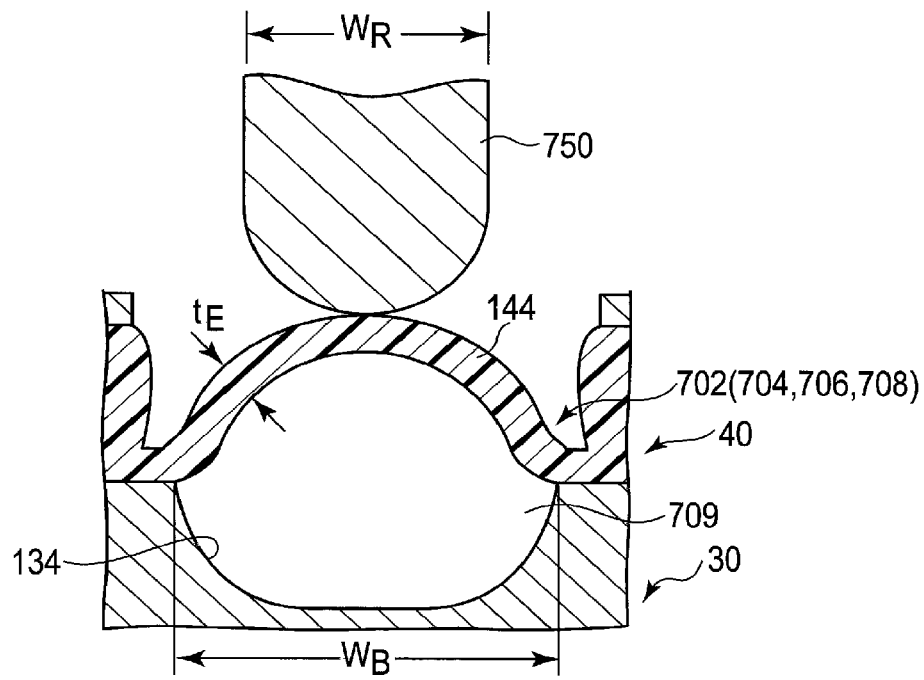
F I G. 19
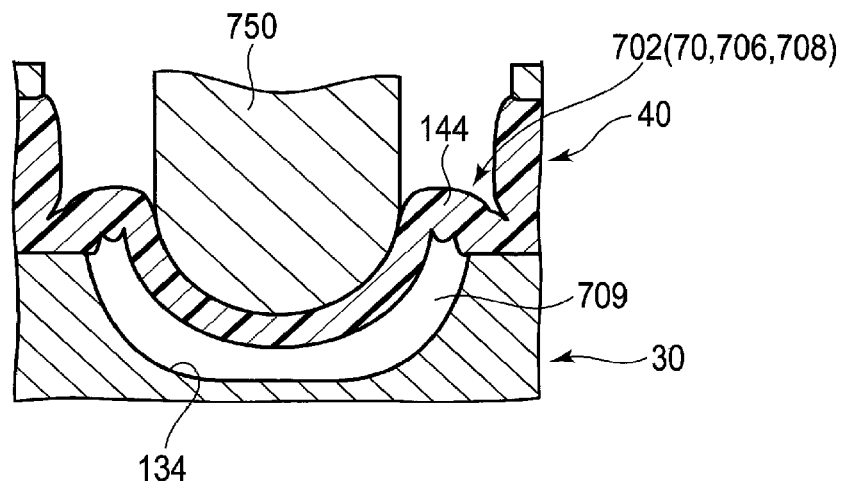
F I G. 20

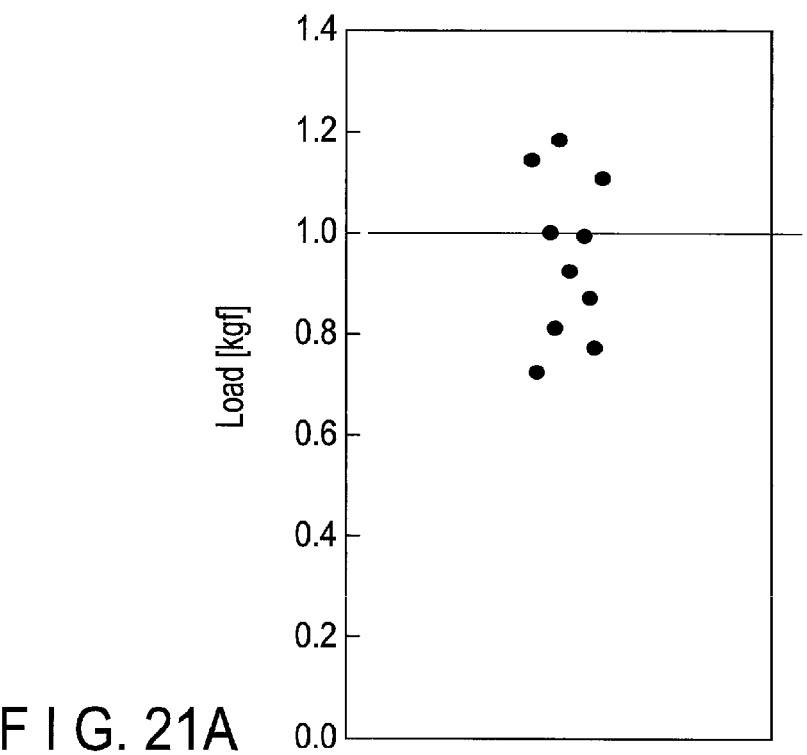
F I G. 21A
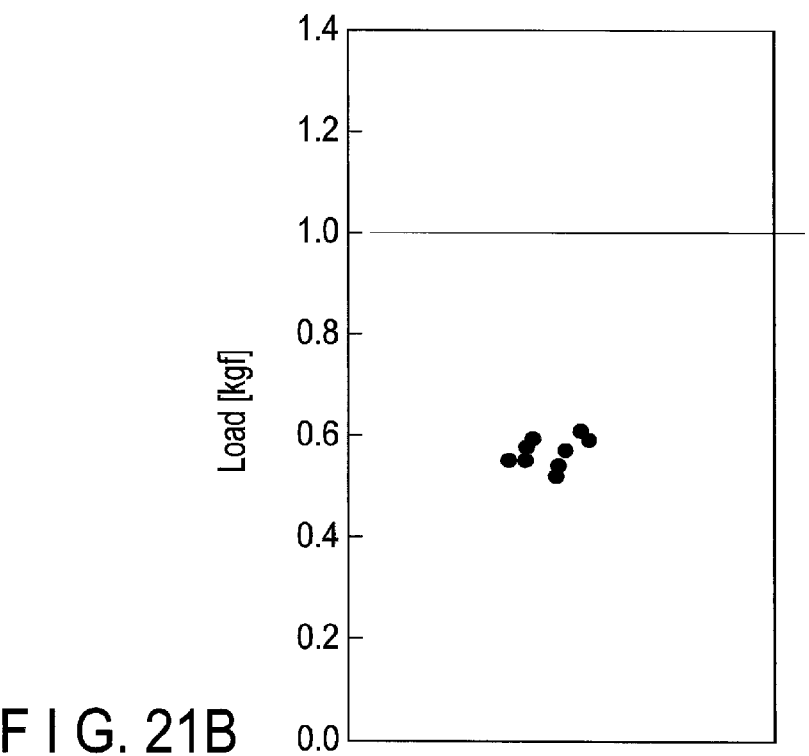
F I G. 21B

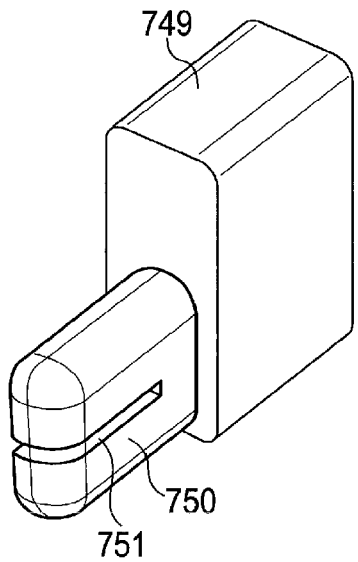
F I G. 22
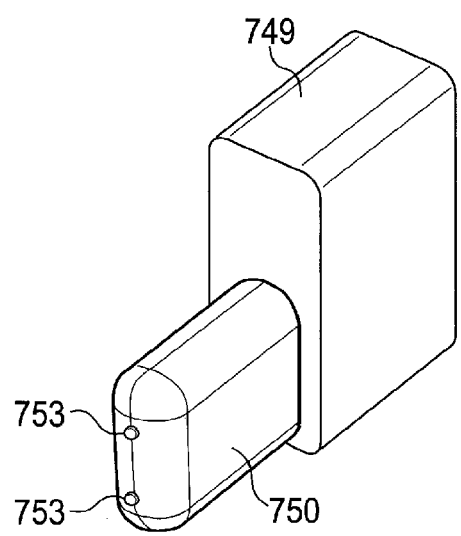
F I G. 23

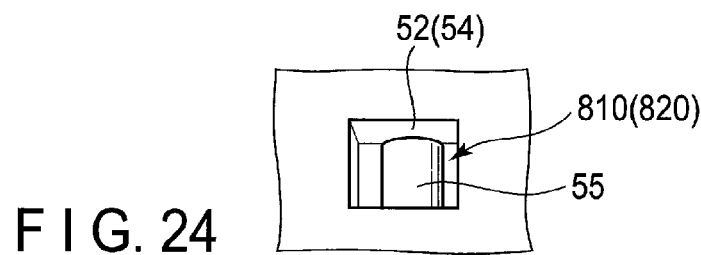
F I G. 24
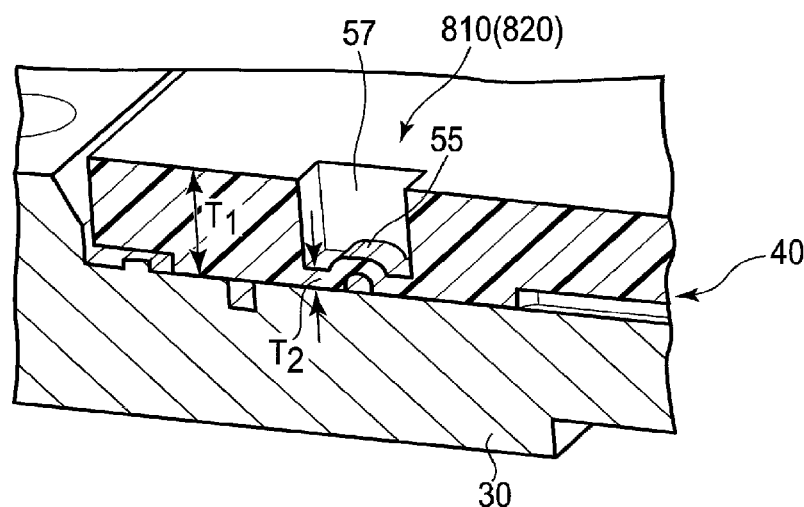
F I G. 25
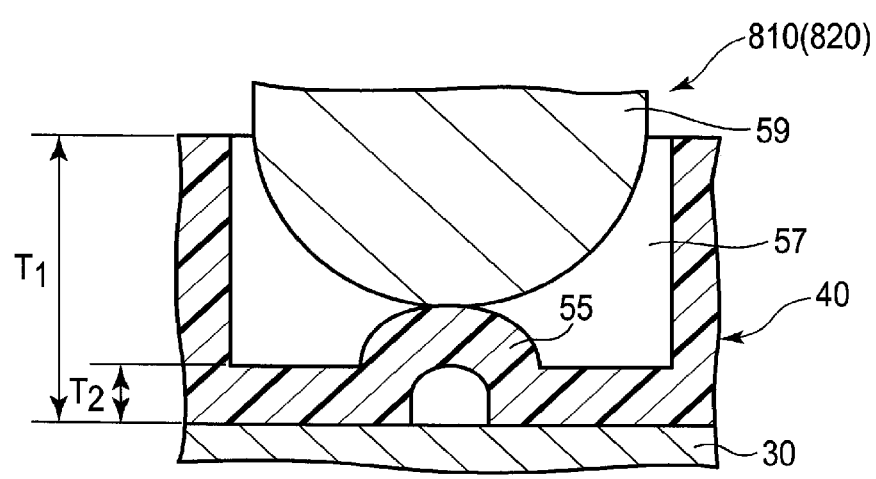
F I G. 26

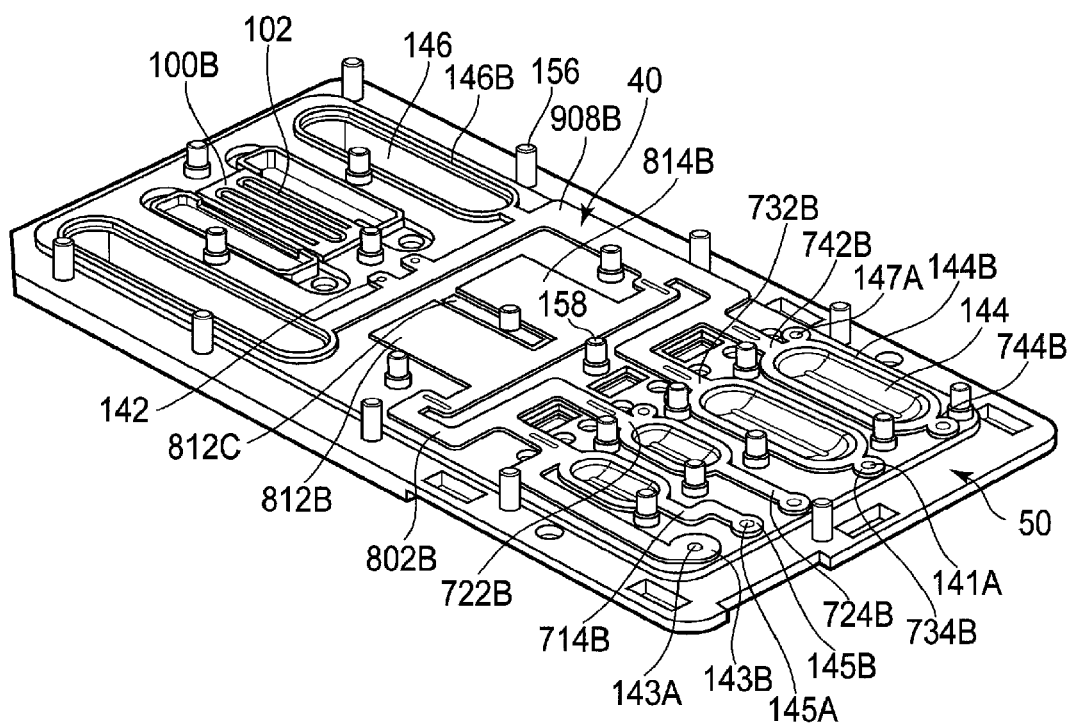
F I G. 32

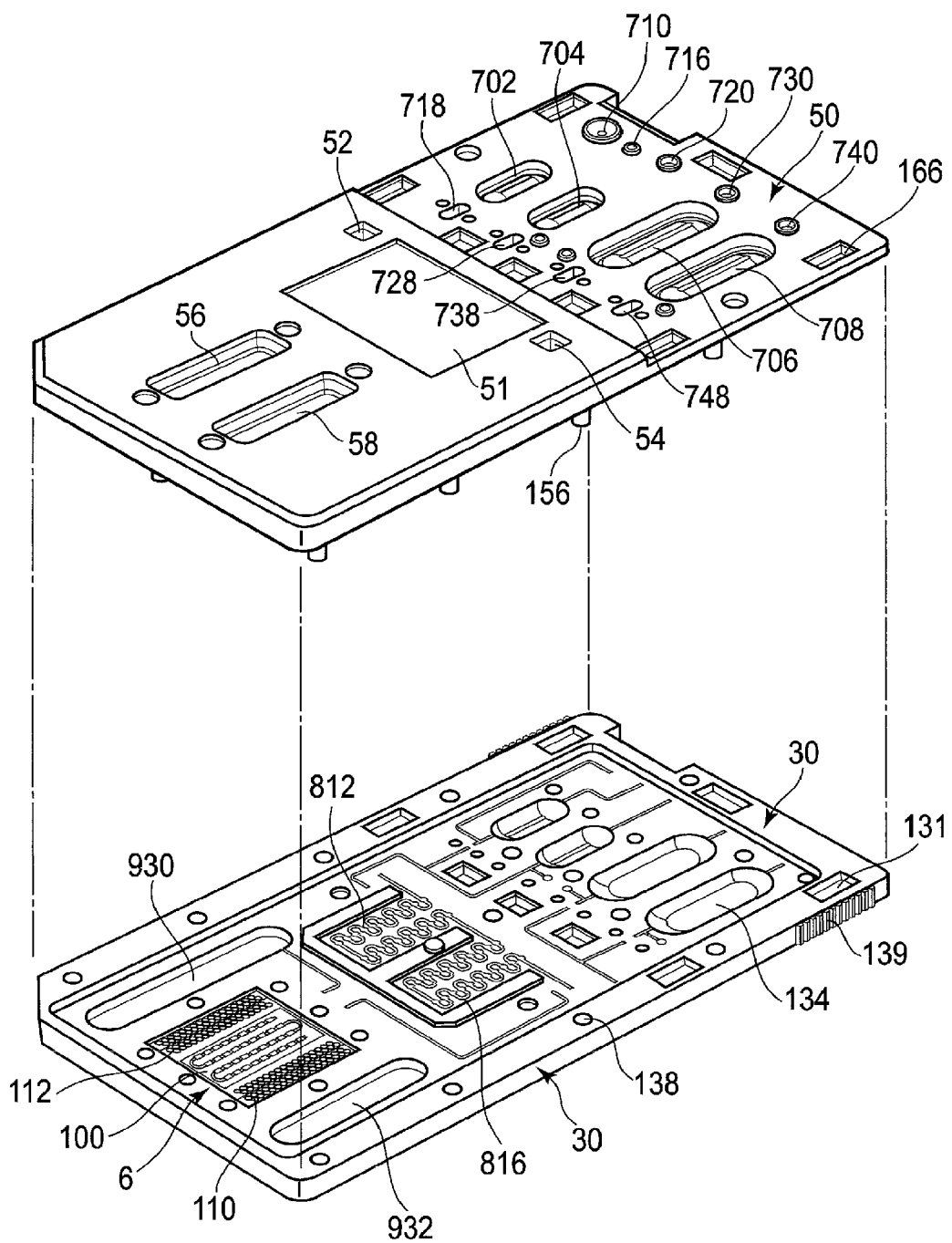
F I G. 33

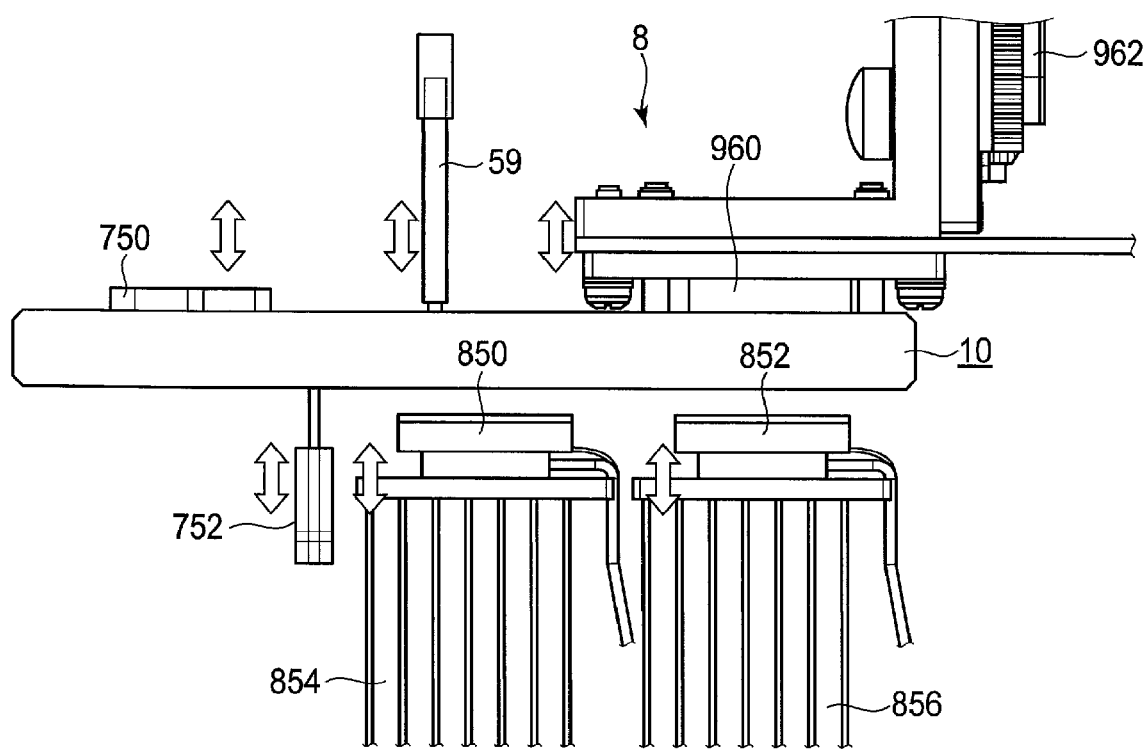
F I G. 34

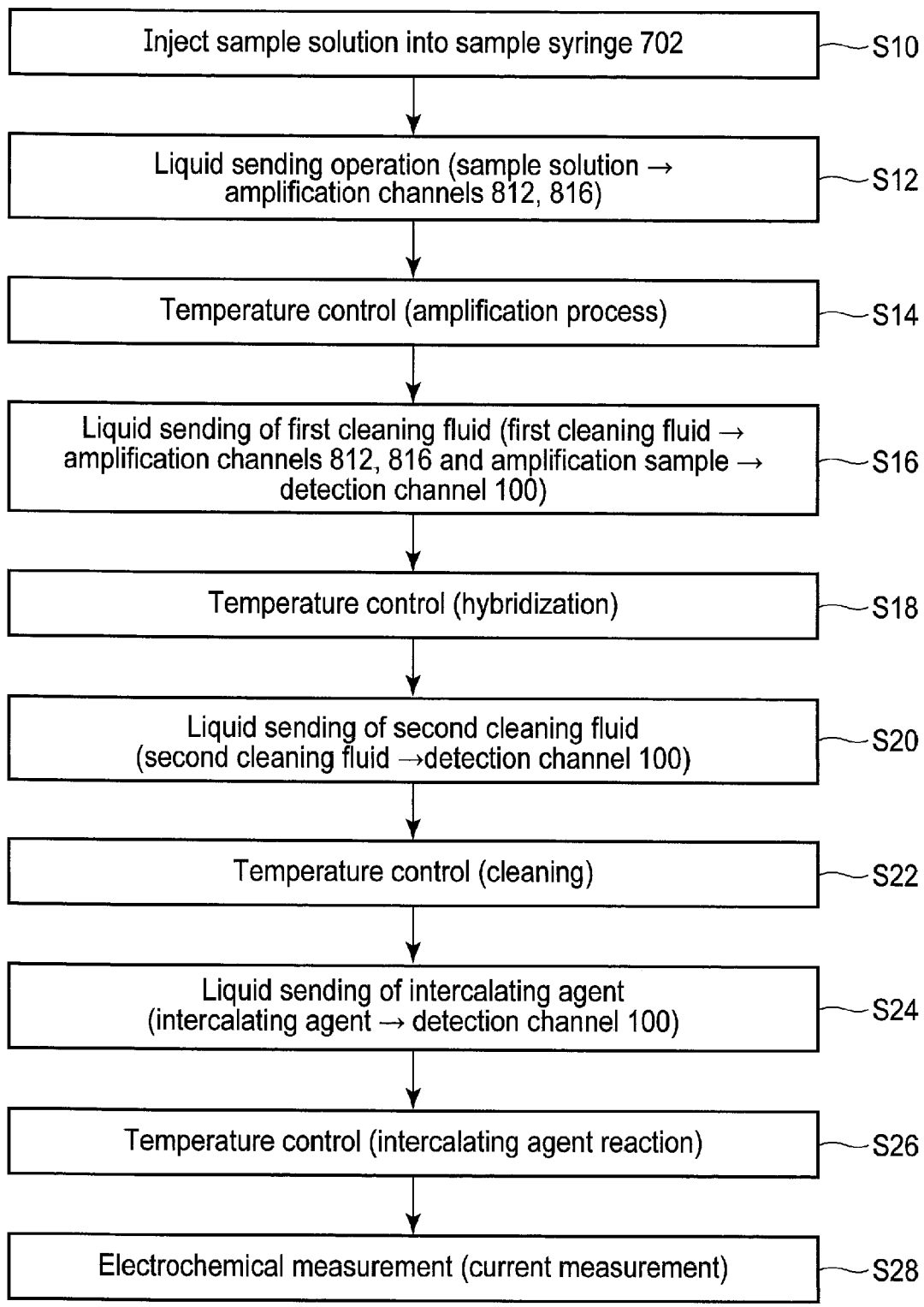
F I G. 35

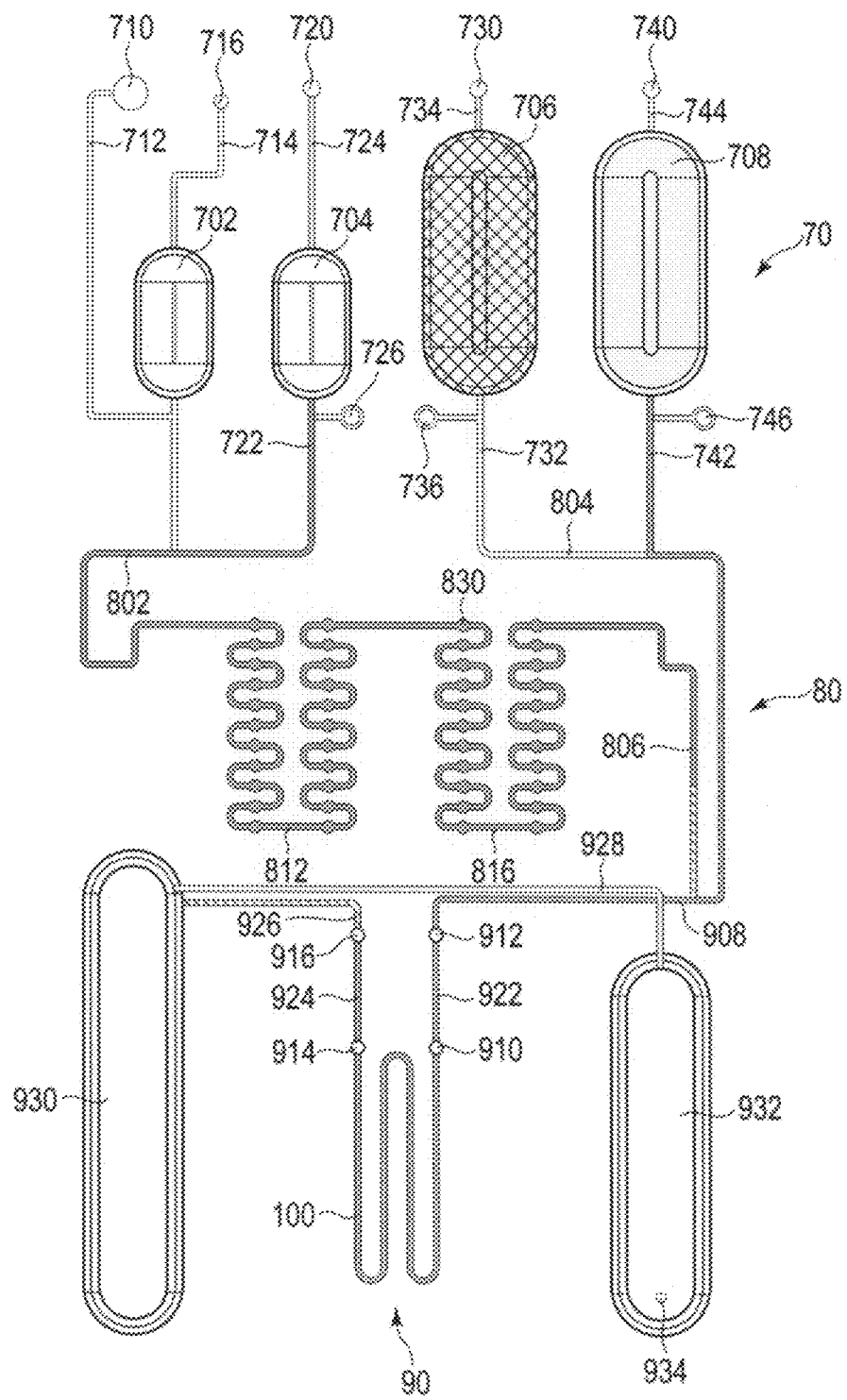
F I G. 38

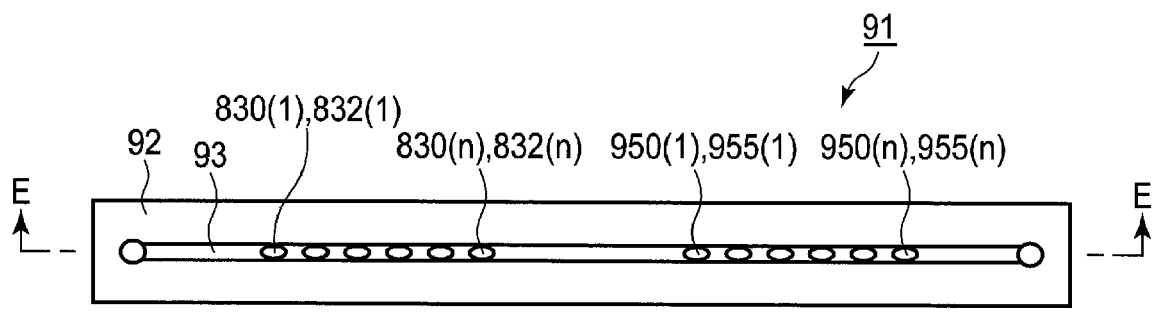
F I G. 40A
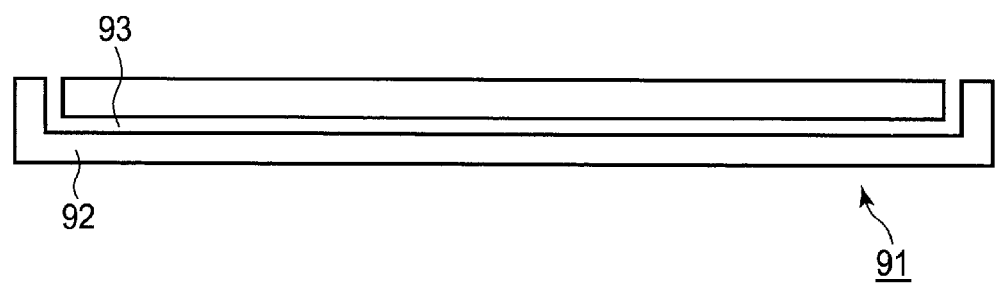
F I G. 40B

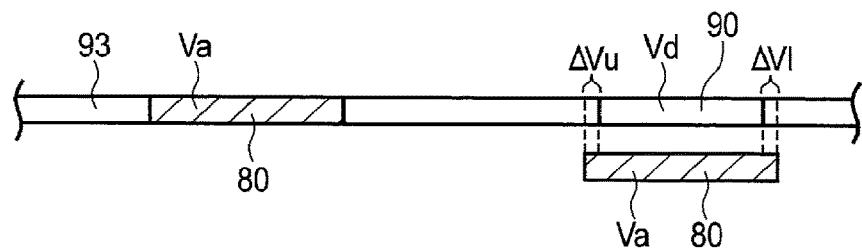
F I G. 41A
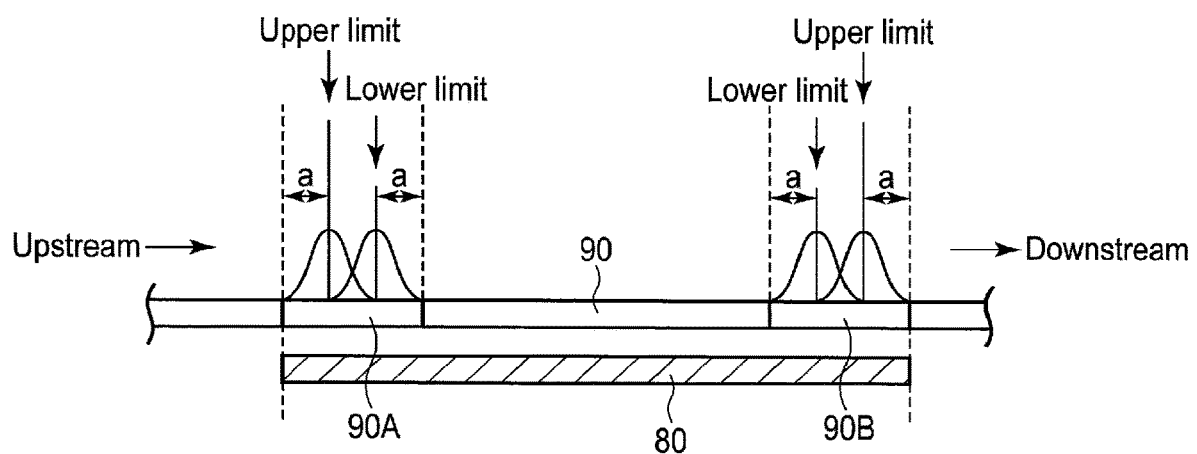
F I G. 41B

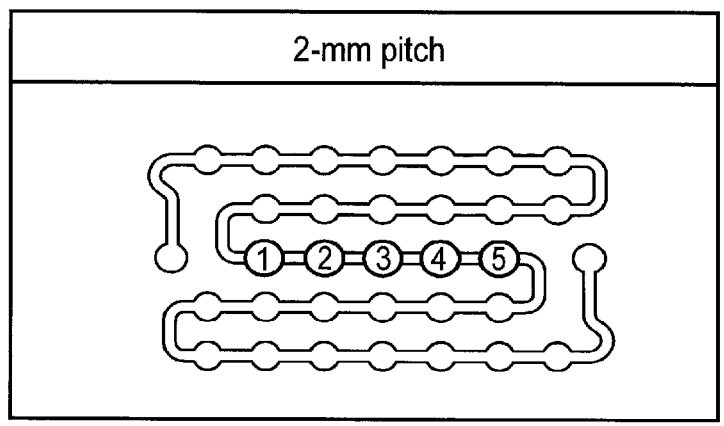
F I G. 42A
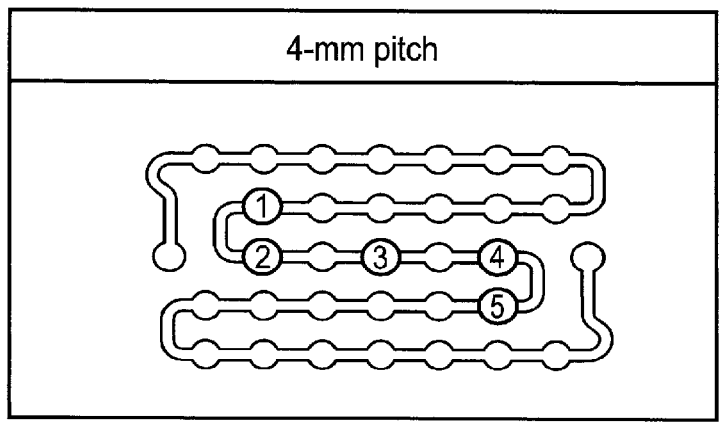
F I G. 42B
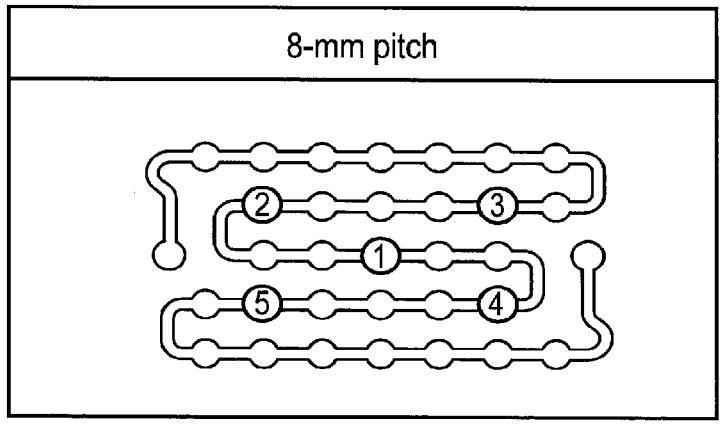
F I G. 42C

US 10,821,435 B2

NUCLEIC ACID DETECTION CASSETTE

CROSS REFERENCE TO RELATED APPLICATIONS

This application is a Continuation Application of PCT Application No. PCT/JP2015/074948, filed Sep. 2, 2015 and based upon and claiming the benefit of priority from Japanese Patent Applications No. 2014-178420, filed Sep. 2, 2014; and No. 2014-178421, filed Sep. 2, 2014; and No. 2014-178422, filed Sep. 2, 2014; and No. 2014-178423, filed Sep. 2, 2014; and No. 2014-178424, filed Sep. 2, 2014; and No. 2015-093317, filed Apr. 30, 2015, the entire contents of all of which are incorporated herein by reference.

FIELD

Embodiments described herein relate generally to a nucleic acid detection cassette used by a nucleic acid testing device, that detects nucleic acid by using an electric signal.

BACKGROUND

With the development of genetic engineering in recent years, it becomes increasingly possible to diagnose or prevent diseases in the medical field based on genes. This is called gene diagnosis and according to the gene diagnosis, a disease can be diagnosed or predicted before the disease appears or in an extremely early stage of the disease by detecting a gene defect or gene alteration of humans that can cause the disease. Also, research on the relationship between the genotype and diseases is going on along with decoding of the human genome, leading to implementation of treatment adapted to the genotype of each individual (tailor-made medicine). Therefore, it is very important to detect genes and determine the genotype handily.

A device using a DNA chip is known as a nucleic acid testing device. The DNA chip includes a detection area on which a nucleic acid probe is immobilized and made of a plurality of sensor units on a substrate and is characterized in that many nucleotide sequences can be detected at a time. In general, a nucleic acid probe is immobilized on a sensor surface by being dripped onto each sensor unit in a state dissolved in a liquid. Because mutually different nucleic acid probes are immobilized for each sensor unit, contact of droplets between sensor units is to be avoided.

On the other hand, a device capable of sequentially causing a plurality of reactions in which a plurality of reagents is involved in one device and called μ-TAS is actively researched and developed. μ-TAS is provided with a reagent holding area, a reaction area and a detection area of nucleic acid and the like and includes a channel connecting the areas.

Further, a nucleic acid testing device to detect nucleic acid by using a nucleic acid detection cassette containing a DNA chip of the current detection method has been developed. When nucleic acid is detected inside such a device, it is necessary to use a plurality of reagents and to cause a plurality of processes and reactions, for example, extraction, purification, a nucleic acid amplification reaction, a nucleic acid hybridization reaction and the like under predetermined conditions. Such reagents are generally expensive and so it is desirable to reduce the amount of use as much as possible and to obtain much information from such a small amount of sample solutions.

To achieve lower prices of nucleic acid detection cassettes, as described above, nucleic acid detection cassettes are required to have high sealing properties and also to be reduced in size. A sample solution needs to be injected by the user and so the structure of a sample injection port needs to be handy. For a sealed sample chamber in which air bubbles must not be mixed during liquid sending, the nucleic acid detection cassette needs to be internally fluid-tight and air bubbles and the like need to be prevented from mixing into a liquid sending channel from the sample injection port. Also, the sample injection port and a syringe that stores the sample solution need to be structured to cause no problem when the amount of the sample solution to be input varies slightly. On the other hand, reagents are expensive and are required to be able to input by minimizing waste. Further, to prevent environmental pollution by samples, the vicinity of the sample injection port must have an untouchable structure after the sample solution is input. In addition, the number of man-hours and the number of components are desirably smaller to achieve lower costs.

BRIEF DESCRIPTION OF THE DRAWINGS

FIG. 7 is a plan view schematically showing the shape of an amplification unit of the nucleic acid detection cassette shown in FIG. 2.

FIG. 9 is a perspective view schematically showing the appearance when a cap and a cover are removed from the nucleic acid detection cassette shown in FIG. 2.

FIG. 10 is a partial section perspective view schematically showing a cross section obtained by cutting the nucleic acid detection cassette shown in FIG. 2 along an A-A line.

FIG. 15 is a partial section perspective view of the nucleic acid detection cassette along B-B line in FIG. 9.

FIG. 16 is a partial section perspective view schematically showing the structure of a normally closed valve shown in FIG. 15, the structure of the normally closed valve being in a normally open state communicatively connected to a syringe.

FIG. 19 is a partial sectional view schematically showing the arrangement of a syringe of the nucleic acid detection cassette shown in FIG. 18 and a syringe rod that presses the syringe.

FIG. 20 is a partial sectional view schematically showing a state of deformation by pressing the syringe rod into a swelling portion of the syringe shown in FIG. 18.

FIG. 21A is a diagram showing a load distribution when the syringe rod is pressed into the swelling portion of a syringe according to Comparative Example 10 times.

FIG. 21B is a diagram showing a load distribution when the syringe rod is pressed into the swelling portion of the syringe shown in FIG. 18 10 times.

FIG. 22 is a perspective view showing the shape of the syringe rod pressed into the swelling portion of an intercalating agent syringe and a second cleaning fluid syringe shown in FIG. 18.

FIG. 23 is a perspective view showing another shape of the syringe rod pressed into the swelling portion of the intercalating agent syringe and the second cleaning fluid syringe shown in FIG. 18.

FIG. 24 is a plan view schematically showing an outside structure of a normally open valve provided in inflow and outflow portions of the amplification unit shown in FIG. 4.

FIG. 25 is a partial sectional view schematically showing the shape of the normally open valve shown in FIG. 24.

FIG. 26 is a partial sectional view schematically showing the normally open valve shown in FIG. 25 and opened and a portion of a valve rod that performs a closing operation of the normally open valve.

FIG. 32 is a perspective view schematically showing the structure in which the packing is mounted on the back face of the upper plate shown in FIG. 31.

FIG. 33 is a perspective view schematically showing a process in which the upper plate on which the packing shown in FIG. 32 is mounted is mounted on the lower plate.

FIG. 34 is a side view schematically showing the internal structure of the nucleic acid testing device shown in FIG. 1.

FIG. 35 is a flowchart showing a process of electrochemical inspection of a sample in the nucleic acid testing device in FIG. 1.

FIG. 38 is a plan view schematically showing the supply of a second cleaning fluid to the detection unit inside the nucleic acid detection cassette shown in FIG. 4.

FIG. 40A is a plan view schematically showing a channel model from the amplification unit to the detection unit of a nucleic acid detector according to an embodiment.

FIG. 40B is a cross section obtained by cutting the channel model of the nucleic acid detector shown in FIG. 40A along a line E-E.

FIG. 41A is a schematic diagram conceptually showing the relationship between the volume of the amplification unit and the volume of the detection unit in the channel model shown in FIG. 40A.

FIG. 41B is a schematic diagram showing the relationship between an area outside the detection unit on a channel extending upstream of the detection unit and an area outside the detection unit on a channel extending downstream of the detection unit 90 in the channel model shown in FIG. 40A as a conceptual diagram.

FIG. 42A is a graph showing an experimental result.
FIG. 42B is a graph showing an experimental result.
FIG. 42C is a graph showing an experimental result.

DETAILED DESCRIPTION

Hereinafter, a nucleic acid detection cassette according to an embodiment will be described in detail with reference to the drawings.

According to an embodiment, there is provided a nucleic acid detection cassette comprising:

a plurality of syringes deformable from outside including first, second, and third syringes to store a sample solution, an intercalating agent solution, and a first cleaning fluid;

an amplification unit that generates an amplification product by amplifying DNA in the sample solution;

a detection unit connected to the amplification unit so that the amplification product is supplied from the amplification unit to electrically detect a hybridization reaction caused in the amplification product supplied; and a waste liquid storage portion that receives a waste liquid containing an unreacted sample and the first cleaning fluid inside the detection unit from the detection unit, wherein the first syringe in which the sample solution is stored is connected to the detection unit via the amplification unit, the second syringe in which the intercalating agent solution is stored and the third syringe in which the first cleaning fluid is stored are connected to the detection unit, and the detection unit is connected to the waste liquid storage portion.

(Outline Configuration of a Nucleic Acid Testing Device)

Figure 1:
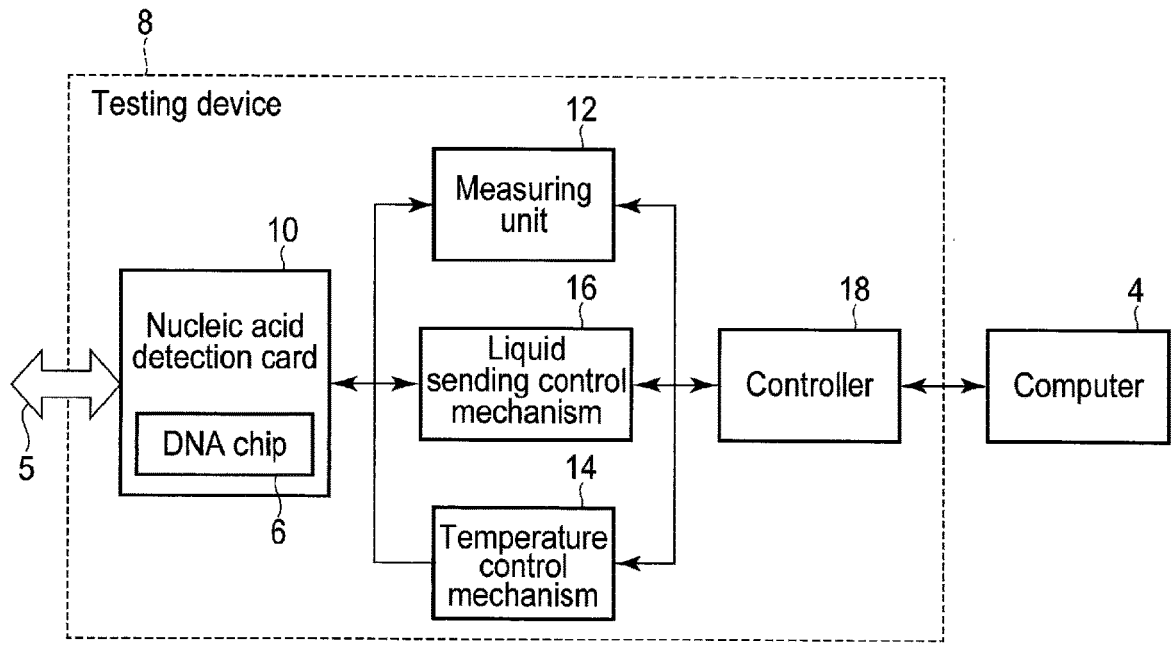
FIG. 1 is a block diagram schematically showing a nucleic acid testing device according to an embodiment.

FIG. 1 shows a block of a nucleic acid testing device 8 according to an embodiment. The nucleic acid testing device 8 is configured to be able to achieve complete automation from amplification of a sample to detection of an electrochemical reaction of a sample. The nucleic acid testing device 8 includes a nucleic acid detection cassette 10 sealed fluid-tightly and a measuring unit 12 electrically connected to the nucleic acid detection cassette 10. The nucleic acid testing device 8 also includes a liquid sending control mechanism 16 that physically drives and controls a channel system provided inside the nucleic acid detection cassette 10 from outside and a temperature control mechanism 14 that controls the temperature of each portion of the nucleic acid detection cassette 10. As will be described in detail below, the nucleic acid detection cassette 10 has a DNA chip 6 stored therein. A detection channel through which a solution such as a sample solution flows is provided on the DNA chip 6. A plurality of electrodes to fetch a hybridize signal is arranged in the detection channel on the DNA chip 6. Also in the detection channel on the DNA chip 6, as will be described in detail below, a working electrode having a nucleic acid probe for detection to detect, for example, SNP (1) to SNP (N) (Single Nucleotide Polymorphism) fixed to the electrode is arranged at regular intervals. Also in the detection channel, at least a counter electrode and a reference electrode are provided in an arrangement opposed to these working electrodes.

The measuring unit 12 shown in FIG. 1 is connected to the DNA chip 6 to constitute a 3-electrode potentiostat that gives feedback (negative feedback) of the voltage of the reference electrode in accordance with the application of an input voltage between the working electrode and the counter electrode inside the DNA chip 6. Thus, the measuring unit 12 can apply a desired voltage into a solution regardless of variations of various conditions of the electrode inside cells in the nucleic acid detection cassette 10, the solution and the like so that a current generated by an electrochemical reaction (hereinafter, called an "electrochemical current") can electrochemically be measured.

The measuring unit 12 described above, the temperature control mechanism 14, and the liquid sending control mechanism 16 are connected to a device controller 18 and the device controller 18 is connected to a computer 4 outside the nucleic acid testing device 8 via an interface (not shown). In response to a command such as an operation instruction from the computer 4, the device controller 18 controls the measuring unit 12, the temperature control mechanism 14, and the liquid sending control mechanism 16 according to a built-in program. The device controller 18 controls and causes the liquid sending control mechanism 16 to send a solution such as a sample solution. Also, the device controller 18 controls and causes the temperature control mechanism 14 to control the temperature of a sample solution to generate an amplification reaction of nucleic acid, a hybridize reaction, and an electrochemical reaction. Further, the device controller 18 controls the measuring unit 12 to detect an electrochemical reaction subsequent to a hybridize reaction and transfers an obtained detection signal to the computer 4 outside as detection data. The computer 4 analyzes the transferred detection data to identify the presence of nucleic acid in the sample solution. The nucleic acid testing device 8 shown in FIG. 1 achieves automation from amplification of nucleic acid in a sample solution to detection of an electrochemical reaction so that data on base sequence of nucleic acid contained in a sample solution can be acquired only by inserting the nucleic acid detection cassette 10 in which the sample solution is accommodated into the nucleic acid testing device 8.

(Basic Structure of the Nucleic Acid Detection Cassette)

Figure 2:
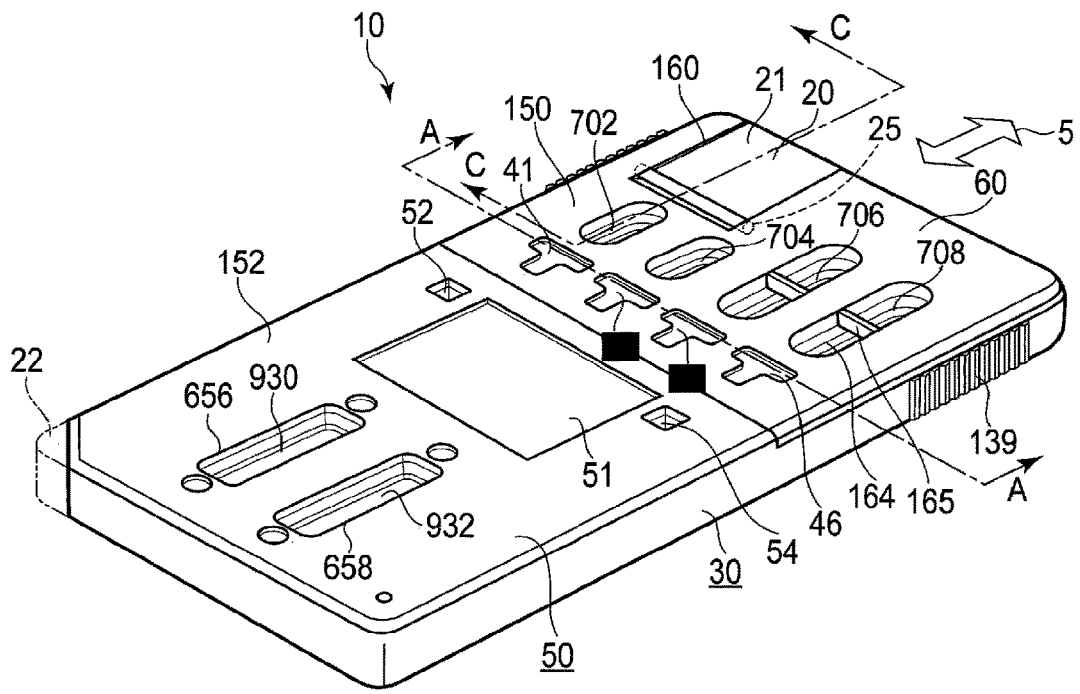
FIG. 2 is a perspective view schematically showing the appearance of a nucleic acid detection cassette inserted into the nucleic acid testing device shown in FIG. 1.

As shown in FIG. 2, the nucleic acid detection cassette 10 is inserted into the nucleic acid testing device 8 in a direction indicated by an arrow 5 and has the appearance in a shape of a removed rectangular cassette. Here, the nucleic acid detection cassette 10 is provided with a notched portion 22 in a portion (corner) thereof to determine the orientation when inserted into the nucleic acid testing device 8. In an embodiment shown in FIG. 2, the notched portion 22 is provided by notching a front right-side corner in an insertion direction of the nucleic acid detection cassette 10 in a rectangular shape relative to an insertion (mounting) direction 5 into the device. The user (operator) can correctly insert the nucleic acid detection cassette 10 into the nucleic acid testing device 8 by making sure that the notched portion 22 is on the tip side.

Incidentally, an embodiment is not limited to a form in which a corner of the nucleic acid detection cassette 10 is notched and the top surface of the nucleic acid detection cassette 10 may be identified by another location being notched so that the insertion direction of the nucleic acid detection cassette 10 is identified. In the description that follows, the notched portion 22 of the nucleic acid detection cassette 10 is defined as the front side and the front side is defined as the reference of insertion direction. The side opposite to the front side is called a back side and the surface of the nucleic acid detection cassette 10 on which a cap (cover) 20 is openably/closably mounted is called a top surface.

Figure 3:
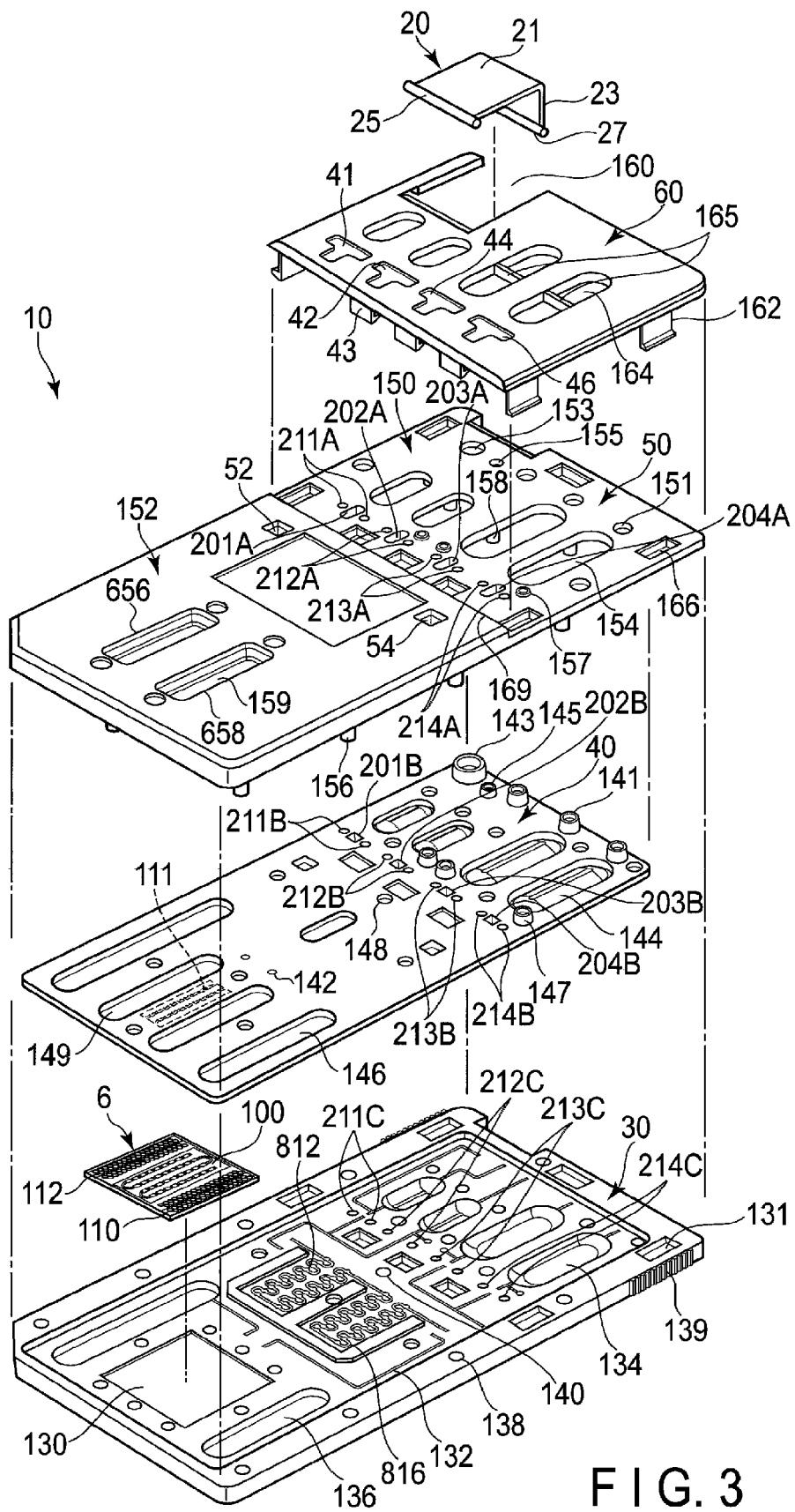
FIG. 3 is an exploded perspective view schematically showing the nucleic acid detection cassette shown in FIG. 2 by exploding the cassette.

The nucleic acid detection cassette 10 includes, as exploded and shown in FIG. 3, a lower plate (first plate) 30, packing 40, an upper plate (second plate) 50, a cover plate 60, and the cap 20. The lower plate 30 is made of a rigid material, for example, a rigid resin material such as polycarbonate and has a chip depression 130 that accommodates the DNA chip 6 formed therein. More specifically, as will be described below, the DNA chip 6 is fixed by being fitted to the depression 130 with the flat surface of a channel area in which a detection channel 100 including an immobilization area to which a nucleic acid probe is fixed is formed directed upward. The lower plate 30 has a groove 132 for a liquid sending system channel communicatively connected to the detection channel 100 formed on the DNA chip 6 formed therein and also has a syringe depression 134 and a tank depression 136 to define a liquid sending system formed therein.

The packing 40 is made of an elastic material, for example, a rubber elastic material such as elastomer and is placed on the lower plate 30. The packing 40 has a swelling portion 144, a liquid sending channel through hole 142, and a lengthwise through groove 146 to define a liquid sending system to correspond to the depression 134 of the lower plate 30 formed therein. In addition, as will be described in detail below, the packing 40 has a groove 111 to provide the detection channel 100 in the DNA chip 6 formed therein. Further, the packing 40 is provided with opening protrusions 141, 143 to define a liquid injection port and has opening protrusions 145, 147 to define an air vent hole formed therein. Further, the packing 40 has a lengthwise through groove 149 to enable access to an electrode pad portion of the DNA chip 6 from outside formed therein.

The upper plate 50 is made of a rigid material, for example, a rigid resin material such as polycarbonate and placed on the packing 40 and the packing 40 is put between the upper plate 50 and the lower plate 30 by being pressurized therebetween. More specifically, a plurality of stud pins 156, 158 is provided on the undersurface of the upper plate 50 by being protruded and the stud pin 156 arranged in the periphery of the upper plate 50 is directly inserted into a peripheral stud hole 138 provided in the periphery of the lower plate 30. Also, the stud pin 158 provided in the center portion of the upper plate 50 as opposed to the packing 40 is inserted into a stud hole 140 provided in the top surface of the lower plate 30 by passing through an insertion hole 148 provided in the center portion of the packing 40. The tip of these stud pins 156, 158 is fixed to the lower plate 30 after being deformed into a retaining boss by thermal caulking. The upper plate 50, the packing 40, and the lower plate 30 are integrated by the stud pins 156, 158. In this structure, the upper plate 50 is fixed to the lower plate 30 so that the packing 40 is pressurized, a fluid-tight liquid sending system is defined between the upper plate 50 and the packing 40, and a fluid-tight liquid sending system is similarly defined between the lower plate 30 and the packing 40. Corresponding to the swelling portion 144, the through hole 142, and the lengthwise through groove 146 formed in the packing 40, the upper plate 50 has a lengthwise through groove 154, a groove (not shown) communicatively connected to the through hole 142, and a lengthwise through groove 159 communicatively connected to the lengthwise through groove 149 formed therein. In addition, the upper plate 50 has through holes 151, 153, 155, 157 into which the opening protrusions 141, 143, 145, 147 of the packing 40 are inserted formed therein.

The upper plate 50 is divided into a back area 150 and a front area 152 by a step 169 and the back area 150 and the front area 152 are linked via the step 169. A cover plate 60 is unremovably attached to the back area 150 of the upper plate 50. The cover plate 60 is made of a rigid material, for example, a rigid resin material such as polycarbonate and has a notched portion 160 into which the cap 20 can be fitted formed therein. The cap 20 is mounted on the notched portion 160. Corresponding to the lengthwise through groove 154 and the like formed in the back area 150 of the upper plate 50, the cover plate 60 is provided with a lengthwise groove 164 having a partition 165.

An engaging protrusion fragment 162 extends downward in the periphery of the undersurface of the cover plate 60 opposed to the back area 150 of the upper plate 50 and the engaging protrusion fragment 162 is unremovably engaged with an engagement hole 131 provided in the lower plate 30 through an insertion hole 166 provided in the upper plate 50 corresponding to the engaging protrusion fragment 162.

(Liquid Sending System Inside the Nucleic Acid Detection Cassette)

Figure 4:
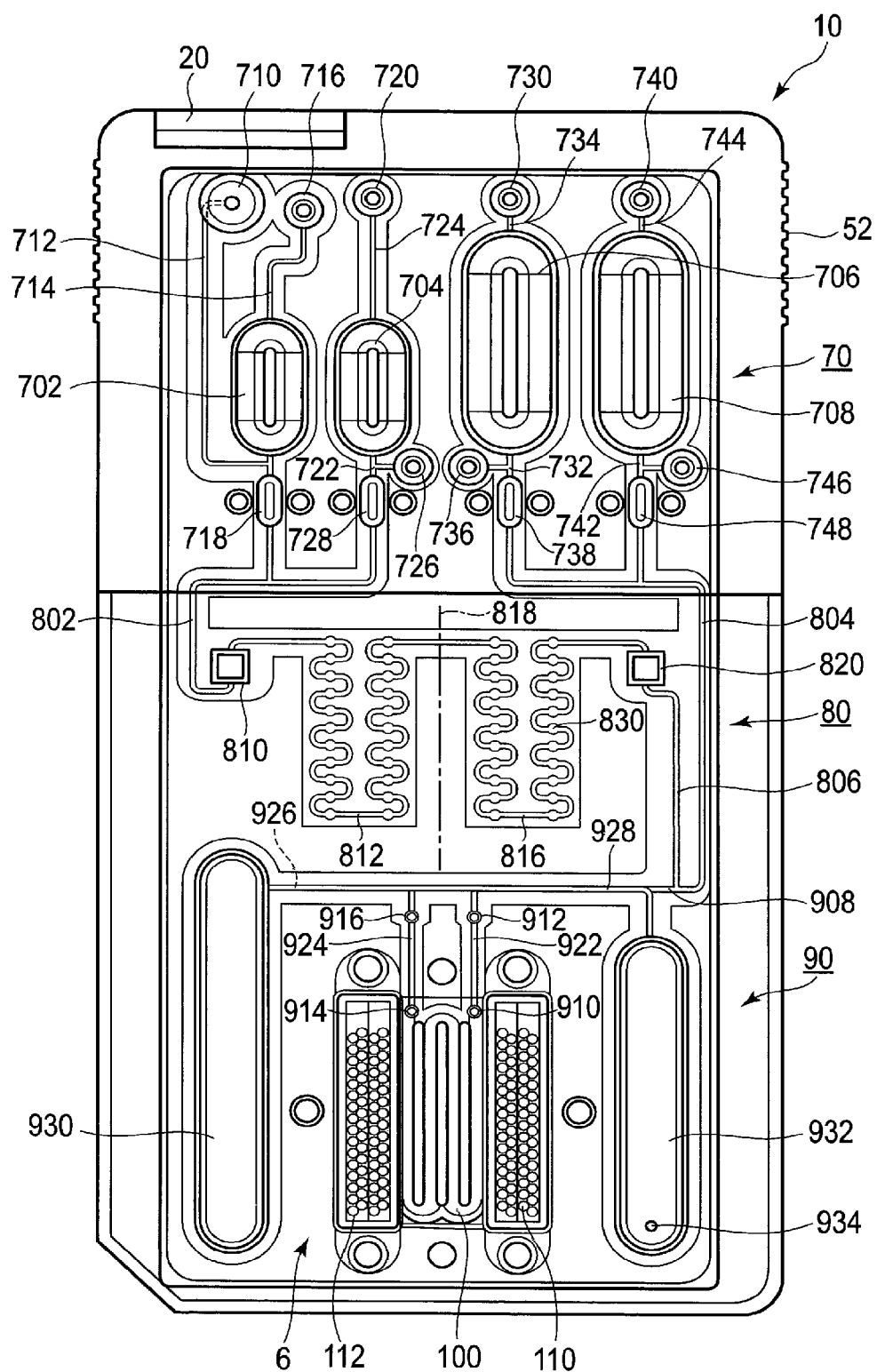
FIG. 4 is a perspective plan view schematically showing an internal structure of the nucleic acid detection cassette shown in FIG. 2 by seeing therethrough.
Figure 5:
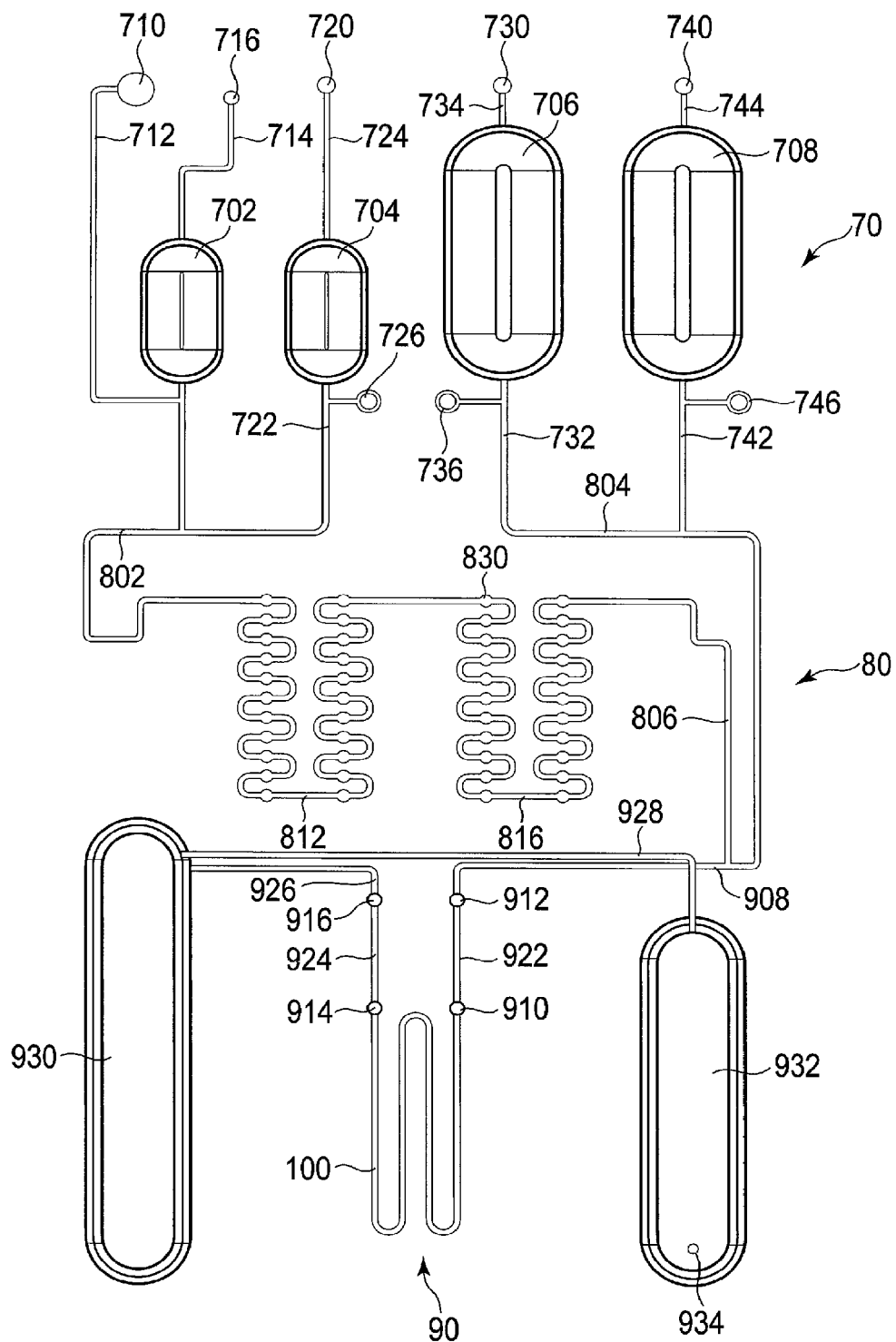
FIG. 5 is a plan view schematically showing a channel provided inside the nucleic acid detection cassette shown in FIG. 2 and each portion connected to the channel.
Figure 6:
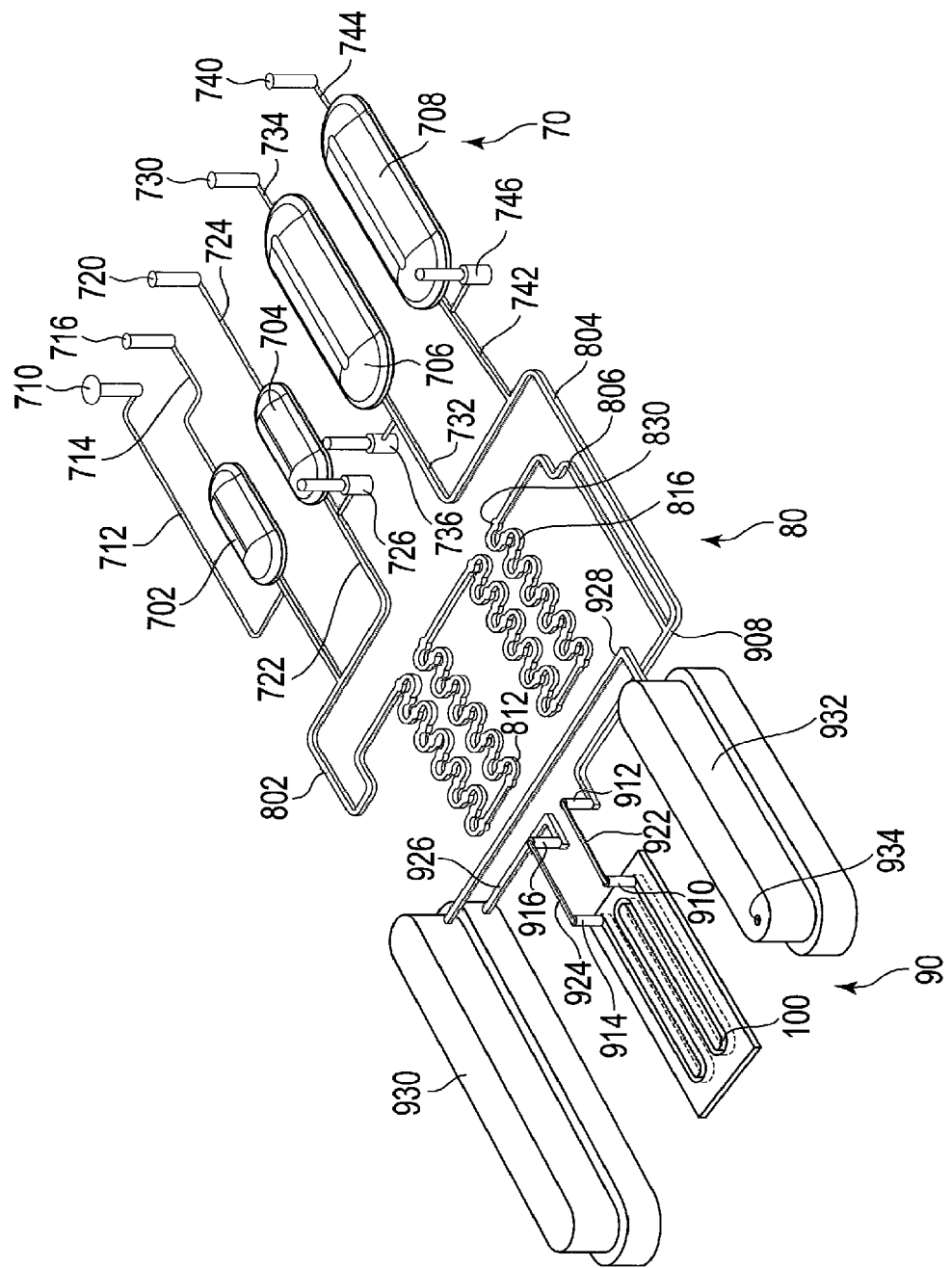
FIG. 6 is a perspective view schematically showing the channel provided inside the nucleic acid detection cassette shown in FIG. 2 and each portion connected to the channel.

The liquid sending system inside the nucleic acid detection cassette will be described with reference to FIGS. 4, 5, and 6. FIG. 4 shows a liquid sending system provided inside the nucleic acid detection cassette 10 by seeing therethrough. FIGS. 5 and 6 show the arrangement of the liquid sending system formed inside the nucleic acid detection cassette 10 shown in FIG. 4.

The nucleic acid detection cassette 10 shown in FIG. 4 includes a syringe portion 70, an amplification unit 80, and a detection unit 90 and the liquid sending system thereof is configured to communicatively connect the syringe portion 70, the amplification unit 80, and the detection unit 90. The syringe portion 70 is covered with the cover plate 60 and the cap 20 and provided inside the nucleic acid detection cassette 10 corresponding to the back area 150 of the upper plate 50. The amplification unit 80 and the detection unit 90 are provided inside the nucleic acid detection cassette 10 corresponding to the front area 152 of the upper plate 50 and constructed of a channel.

In the syringe portion 70, a sample syringe 702, a first cleaning fluid syringe 704, an intercalating agent syringe 706, and a second cleaning fluid syringe 708 are arranged along a short side direction of the nucleic acid detection cassette 10. A sample solution is put into the sample syringe 702 as a storage portion and the first cleaning fluid syringe 704 is filled with a first cleaning fluid. Also, the intercalating agent syringe 706 is filled with an intercalating agent solution and the second cleaning fluid syringe 708 is filled with a second cleaning fluid having the same composition as that of the first cleaning fluid. These syringes 702, 704, 706, 708 are formed as a tubular space extending in the longitudinal direction of the nucleic acid detection cassette 10 and the tubular space is defined between the depression 134 and the swelling portion 144 by the depression 134 of the lower plate 30 being covered with the swelling portion 144 of the packing 40.

The sample syringe 702 shown in FIG. 4 is communicatively connected to a sample injection port 710 that injects a sample solution via a channel 712 through which the sample solution flows and also communicatively connected to an air vent opening 716 via an air vent channel 714. The channel 712 is branched on the inflow/outflow side of the sample syringe 702 and communicatively connected to a normally closed valve 718. Also, the first cleaning fluid syringe 704 is communicatively connected to a first cleaning fluid injection port 720 via a channel 724, communicatively connected to a normally closed valve 728 via a channel 722, and also communicatively connected to an air vent opening 726 via a branched channel branched from the channel 722. The first cleaning fluid is supplied to the first cleaning fluid syringe 704 by being pressurized from the first cleaning fluid injection port 720 via the channel 724. The air inside the first cleaning fluid syringe 704 is released to the outside via the air vent opening 726. Similarly, the intercalating agent syringe 706 is communicatively connected to an intercalating agent injection port 730 via a channel 734, communicatively connected to a normally closed valve 738 via a channel 732, and also communicatively connected to an air vent opening 746 via a channel branched from the channel 732. The intercalating agent is supplied to the intercalating agent syringe 706 by being pressurized from the intercalating agent injection port 730 and the air inside the intercalating agent syringe 706 is released to the outside via an air vent opening 736. Further, the second cleaning fluid syringe 708 is communicatively connected to a second cleaning fluid injection port 740 via a channel 744, communicatively connected to a normally closed valve 748 via a channel 742, and also communicatively connected to the air vent opening 746 via a channel branched from the channel 742. The second cleaning fluid is supplied to the second cleaning fluid syringe 708 by being pressurized from the second cleaning fluid injection port 740 and the air inside the second cleaning fluid syringe 708 is released to the outside via the air vent opening 746. Here, the second cleaning fluid is prepared as a cleaning fluid having the same composition as that of the first cleaning fluid.

Here, the syringes 702, 704, 706, 708 have the function as a tank that stores a sample solution, a cleaning fluid, or a reagent with which the syringes are filled. Also, the syringes 702, 704, 706, 708 have the function of a pump that sends a sample solution, a cleaning fluid, or a reagent with which the syringes are filled to the channels 712, 722, 732, 742. That is, the syringes 702, 704, 706, 708 are formed from the swelling portion 144 having elasticity by being hollowed out and can store the sample solution and the like. Also, a sample solution, a cleaning fluid, or a reagent inside the syringes 702, 704, 706, 708 can be sent to the channels 712, 722, 732, 742 by crushing the swelling portion 144 having elasticity by a syringe rod provided in the liquid sending control mechanism 16 of the testing device 8. The normally closed valves 718, 728, 738, 748 have the function of retaining the storage of a sample solution, a cleaning fluid, or a reagent inside the syringes 702, 704, 706, 708 and when a test is started, the normally closed valves 718, 728, 738, 748 are sequentially released by a valve rod provided in the liquid sending control mechanism 16 of the testing device 8 and retained in a released state. The injection ports 710, 720, 730, 740 and the air vent openings 716, 726, 736, 746 are formed from the opening protrusions 141, 143, 145, 147 provided in the packing 40 and provided to inject a sample solution, a cleaning fluid, or a reagent into the syringes 702, 704, 706, 708 from outside. For the injection ports 720, 730, 740 and the air vent openings 726, 736, 746, a cleaning fluid or a reagent is injected into the syringes 704, 706, 708 and then the cover plate 60 is mounted on the upper plate so that the cleaning fluid or the reagent is sealed inside the syringes 704, 706, 708. More specifically, the cover plate 60 pressure-deforms the opening protrusions 141, 147 provided in the packing 40 for closing. Therefore, after the cleaning fluid or the reagent is injected into the syringes 704, 706, 708, the cleaning fluid or the reagent is prevented from leaking out of the nucleic acid detection cassette 10. Also, for the sample injection port 710 and the air vent opening 716, a sample solution is injected into the sample syringe 702 and then the opening protrusions 143, 145 of the packing 40 are pressure-deformed by the cap 20 for closing. Therefore, after the sample solution is injected into the syringe 702, the sample solution is prevented from leaking out of the nucleic acid detection cassette 10.

The amplification unit 80 is provided with normally open valves 810, 820 on the input port side and the output port side and amplification channels 812, 816 communicatively connected in series are provided between the normally open valves 810, 820. The normally open valve 810 on the input port side is connected to the start-edge side of the amplification channel 812 and the normally open valve 820 on the output port side is connected to the termination side of the amplification channel 816. The normally open valve 810 on the input port side is connected to a channel 802 linked to the normally closed valves 718, 728 of the syringe portion 70 in common. The normally open valve 820 on the output port side is connected to a channel 806. The normally closed valves 738, 748 of the syringe portion 70 are linked to a channel 804 in common. Further, the channel 804 and the channel 806 are connected in common to be communicatively connected to a channel 908 of the detection unit 90.

When a sample solution is supplied to the amplification channels 812, 816, the normally closed valve 718 is opened and the sample syringe 702 is crushed. Therefore, a sample solution is supplied to the amplification channels 812, 816 via the normally closed valve 718, the channel 802, and the normally open valve 810. As a result, the amplification channels 812, 816 are filled with the sample solution. Then, the normally open valves 810, 820 are closed and the amplification unit 80 is heated so that sample DNA in the sample solution is amplified.

The pattern of each of the amplification channels 812, 816 is formed, as shown in FIG. 7 in an enlarged form, in such a way that a meander channel to increase the channel length is folded in a U shape. Then, the amplification channels 812, 816 having a meander pattern in the U shape are communicatively connected so as to form a unidirectional channel by being arranged linearly symmetrically with respect to a center axis 818 between the amplification channels 812, 816. Because the amplification channels 812, 816 have a symmetry pattern with respect to the center axis 818, the heater of the temperature control mechanism 14 provided inside the testing device 8 can be designed such that the amplification channels 812, 816 are heated relatively uniformly.

When sample DNA is amplified, the normally open valve 810 on the input port side and the normally open valve 820 on the output port side of the amplification unit 80 are closed by the valve rod provided inside the testing device 8. Therefore, a situation in which a sample solution swollen by heat provided to the amplification unit 80 for amplification of sample DNA flows out to the channels 802, 806 outside the amplification unit 80 through the input port or output port of the amplification unit 80 to be mixed with a reagent or the like can be prevented.

(Amplification Channel of the Nucleic Acid Detection Cassette)

As will be described in detail below, a well 830 is arranged at fixed intervals or more along the channel in each of the amplification channels 812, 816. In the example shown in FIG. 7, the wells 830 are arranged by being spaced by a substantially fixed channel length in the amplification channels 812, 816 in a meander shape and thus, the wells 830 are arranged by being linearly dotted inside the amplification unit 80. Because the wells 830 are arranged by being linearly dotted, the heater of the temperature control mechanism 14 can similarly be designed such that these wells 830 are heated relatively uniformly.

The amplification channels 812, 816 arranged in the amplification unit 80 includes a plurality of the wells 830, an interval channel connecting wells, an upstream channel leading from outside the amplification unit 80 to the well 830 positioned most upstream, and a downstream channel leading from the well 830 positioned most downstream to the outside of the amplification unit 80. The width of a channel among channels included in the nucleic acid detection cassette is defined as the length in a direction perpendicular to the axial direction of the channel (the length in the cross section of a channel). The width of a well is defined as the length in a direction perpendicular to the axial direction of the amplification channels 812, 816 including the well 830 (the length in the cross section of a well as a channel). The width of the well 830 is defined larger than the width of the interval channel and the width of each of the upstream channel and the downstream channel. The width of the interval channel and the widths of the upstream channel and the downstream channel may be, for example, about 0.05 mm to about 1.5 mm for each and is preferably defined as about 0.5 mm. The width of the well 830 only needs to be larger than the width of the interval channel and the width of each of the upstream channel and the downstream channel and may be, for example, about 0.2 mm to about 3.0 mm. If the width of the interval channel is, for example, about 0.5 mm, the width of the well 830 is preferably about 1 mm. The width of the well 830 may be, for example, 1.5 times to 3.0 times the width of the interval channel and preferably, the width of the well 830 may be 1.7 times to 2.3 times the width of the interval channel.

A mutually different type of primer set 832 is releasably fixed to each of the plurality of wells 830 provided in the amplification unit 80. When one or a plurality of sample DNA (or sample RNA or sample nucleic acid of some type) is supplied into the amplification unit 80, the primer set 832 fixed is released into the sample solution. Then, when the amplification unit 80 is heated by the heater of the temperature control mechanism 14, the plurality of sample DNA is multi-amplified by a plurality of types of the primer set 832. Here, one type of the primer set including a plurality of primers needed to amplify the intended one type of sample DNA is fixed to each of the wells 830.

The arrangement of the wells 830 will be described with reference to FIG. 7. A well 830 (2) is formed between an interval channel 842 and an interval channel 844. The interval channel 844 is formed downstream of the well 830 (2) and a well 830 (4) is formed further downstream of the interval channel 844. Well wall surfaces 853, 855 defining the well 830 (2) protrude to the outer side from the channel wall defining the width of the interval channels 842, 844. When the well wall surfaces 853, 855 are viewed from above in FIG. 7, these wall surfaces exhibit a curve as an arc obtained when a portion of each circle is cut by a straight line. Then, both ends of the well wall surfaces 853, 855 are connected to respective terminals of the interval channels 842, 844. The terminals of the well wall surfaces 853, 855 and terminals of the channels 842, 844 may be connected as a connection of a curve and a straight line as shown in FIG. 7 or as a connection of a curve in which the terminals smoothly continue to each other. Here, an example in which the shape when the well wall surfaces 853, 855 are viewed from above is an arc is shown, but an embodiment is not limited to such an example. For example, the shape when the well wall surfaces 853, 855 are viewed from above may be an elliptic arc obtained when an ellipse is cut by a straight line or a shape combining a plurality of straight lines, a plurality of curves, or a straight line and a curve. Preferably, the shape of the well wall surface when viewed from above is a substantial arc shape such as an elliptic arc or an arc.

The primer set 832 needed to amplify one type of sample DNA to be amplified is releasably fixed to the wall surface of each of the wells 830 (2), 830 (4). If the amplification method is, for example, the PCR method, the primer set needs to include a forward primer and a reverse primer. If the amplification method is, for example, LAMP, the primer set needs to include an FI primer, a BI primer, an F3 primer, and a B3 primer.

The primer set 832 is fixed into the wells 830 (2), 830 (4) by dripping a solution containing the primer set into the wells 830 (2), 830 (4) and drying the solution. Because the primer set solution is dripped into the wells 830 (2), 830 (4), instead of the channel, the primer set can be fixed to a desired position more correctly.

An interval D (830) of the two wells 830 formed in the amplification channels 812, 816 is defined as a distance (that is, a pitch) from the center of one of two wells connected by the interval channel 844 to the center of the other well by passing through the axis of the interval channel. For example, as shown in FIG. 7, the distance D (830) between a center 831 of the well 830 (2) and a center 835 of the well 830 (4) corresponds to the interval of the well 830. Alternatively, the interval D (830) of the two wells 830 may be defined as the distance from the center of one of two wells connected by the interval channel and in which neighboring primer sets along the channel are immobilized to the center of the other measured along the axis of the channel. These definitions are applied to the distance D (830) of the two wells 830 in which the primer set is immobilized and a well in which no primer set is immobilized may be present between the two wells 830 in which the primer set is immobilized and which are adjacent to each other along the channel. The interval of the wells 830 may be about 4 mm or more, that is, about 4 mm pitches, preferably set to about 6 mm or more, that is, about 6 mm pitches or more, and particularly preferably set to about 8 mm or more, that is, about 8 mm pitches or more. By arranging the wells 830 in the amplification channels 812, 816 at such intervals, a plurality of types of base sequences to be amplified contained in sample DNA can be amplified simultaneously or in parallel. Then, each of a plurality of amplification reactions occurring simultaneously or in parallel proceeds satisfactorily and thus, any of a plurality of target DNA contained in the obtained amplification products can be detected. Accordingly, false negative can be prevented from occurring in the detection result. Therefore, more correct tests can be performed. Here, amplifying the plurality of types of base sequences to be amplified in one channel simultaneously or in parallel as described above is called multi-amplification.

With the wells 830 and the interval channel included in the amplification channels 812, 816, fixing of the primer set 832, the supply of liquid to the amplification channels 812, 816, liquid sending of a sample solution containing amplification products after an amplification reaction to the detection unit, and a detection reaction in the detection channel 100 can all be done satisfactorily.

(Detection Channel of the Nucleic Acid Detection Cassette)

Figure 8:
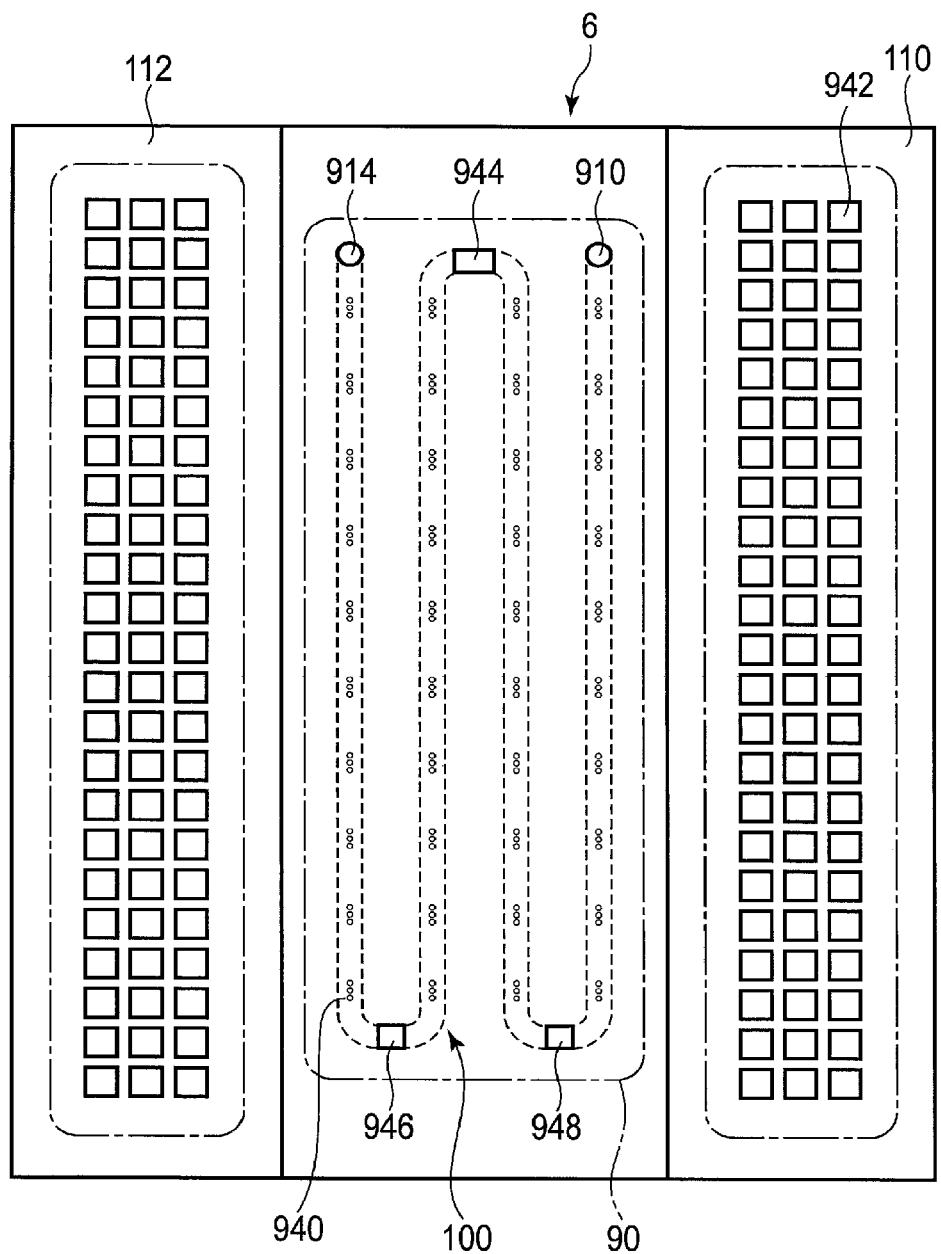
FIG. 8 is a plan view schematically showing a planar structure of a DNA chip of the nucleic acid detection cassette shown in FIG. 2.

The DNA chip 6 shown in FIG. 8 in an enlarged form is arranged in the detection unit 90. The DNA chip 6 is provided with the detection channel 100 having a pattern in which two U-shaped channels are communicatively connected in series. The detection channel 100 is formed by superimposing the DNA chip 6 on a pair of U-shaped grooves 111 provided in the packing 40 and communicatively connected to each other. More specifically, the detection channel 100 is defined between the DNA chip 6 and the packing 40 by the groove 111 in the packing 40 being superimposed on the detection channel 100 on the DNA chip 6 and the packing 40 being fluid-tightly brought into close contact with the DNA chip 6. The detection channel 100 is connected to an input port 910 and an output port 914 provided in the packing 40 on the DNA chip 6. As shown in FIG. 6, the input port 910 is connected to an output port 912 via a channel 922 and the termination of the channel 908 is connected to the output port 912. The output port 914 is connected to an input port 916 via a channel 924 and the start edge of a channel 926 is connected to the input port 916. Therefore, a sample solution containing amplification products generated by an amplification reaction in the amplification unit 80 from the amplification unit 80 to the detection channel 100 of the DNA chip 6 via the channels 806, 908, the output port 912, the channel 922, and the input port 910.

Here, in the above example, the output port 914 is a port from which a sample solution or the like is output and is defined as a port from which a sample solution or the like is pushed out from the lower plate 30 toward the upper plate 50 via a channel hole of the packing 40. Also, the input port 910 is defined as a port to which a sample solution or the like is returned from the upper plate 50 toward the lower plate 30 via a channel hole of the packing 40. Thus, a structure in which a sample solution flows into the detection channel 100 of the DNA chip 6 via a channel hole of the packing 40 is adopted and therefore, a situation in which a sample solution leaks out between the DNA chip 6 and the lower plate 30 can be prevented even if the DNA chip 6 is arranged by fitting into the lower plate 30.

In the configuration of the detection channel described above, a sample solution containing amplification products is pushed out from the amplification channels 812, 816 to flow into the detection channel 100 of the DNA chip 6 by sending a first cleaning fluid with which the first cleaning fluid syringe 704 is filled to the amplification channels 812, 816. Then, as shown in FIG. 6, an intercalating agent and a second cleaning fluid with which the syringes 706, 708 are filled, are supplied to the channel 804 via the channels 732, 742 respectively. The intercalating agent or second cleaning fluid supplied to the channel 804 flows into the detection channel 100 of the DNA chip 6 via the channel 908, the output port 912, the channel 922, and the input port 910. Particularly, a sample solution containing amplification products is pushed into the channel 908 with which the channel 804 is merged via the amplification channels 812, 816 of the amplification unit 80 in liquid sending of the first cleaning fluid to flow into the detection channel 100 of the DNA chip 6. Liquid sending of the first cleaning fluid can reliably send a sample solution from the amplification channels 812, 816 of the amplification unit 80 to the detection channel 100 of the DNA chip 6. Moreover, the channel 804 into which the intercalating agent and the second cleaning fluid flow is separated from the amplification channels 812, 816 and merged with the channel 908. Therefore, the intercalating agent and the second cleaning fluid flow into the detection channel 100 without going through the amplification channels 812, 816, the intercalating agent avoids being mixed with a sample solution of the amplification unit 80 and at the same time, is prevented from being heated by residual heat in the amplification unit 80.

(Waste Liquid Tank of the Nucleic Acid Detection Cassette)

In the detection unit 90, as shown in FIGS. 4, 5, and 6, a waste liquid tank 930 and an auxiliary waste liquid tank 932 to store a waste liquid from the DNA chip 6 are provided. The waste liquid tank 930 is communicatively connected via the output port 914 of the DNA chip 6, the channel 924, the input port 916, and the channel 926. The waste liquid tank 930 is also communicatively connected to the auxiliary waste liquid tank 932 via the channel 926. The auxiliary waste liquid tank 932 is preferably provided with an exhaust hole 934 to exhaust the air inside the auxiliary waste liquid tank 932 so that the air inside the auxiliary waste liquid tank 932 is exhausted when a waste liquid from the DNA chip 6 flows into the waste liquid tank 930. However, if the waste liquid tank 930 and the auxiliary waste liquid tank 932 have sufficient capacities when compared with the amount of liquid flowing into the waste liquid tank, the exhaust hole is not needed because the volume of the waste liquid that flows in can be absorbed by compressing the air inside the tank.

When a second cleaning fluid is sent from the second cleaning fluid syringe 708, an unreacted sample in the detection channel 100 is pushed out by the second cleaning fluid as a waste liquid from the detection channel 100 to flow into the waste liquid tank 930. Then, when an intercalating agent is sent from the intercalating agent syringe 706, the second cleaning fluid in the detection channel 100 is pushed out by the intercalating agent as a waste liquid from the detection channel 100 to similarly flow into the waste liquid tank 930.

Here, a waste liquid generated by a series of testing processes is passed into the waste liquid tank 930 and stored therein and almost no waste liquid flows into the auxiliary waste liquid tank 932 or a very small amount of waste liquid flows into the auxiliary waste liquid tank 932 via the channel 926. However, the sample injection ports 710, 720, 730, 740 and the air vent openings 716, 726, 736, 746 are closed after a sample solution is injected into the sample syringe 702, and a liquid sending system between the sample injection ports 710, 720, 730, 740 and the air vent openings 716, 726, 736, 746, and the exhaust hole 934 of the auxiliary waste liquid tank 932 is maintained fluid-tight. Therefore, even if the liquid sending system is heated by a series of testing processes, a situation in which a waste liquid leaks out from the exhaust hole 934 of the auxiliary waste liquid tank 932 can be prevented.

These waste liquid tanks 930, 932 are formed as a lengthwise space defined by the depression 136 formed in the lower plate 30, the lengthwise through groove 146 in the packing 40, and a depression (not shown) corresponding to the depression 136 formed on the back surface of the upper plate 50. Particularly, the waste liquid tank 930 preferably can have a volume capable of accepting all of a sample solution, a first cleaning fluid, an intercalating agent, and a second cleaning fluid pushed out from the syringes 702, 704, 706, 708.

The channels 712, 714, 722, 724, 732, 734, 742, 744, 802, 804, 806, 908, 926 in the liquid sending system described above are formed by covering the groove 132 formed in the lower plate 30 with the packing 40 like being defined between the groove 132 and the flat undersurface of the packing 40. Similarly, the amplification channels 812, 816 are formed by covering the groove 132 in a meander shape having the wells 830 formed in the lower plate 30 with the packing 40 like being defined between the groove 132 and the flat undersurface of the packing 40. The detection channel 100 of the DNA chip 6 is defined by electrodes being arranged along a U-shaped channel on a flat substrate made of glass or silicon. The detection channel 100 is formed by aligning the U-shaped channel on the substrate with the groove 111 in a U shape provided in the packing 40 and covering the flat substrate with the packing 40 like being defined between the groove in a U shape of the packing 40 and the flat top surface of the substrate.

The ports 910, 914 of the DNA chip 6 correspond to through holes (channel holes) drilled in the packing 40. Also, the output port 912 of the channel 908 and the input port 916 of the channel 926 correspond to through holes (channel holes) drilled in the packing 40. The channel 922 between the output port 912 and the port 910 and the channel 924 between the input port 916 and the port 914 are formed by covering a groove (not shown) formed on the undersurface of the upper plate 50 with the packing 40 like being defined between the groove and the flat top surface of the packing 40. Therefore, the channels leading to the ports 910, 914 of the DNA chip 6 are communicatively connected on the top surface side of the DNA chip 6. In the ports 910, 914 of the DNA chip 6, the upper plate 50 is pressed against the lower plate 30 and both are maintained fluid-tight by the packing 40 therebetween. Therefore, even if the DNA chip 6 has a rigid substrate structure, the DNA chip 6 is maintained in a state of close contact with the packing 40 and the detection channel 100 of the DNA chip 6 is communicatively connected reliably to a liquid sending system channel formed between the lower plate 30 and the packing 40. Even if the detection channel 100 of the DNA chip 6 is heated, a sample solution or the like can be prevented from leaking out of the detection channel 100 of the DNA chip 6.

(Electrode Structure of the DNA Chip)

The DNA chip 6 will be described with reference to FIGS. 3 and 8. As shown in FIG. 3, the DNA chip 6 has the detection channel 100 and electrode pad areas 110, 112 arranged on both sides of the detection channel 100 and the detection channel 100 is formed by the groove 111 on the back face of the packing 40 being covered with a flat area of the substrate made of glass or silicon. In the detection channel 100, as shown in FIG. 8, working electrodes 940 are provided at regular intervals. In addition, electrode pads 942 are arranged in the electrode pad areas 110, 112 and the electrode pads 942 are each electrically connected to the corresponding working electrodes 940. A reference electrode 944 and counter electrodes 946, 948 are provided at the apex of the U shape of the detection channel 100 and each connected to the corresponding electrode pads 942. In FIG. 8, for the sake of simplifying the illustration, wire connections between the electrode pad 942 and the working electrodes 940, the reference electrode 944, and the counter electrodes 946, 948 are omitted.

The working electrode 940 is constructed by a nucleic acid probe containing a sequence complementary to the base sequence of nucleic acid to be detected, for example, a nucleic acid probe to detect SNP (1) to SNP (N) (Single Nucleotide Polymorphism) being fixed to the electrodes, for example, gold electrodes for each type. A plurality of nucleic acid probes is fixed for each type for each of the working electrodes 940. If a complementary base sequence (that is, target DNA) is present in the sample solution under heating, the complementary base sequence is bound to a fixed nucleic acid probe by a hybridization reaction. An unreacted sample solution that is not bound by the hybridization reaction is removed, as described above, by being pushed out from the detection channel 100 by a second cleaning fluid and the working electrode 940 is cleaned by the second cleaning fluid. Then, an intercalating agent is supplied to the detection channel 100 to remove the second cleaning fluid. A fixed voltage is supplied between the working electrodes 940 and the counter electrodes 946, 948 while the working electrodes 940 are immersed in the intercalating agent. Here, the intercalating agent contains a material that recognizes a double strand portion generated by the hybridization reaction on the working electrode 940 and enters and electrochemically activates the portion. A signal current is detected from the working electrode 940 to which a nucleic acid probe as a double strand caused by the hybridization reaction due to the application of a voltage is fixed. The signal current is detected by a current probe contained in the measuring unit 12 shown in FIG. 1 described above being physically brought into contact with the electrode pad 942. The detected current is amplified and stored in a buffer of the measuring unit 12 before being output by the computer 4 positioned outside as detection data.

Here, the reference electrode 944 acts to make an applied voltage between the working electrodes 940 and the counter electrodes 946, 948 constant via a feedback circuit by monitoring the applied voltage between the working electrodes 940 and the counter electrodes 946, 948.

(Top Surface Structure of the Nucleic Acid Detection Cassette)

The top surface structure of the nucleic acid detection cassette 10 will be described in more detail again with reference to FIGS. 2, 9, and 10 to 14.

As shown in FIG. 2, the cover plate 60 is fixed by being fitted to the nucleic acid detection cassette 10 in a rectangular shape. The lengthwise grooves 164 are arranged in parallel along the width direction of the nucleic acid detection cassette 10 and the syringes 702, 704, 706, 708 are arranged inside the lengthwise grooves 164 like swelling into the lengthwise grooves 164. The cover plate 60 is provided with T-shaped depressions 41, 42, 44, 46 along the width direction of the nucleic acid detection cassette 10 and, as shown in FIG. 9, a cantilever structure of the normally closed valves 718, 728, 738, 748 is provided behind the depressions 41, 42, 44, 46. When the cantilever structure is operated to open from the back face side of the cover plate 60 by the valve rod of the liquid sending control mechanism 16, tongues 181, 182, 184, 186 inside the depressions 41, 42, 44, 46 are pushed to open the normally closed valves 718, 728, 738, 748 behind the tongues. A detailed structure of the normally closed valves 718, 728, 738, 748 will be described in detail below with reference to FIGS. 23 to 25.

The lengthwise grooves 164 in which the syringes 702, 704, 706, 708 are arranged have a width that prevents a finger from entering and the lengthwise grooves 164 having a long length are provided with, as shown in FIG. 2, the partition 165 to prevent a finger from entering in the longitudinal direction. The nucleic acid detection cassette 10 shown in FIG. 2 is provided with a non-slip indented groove 139 on both side faces in the width direction of the upper plate 50 where the cover plate 60 is provided and the lower plate 30 so that the user can reliably grip the nucleic acid detection cassette 10.

FIG. 9 shows the appearance when the cover plate 60 is removed from the nucleic acid detection cassette 10 shown in FIG. 2. The tip of the opening protrusion 141 for the first cleaning fluid injection port 720, the intercalating agent injection port 730, and the second cleaning fluid injection port 740 and the tip of the opening protrusion 147 for the air vent openings 726, 736, 746 provided in the packing 40 are exposed in the back area 150 of the upper plate 50 exposed by the cover plate 60 being removed. In a manufacturing process of the nucleic acid detection cassette 10, a first cleaning fluid is injected into the first cleaning fluid syringe 704 via the first cleaning fluid injection port 720, an intercalating agent solution is injected into the intercalating agent syringe 706 via the intercalating agent injection port 730, and a second cleaning fluid is injected into the second cleaning fluid syringe 708 via the second cleaning fluid injection port 740 in a state in which, as shown in FIG. 9, the cover plate 60 is removed. Then, the cover plate 60 is unremovably mounted and fixed to the back area 150 of the upper plate 50. For the mounting and fixing, the undersurface of the cover plate 60 is pressed against the opening protrusion 141 and the opening protrusion 147 so that the opening protrusion 141 and the opening protrusion 147 are pressure-pressed against the undersurface of the cover plate 60. Therefore, when the cover plate 60 is mounted on the upper plate 50, the first cleaning fluid injection port 720, the intercalating agent injection port 730, the second cleaning fluid injection port 740, and the air vent openings 726, 736, 746 are closed.

The cover plate 60 of the nucleic acid detection cassette 10 shown in FIG. 2 is mounted and fixed to the upper plate 50 such that, as shown in FIG. 3, the top surface of the cover plate 60 is flush with the front area 152. A depression 51 in a rectangular shape is formed in the front area 152 of the upper plate 50 to fix an amplification unit area and make heating easier and rod holes 52, 54 to operate the normally open valves 810, 820 are provided on both sides of the depression 51. The normally open valves 810, 820 are opened by the valve rods of the liquid sending control mechanism 16 being inserted into the rod holes 52, 54 and the tips thereof being pressed against the normally open valves 810, 820. Probe holes 656, 658 in a lengthwise shape to insert a current probe into the electrode pad areas 110, 112 of the DNA chip 6 in which electrode pads are arranged are formed in parallel in the front area 152 of the upper plate 50.

In the back area 150 of the nucleic acid detection cassette 10, as shown in FIG. 9, the syringes 702, 704, 706, 708 are arranged and depressions 201, 202, 203, 204 for the normally closed valves 718, 728, 738, 748 and rod holes 211, 212, 213, 214 are provided between the syringes 702, 704, 706, 708 and the step 169. As shown in FIG. 3, hole portions 201A, 202A, 203A, 204A constituting the depressions 201, 202, 203, 203 shown in FIG. 2 are formed in the upper plate 50. Also as shown in FIG. 3, hole portions 211A, 212A, 213A, 214A constituting the rod holes 211, 212, 213, 214 shown in FIG. 2 are formed in the upper plate 50. The normally closed valves 718, 728, 738, 748 formed inside the depressions 201, 202, 203, 203 have a structure as a normally open valve when the cover plate 60 is removed and have, as will be described below, a structure as a normally closed valve when the cover plate 60 is mounted and the protrusions of the cover plate 60 are inserted into the depressions 201, 202, 203, 203.

Figure 11:
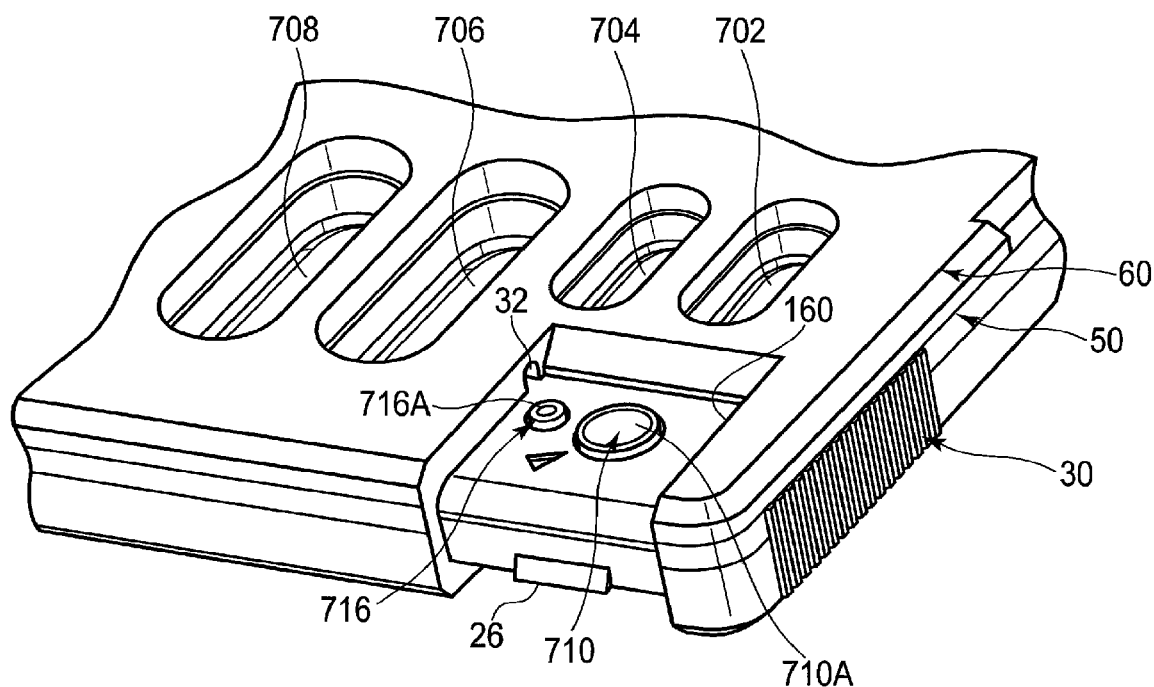
FIG. 11 is a partial perspective view showing a cap internal configuration of the nucleic acid detection cassette by removing the cap from the nucleic acid detection cassette shown in FIG. 2.

As shown in FIG. 10, the cap 20 is mounted on the cover plate 60 fitted and fixed to the nucleic acid detection cassette 10 in a rectangular shape. The cap 20 is formed in an L shape having a top surface flat portion 21 in a rectangular shape and a side piece 23 extending from the top surface flat portion 21 along the back side face of the nucleic acid detection cassette 10. An axis portion 25 to open or close the cap 20 is provided in the side portion of the flat portion 21 and the side piece 23 is provided with an engaging portion 27 engaged and fixed to an engaging protrusion 26 of the lower plate 30. The notched portion 160 that accepts the flat portion 21 of the cap 20 is formed in the cover plate 60 and, as shown in FIG. 11, a pivoted hole 32 to pivotally support the axis portion 25 of the cap 20 is formed in the side face of the notched portion 160. When the cap 20 is closed using the axis portion 25 as a supporting point, the top surface flat portion 21 in a rectangular shape of the cap 20 is linked to the top surface of the cover plate 60 so that the cap 20 is fitted into the nucleic acid detection cassette 10 like providing a substantially flat surface to the nucleic acid detection cassette 10. When the cap 20 is pressed against the cover plate 60 for the fitting, the engaging portion 27 of the cap 20 is engaged with the engaging protrusion 26 of the lower plate 30. As a result, the cap 20 is unremovably fixed to the lower plate 30.

Before the nucleic acid detection cassette 10 is filled with a sample solution, the cap 20 is mounted in a state released from the cover plate 60 and maintained rotatable around the axis portion 25 while being pivotally supported on the cover plate 60 by the axis portion 25. After the nucleic acid detection cassette 10 is filled with a sample solution, as described above, the cap 20 is unremovably fixed to the nucleic acid detection cassette 10. Unremovable fixing of the cap 20 to the nucleic acid detection cassette 10 clearly demonstrates to the user that a sample solution is stored in the nucleic acid detection cassette 10 and can prevent a situation in which a sample solution is erroneously injected into the nucleic acid detection cassette 10 again or the like.

Figure 12:
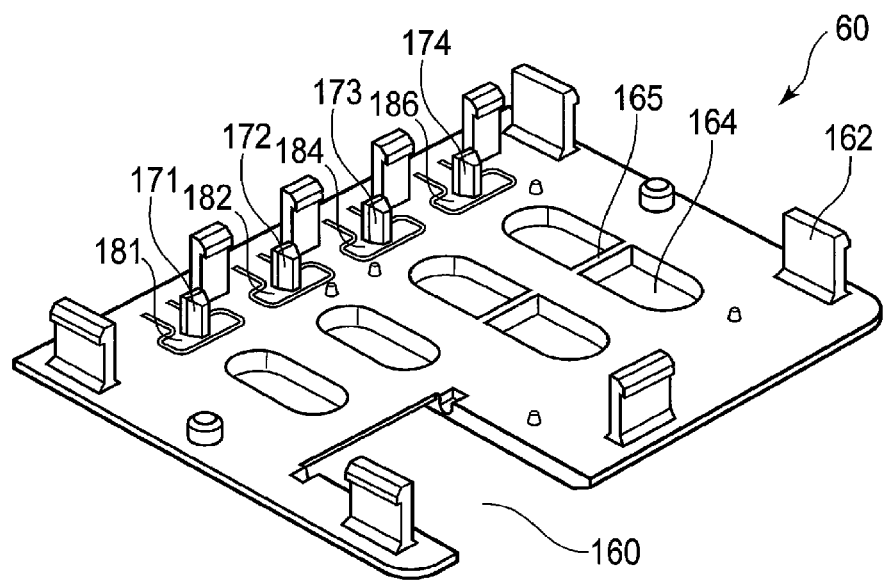
FIG. 12 is a perspective view showing a back face of the cover mounted on the nucleic acid detection cassette shown in FIG. 2.

The cover plate 60 has a back surface side structure schematically shown in FIG. 12. As shown in FIG. 12, the notched portion 160 is formed corresponding to the cap 20 on the back surface side of the cover plate 60. The tongues in a T shape (T-shaped tongues) 181, 182, 184, 186 are arranged along the side abutting on the step 169. The tongues in a T shape (T-shaped tongues) 181, 182, 184, 186 are formed by notching the cover plate 60 and formed movably independently on the cover plate 60. As shown in FIG. 2, in the top surface side of the cover plate 60, these tongues in a T shape (T-shaped tongues) 181, 182, 184, 186 are arranged along the width direction of the nucleic acid detection cassette 10 and formed so as to be arranged inside the depressions in a T shape (T-shaped depressions) 41, 42, 44, 46. More specifically, these tongues in a T shape 181, 182, 184, 186 have a base portion pivotally supported and fixed to the cover plate 60 and constitute a cantilever structure in which the tongues in a T shape 181, 182, 184, 186 are movable. The tongues in a T shape 181, 182, 184, 186 have protruding portions 171, 172, 173, 174 protruding from the tongues in a T shape 181, 182, 184, 186 and the protruding portions 171, 172, 173, 174 are moved together with the tongues in a T shape 181, 182, 184, 186. As will be described in detail below, the protruding portions 171, 172, 173, 174 close a tubular portion 55 constituting a normally closed valve when the cover plate 60 is fitted and fixed to the nucleic acid detection cassette 10 in a rectangular shape.

Figure 13:
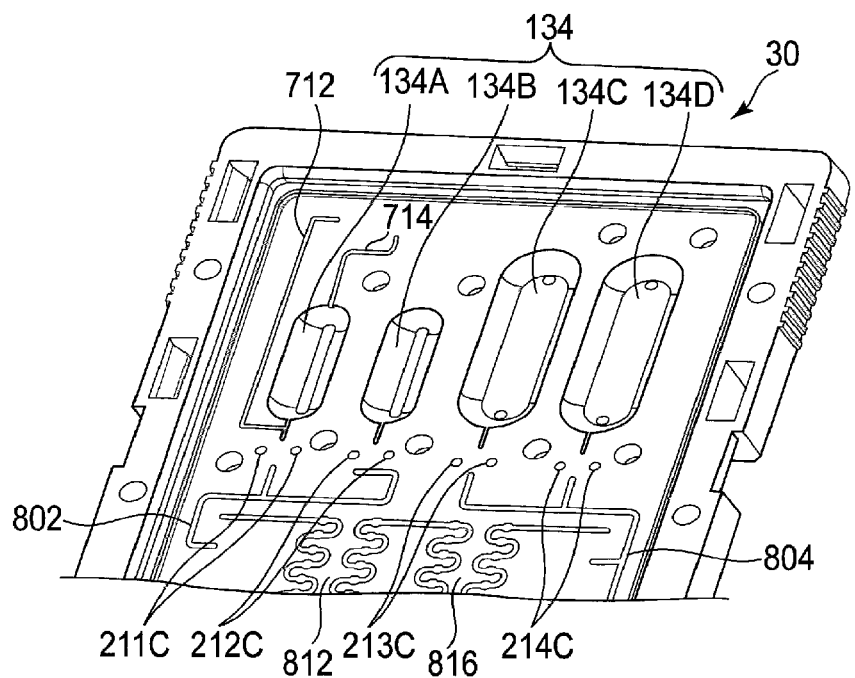
FIG. 13 is a partial perspective view schematically showing a portion of a lower plate of the nucleic acid detection cassette shown in FIG. 3.

FIG. 13 schematically shows the structure of a back portion of the lower plate 30. The channels 712, 714, 802, 804 and depressions to form the amplification channels 812, 816 are formed on the surface of the back area of the lower plate 30. Further, depressions for syringe 134 (134A, 134B, 134C, 134D) are formed. The depressions for syringe 134A, 134B, 134C, 134 constitute the syringes 702, 704, 706, 708 respectively. In the lower plate 30, hole portions 211C, 212C, 213C, 214C constituting the rod holes 211, 212, 213, 214 are formed.

Figure 14:
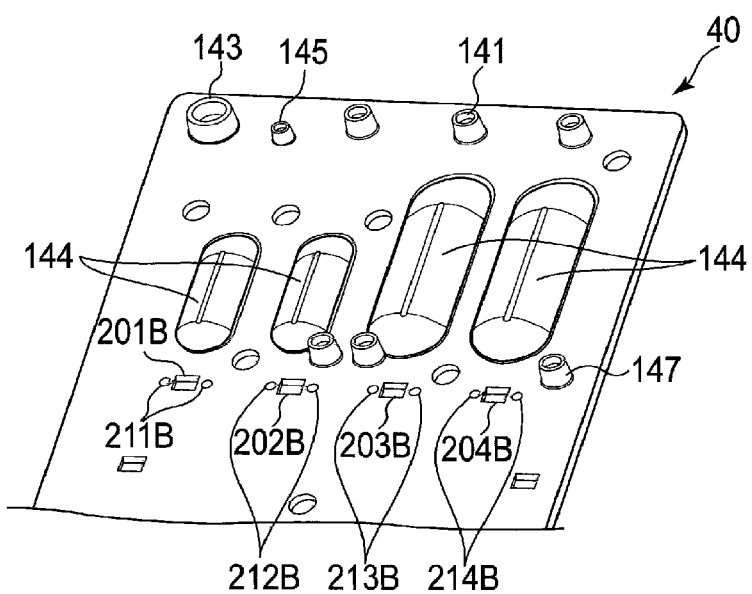
FIG. 14 is a partial perspective view schematically showing a portion of packing of the nucleic acid detection cassette shown in FIG. 3.

FIG. 14 schematically shows the structure of the back area of the packing 40. The packing 40 is provided with the opening protrusions 141, 147 to define a liquid injection port and has the opening protrusions 143, 145 to define an air vent hole formed therein. Depressions 201B, 202B, 203B, 204B constituting the normally closed valves 718, 728, 738, 748 are formed in front of the swelling portion 144 defining the syringes 702, 704, 706, 708. Hole portions 211B, 212B, 213B, 214B overlapping with the hole portions 211C, 212C, 213C, 214C are formed around these depressions 201B, 202B, 203B, 204B.

FIG. 15 is a transverse sectional view showing the structure of the normally closed valves 718, 728, 738, 748 along B-B in FIG. 9 when the cover plate 60 is removed. When, as described above, the upper plate 50 is fixed to the lower plate 30 via the packing 40, the depressions 201, 202, 203, 204 and the rod holes 211, 212, 213, 214 are provided in the upper plate 50. More specifically, the upper plate 50, the packing 40, and the lower plate 30 are combined such that the hole portions 201A, 202A, 203A, 204A of the upper plate 50 and the depressions 201B, 202B, 203B, 204B of the packing 40 are aligned to provide the depressions 201, 202, 203, 203 in the upper plate 50. Also, the upper plate 50, the packing 40, and the lower plate 30 are combined such that the hole portions 211C, 212C, 213C, 214C of the lower plate 30, the hole portions 211B, 212B, 213B, 214B of the packing 40, and the hole portions 211A, 212A, 213A, 214A of the upper plate 50 are aligned to provide the rod holes 211, 212, 213, 214 in the upper plate 50.

The tubular portion 55 that is flexible and provided in the packing 40 is arranged inside the depressions 201, 202, 203, 203. A cavity portion as a channel for the normally closed valves 718, 728, 738, 748 is formed between the tubular portion 55 and the top surface of the lower plate 30 where the tubular portion 55 is arranged. These tubular portions 55 are each communicatively connected to the channel 802 or the channel 712 and the channel 722, and the channel 804 or the channel 732 and the channel 742. The tubular portion 55 is formed, like the normally open valve 810, integrally with the packing 40 inside a depression 57 and so is formed sufficiently thinner than a thickness T1 of the packing 40. When formed in a normally closed valve described in detail below, the cover plate 60 shown in FIG. 12 is mounted on the upper plate 50 and the protruding portions 171, 172, 173, 174 provided in the cover plate 60 are inserted into the depressions 201, 202, 203, 203. Then, the protruding portions 171, 172, 173, 174 crush the tubular portions 55 to close the cavity portions. With the cavity portions closed, a channel between the channel 802 or the channel 712 and the channel 722 and a channel between the channel 804 or the channel 732 and the channel 742 are cut off to be formed into a structure of normally closed valves. These cavity portions communicatively connect the channel 802 and the channel 712 or the channel 722, and the channel 804 and the channel 732 or the channel 742. As is evident from the structure, the tubular portion 55 is formed integrally with the packing 40 inside the depressions 201, 202, 203, 203 and so is formed sufficiently thinner than the thickness T1 of the packing 40 and preferably larger than a thickness T2 (T1>T2). Here, the thickness T1 corresponds to the thickness of a convex area of the packing 40 formed from convex areas and concave areas and the thickness T2 corresponds to the thickness of a concave area. The tubular portion 55 is formed in an arch shape and the cavity portion is formed in a diameter smaller than the thickness of the tubular portion. The top surface of the tubular portion 55 is partially formed flat so that the protruding portions 171, 172, 173, 174 shown in FIG. 12 can be brought into contact more easily. Therefore, as shown in FIG. 16, the cavity portion provided inside the tubular portion 55 can be crushed by a tip portion of the protruding portions 171, 172, 173, 174 inserted from outside so that the cavity portion is closed by crushing the tubular portion 55. With the cavity portion closed, the channel between the channel 802 or the channel 712 and the channel 722 and the channel between the channel 804 or the channel 732 and the channel 742 are cut off.

(Structure of the Sample Injection Port)

Figure 17:
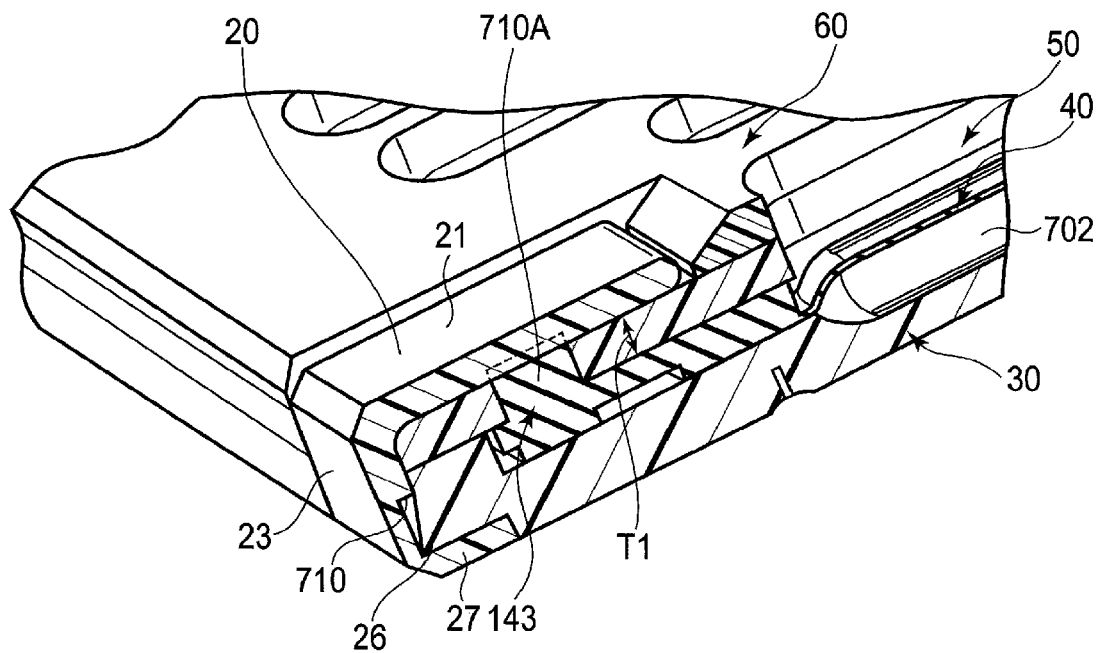
FIG. 17 is a partial section perspective view of the nucleic acid detection cassette along a C-C line in FIG. 2.

The structure of the sample injection port will be described in detail with reference to FIGS. 10, 11, and 17. FIG. 17 shows a cross section along a C-C line in FIG. 11 after a sample solution is injected into the syringe 702.

As shown in FIG. 11, the sample injection port 710 is provided in the back area 150 of the nucleic acid detection cassette 10. In FIG. 11, the cap 20 is removed and the sample injection port 710 is exposed to clearly show the sample injection port 710. Here, the sample injection port 710 and the air vent opening 716 are provided close to each other such that the openings thereof can be closed by the cap 20 and at the same time, locked.

Before a sample solution is injected, as shown in FIG. 10, a state in which the cap 20 is open is maintained. The air vent opening 716 communicatively connected to the sample injection port 710 is formed to release the air inside the channel 712, the syringe 702, and the channel 714 when a sample solution is injected from the sample injection port 710. When a sample solution is injected, the normally closed valve 718 cuts off the channel between the channel 712 and the channel 802 and therefore, the sample syringe 702 is filled with the sample solution without the sample solution flowing out into the channel 802.

The sample injection port 710 is formed in a conic shape so that a needle (not shown) of a micro-syringe that injects a sample solution is guided to cause the sample solution to flow into the channel 712. After a sample solution or a reagent flows in, as shown in FIG. 17, the cap 20 is closed and fixed to the lower plate 30. More specifically, when the cap 20 is pressed against the cover plate 60 to close the cap 20, the engaging portion 27 of the cap 20 is engaged with the engaging portion 26 of the lower plate 30. As a result, the cap 20 is unremovably fixed to the lower plate 30.

When the cap 20 is fitted and fixed after a sample solution is injected into the sample syringe 702 via the sample injection port 710, as shown in FIG. 17, the sample injection port 710 and the air vent opening 716 are, as indicated by a broken line, pressure-deformed by the undersurface of the cap 20 so that the sample injection port 710 and the air vent opening 716 are closed. At this point, a top edge 710A of the sample injection port 710 and a top edge 716A of the air vent opening 716 are thicker than the thickness T1 of the upper plate 50 and are formed long enough to protrude from the upper plate 50. Therefore, the sample injection port 710 and the air vent opening 716 are deformed by the undersurface of the cap 20.

The protruding lengths of the top edge 710A and the top edge 716A have to be formed such that the engaging portion 27 can be engaged with the engaging portion 26.

Because the sample injection port has the structure as described above, the nucleic acid detection cassette 10 is sealed fluid-tightly and when a sample is amplified or an electrochemical reaction of a sample is detected, a sample solution is prevented from leaking out from the nucleic acid detection cassette 10 even if the nucleic acid detection cassette 10 is heated.

(Structure of the Syringe)

The structure of the four syringes 702, 704, 706, 708 provided in the syringe portion 70 will be described in detail with reference to FIGS. 4 and 18 to 23.

Figure 18:
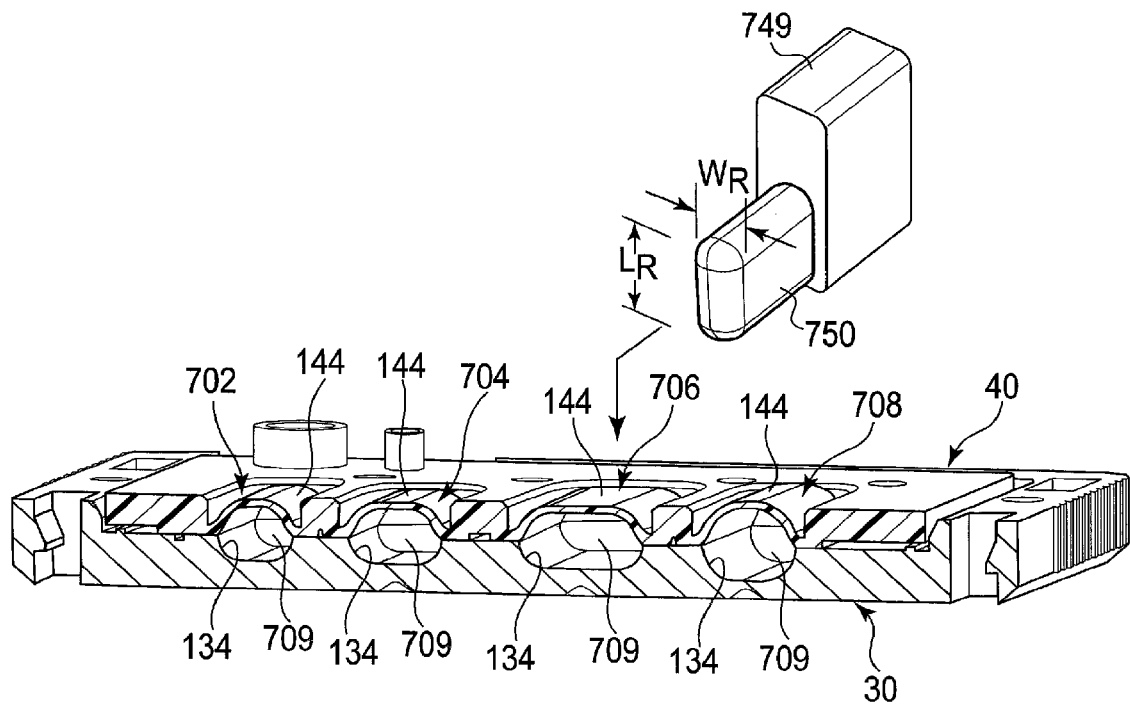
FIG. 18 is a partial section perspective view of the nucleic acid detection cassette shown along a D-D line in FIG. 2.

FIG. 18 shows a sectional structure along a D-D line of the nucleic acid detection cassette 10 shown in FIG. 9. As shown in FIG. 18, the sample syringe 702, the first cleaning fluid syringe 704, the intercalating agent syringe 706, and the second cleaning fluid syringe 708 are arranged along the width direction of the nucleic acid detection cassette 10 from left to right of the drawing. As described with reference to FIGS. 13 and 14, each of the syringes 702, 704, 706, 708 is defined between the depression 134 and the swelling portion 144 by covering the depression 134 in an elongated shape of the lower plate 30 made of a rigid material with the swelling portion 144 in an elongated shape of the packing 40 made of an elastic material and has a tubular space 709 extending in the longitudinal direction of the nucleic acid detection cassette 10.

The operations of injecting a sample solution into the sample syringe 702, supplying a first cleaning fluid into the first cleaning fluid syringe 704, supplying an intercalating agent into the intercalating agent syringe 706, and supplying a second cleaning fluid into the second cleaning fluid syringe 708 will be described more specifically below with reference to the operations of a testing device.

A sample solution, a cleaning fluid, or a reagent with which the tubular space 709 of the syringes 702, 704, 706, 708 configured as described above is filled is sent after the liquid sending control mechanism 16 of the testing device 8 being operated. More specifically, four rod holding portions 749 are mounted on the liquid sending control mechanism 16 and, as shown in FIG. 18, a syringe rod 750 is provided at the tip of the rod holding portion 749. As shown in FIG. 18, the tip surface of the syringe rod 750 is elongated and has a shape in which both end portions along the width direction and the depth direction are convexly curved. The tip of the syringe rod 750 is, as shown in FIG. 19, brought into contact with the swelling portion 144 made of an elastic material of the syringe 702 (or 704 or 706 or 708) via the lengthwise groove 164 of the cover plate 60 and the lengthwise groove 154 of the upper plate 50. Then, as shown in FIG. 20, the swelling portion 144 is crushed by imposing a load on the swelling portion 144 through the syringe rod 750 to send the sample solution, cleaning fluid, or reagent with which the tubular space 709 is filled to the channels 712, 722, 732, 742.

When the swelling portion 144 of the syringe 702 (or 704 or 706 or 708) is crushed by the syringe rod 750, reducing a compressive load of the syringe rod on the swelling portion 144 is desired to implement miniaturization and weight reduction of the nucleic acid detection cassette 10. Also for effective use of reagent (minimization of the reagent cost), minimizing a residual liquid in the syringe 702 (or 704 or 706 or 708) after liquid sending is desired.

Here, if minimizing a residual liquid in the tubular space 709 of the syringe is emphasized when the swelling portion 144 of the syringe 702 (or 704 or 706 or 708) is crushed by the syringe rod 750, an increased compressive load on the swelling portion 144 or a reduced displacement margin may be generated.

In fact, the syringe width $W_B$ shown in FIG. 19 was set to 4.0 mm, the syringe rod width $W_R$ was set to 3.0 mm, and the thickness $t_E$ of the swelling portion was set to 0.5 mm. 200 μL of reagent was injected into the syringe. Then, a test in which an operation to crush the swelling portion made of elastomer (hardness: 60) of the syringe by imposing a load thereon through the syringe rod such that the amount of residual liquid is 5 to 8 μL is repeated 10 times was performed before measuring the load through the syringe rod. The result is shown in FIG. 21A.

As is shown in FIG. 21A, a high load of around 1.0 kgf needs to be imposed and in addition, a problem of a reduced displacement margin is caused by variations of the load around 1.0 kgf. Such a problem is caused because the elastic material member to be crushed is not flat and has, as shown in FIG. 19, a shape swollen by protruding in a direction opposite to the depression 134 in an elongated shape of the lower plate 30.

Here, the "syringe width $W_B$" means, as shown in FIG. 19, the length in the width direction of the opening of the depression 134 in an elongated shape constituting the syringe.

If the syringe width is $W_B$, the syringe rod width is $W_R$, and the thickness of the swelling portion is $t_E$ in the syringe 702 (or 704 or 706 or 708) having the swelling portion 144 described above in an embodiment, the syringe width $W_B$ is set such that the following formula is satisfied:

$$W_R + 3t_E \leq W_B \leq W_R + 4t_E \quad (1)$$

Here, though depending on the cassette dimensions, the thickness of the swelling portion is preferably set to 0.1 to 1.0 mm. By setting the syringe width $W_B$ as described above, the residual liquid in the syringe after liquid sending can be minimized for effective use of reagent (minimization of the reagent cost) of the nucleic acid detection cassette 10.

In fact, that the minimization of residual liquid by the syringe rod can be achieved was verified by the following experiments:

Example 1

The syringe rod width $W_R$ was fixed (constant) to 3.0 mm, the thickness $t_E$ of the swelling portion was fixed to 0.5 mm, and the syringe width $W_B$ was changed to 4.0 mm, 4.5 mm, 5.0 mm, and 5.5 mm (Examples 11 to 14). 200 μL of reagent was injected into the syringe to be fully filled therewith. Then, a force of 1 kgf was applied to the syringe rod to impose a load on the swelling portion made of elastomer (hardness: 60) at a speed of 1 mm/s to crush the swelling portion and a reagent in the syringe was pushed out from the channel connected to the syringe. After the syringe rod stopped, the amount of reagent remaining in the syringe was measured. The measurement was made five times for each syringe width $W_B$. The result is shown in Table 1 below.

TABLE 1

| | | Example 11 | Example 12 | Example 13 | Example 14 |
|---|---|---|---|---|---|
| | | Syringe width ($W_B$) | | | |
| | | 4.0 mm | 4.5 mm | 5.0 mm | 5.5 mm |
| Residual liquid amount (times) | 1 | 65 μL | 4 μL | 6 μL | 12 μL |
| | 2 | 63 μL | 5 μL | 5 μL | 17 μL |
| | 3 | 70 μL | 5 μL | 8 μL | 15 μL |
| | 4 | 82 μL | 3 μL | 8 μL | 18 μL |
| | 5 | 35 μL | 7 μL | 7 μL | 21 μL |

As is evident from Table 1 above, it turns out that in Examples 12, 13 in which the syringe rod width $W_R$ was fixed (constant) to 3.0 mm, the thickness $t_E$ of the swelling portion was fixed to 0.5 mm, and the syringe width $W_B$ was set to satisfy the above formula (1), when compared with Examples 11, 14 in which the syringe width $W_B$ deviates from the above formula (1), the amount of residual liquid in the syringe can conspicuously be reduced. Particularly, as shown in Examples 14, 13, 12, the amount of residual liquid is reduced by making the syringe width $W_B$ narrower. However, if, as shown in Example 11, the syringe width $W_B$ is made too narrow, it turns out that the amount of residual liquid is conversely increased significantly. This is because a shear load arises between the syringe rod and the syringe as the syringe width $W_B$ becomes narrower and the syringe rod cannot crush the swelling portion made of an elastic material of the syringe to the end.

Example 2

The syringe rod width $W_R$ was set to 3.0 mm, the thickness $t_E$ of the swelling portion was set to 0.5 mm, and the syringe width $W_B$ was set to 4.5 mm to satisfy the above formula (1). 200 μL of reagent was injected into the syringe to be fully filled therewith. Then, a test in which an operation to crush the swelling portion made of elastomer (hardness: 60) of the syringe by imposing a load thereon through the syringe rod such that the amount of residual liquid is 5 to 8 μL was repeated 10 times was performed before measuring the load by the syringe rod. The result is shown in FIG. 21B.

As is evident from FIG. 21B, it turns out that the displacement margin can be improved by concentrating on the low load of about 0.6 kgf.

When the tip of the syringe rod 750 is brought into contact with the swelling portion 144 made of an elastic material of the syringe 702 (or 704 or 706 or 708), as described above, the tip is made to pass through the lengthwise groove 164 of the cover plate 60 and the lengthwise groove 154 of the upper plate 50. Among the lengthwise grooves 164 of the cover plate 60, the lengthwise grooves 164 corresponding to the intercalating agent syringe 706 and the second cleaning fluid syringe 708 having a larger volume are provided with the partition 165 in the middle along the length direction of the lengthwise groove 164 as shown in FIG. 10 described above to prevent a finger from entering in the longitudinal direction. Corresponding to the partition 165 in the lengthwise groove 164, as shown in FIG. 22, a slit 751 having a larger width than the partition 165 is provided in the length direction of the syringe rod 750. When the syringe rod 750 as described above is passed through the lengthwise groove 164 of the cover plate 60, the partition 165 passes through the slit 751 of the syringe rod 750 and thus, the syringe rod 750 can be pushed into the swelling portion 144 smoothly.

In an embodiment, as shown in FIG. 23, for example, two protruding portions 753 may be provided along the longitudinal direction of the tip surface of the syringe rod 750. According to the above configuration, when a load is imposed on the swelling portion 144 of the syringe 702 (or 704 or 706 or 708) by the syringe rod 750, the contact area of the syringe rod 750 and the swelling portion 144 can be decreased by the protruding portions 753. As a result, the load on the swelling portion 144 by the syringe rod 750 can be reduced.

In the description above, sending of a sample solution, a first cleaning fluid, an intercalating agent solution, and a second cleaning fluid from the syringes 702, 704, 706, 708 has been described, but in the manufacturing process of the nucleic acid detection cassette 10, when a sample solution, a first cleaning fluid, an intercalating agent solution, or a second cleaning fluid is injected into the syringes 702, 704, 706, 708, the swelling portion 144 of the syringes 702, 704, 706, 708 is crushed and then, when the swelling portion 144 is restored, a negative pressure generated inside the syringes 702, 704, 706, 708 is used to inject the sample solution, first cleaning fluid, intercalating agent solution, or second cleaning fluid into the syringes 702, 704, 706, 708.

(Structure of the Normally Open Valve)

In the amplification unit 80, as described above, the normally open valves 810, 820 are provided on the input port side and the output port side of the amplification channels 812, 816. The normally open valves 810, 820 are constituted by, as shown in FIGS. 24 and 25, the tubular portion 55 being provided in the packing 40 that is flexible inside the rod holes 52, 54 of the upper plate 50. The depression 57 matching with the rod holes 52, 54 of the upper plate 50 is formed in the packing 40 and the tubular portion 55 is arranged inside the depression 57. A cavity portion (channel) for the normally open valves 810, 820 is formed between the tubular portion 55 and the top surface of the lower plate 30 where the tubular portion 55 is arranged and the cavity portion communicatively connect the channel 802, the amplification channel 812 or the amplification channel 816, and the channel 806. As is evident from the above structure, the tubular portion 55 is formed integrally with the packing 40 inside the depression 57 and so is formed sufficiently thinner than the thickness T1 of the packing 40 and preferably thinner than the thickness T2 (T1>T2). Here, the thickness T1 corresponds to the thickness of a convex area of the packing 40 formed from convex areas and concave areas and the thickness T2 corresponds to the thickness of a concave area. Therefore, as shown in FIG. 26, the cavity portion provided inside the tubular portion 55 can be crushed by a rod 59 inserted from outside and the cavity portion can be closed by crushing the tubular portion 55. The channel between the channel 802 and the amplification channel 812 or the channel between the amplification channel 816 and the channel 806 is cut off by the cavity portion being closed. Because the tubular portion 55 is flexible, by retreating the rod 59 after the amplification unit 80 is heated and target DNA inside the sample solution is amplified, the tubular portion 55 that has been crushed can be restored to its original shape like a cavity being formed therein again. Therefore, the channel 802, the amplification channel 812 or the amplification channel 816, and the channel 806 can communicatively connected via the cavity inside the tubular portion 55.

(Structure of the Normally Closed Valve)

Figure 27:
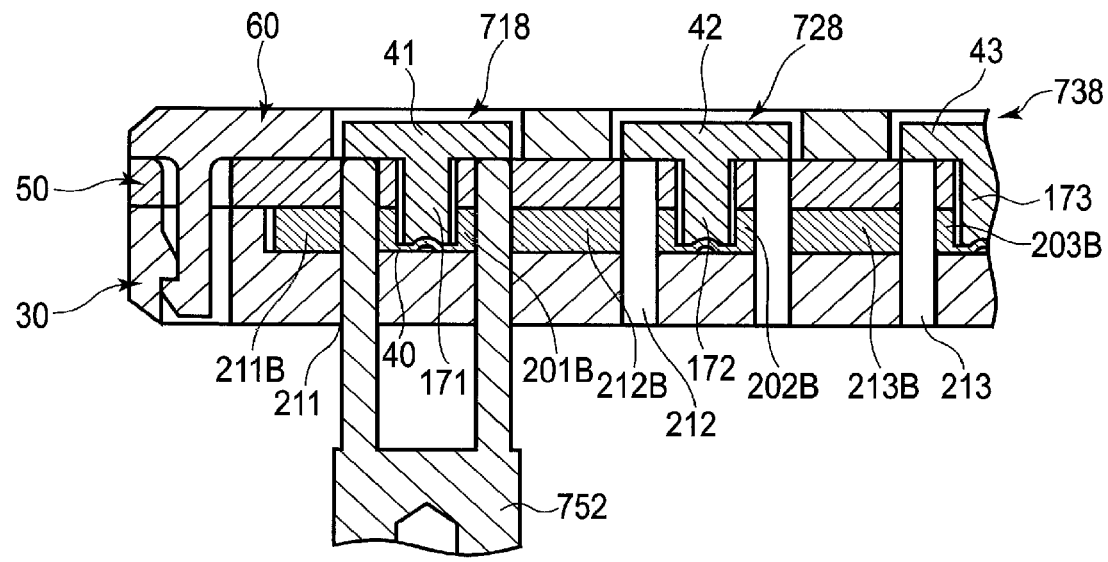
FIG. 27 is a perspective sectional view showing a longitudinal section of the normally closed valve for which an opening operation is performed by the valve rod, the normally closed valve being along the A-A line shown in FIG. 2.

The normally closed valves 718, 728, 738, 748 are configured such that, as described with reference to FIGS. 15 and 16, the tubular portion 55 having a structure similar to that of the normally open valve 810 is closed by the protruding portions 171, 172, 173, 174 provided on the back surface of the cover plate 60 shown in FIG. 12. More specifically, the normally closed valves 718, 728, 738, 748 are configured such that the protruding portions 171, 172, 173, 174 enter a groove provided in the packing 40 via a through hole provided in the upper plate 50 and crush the tubular portion 55 that is flexible in the groove to close the channel of the tubular portion 55. The protruding portions 171, 172, 173, 174 provided on the back surface of the cover plate 60 have, as described above, a base portion pivotally supported and fixed to the cover plate 60 and constitute a cantilever structure notch-supported by the cover plate 60 such that a tongue extending from the base portion is movable. When the normally closed valves 718, 728, 738, 748 are open, as shown in FIG. 27, the tongue of the cantilever structure is lifted by a rod 752 and the protruding portions 171, 172, 173, 174 are removed from the tubular portion so that a channel is secured in the tubular portion 55 for opening. Here, FIG. 26 shows a transverse section of the normally closed valves 718, 728, 738, 748 when the normally closed valve rod 752 is inserted.

Next, the closing and opening operations of the normally closed valves 718, 728, 738, 748 will be described in more detail with reference to FIGS. 27 to 29.

Figure 28:
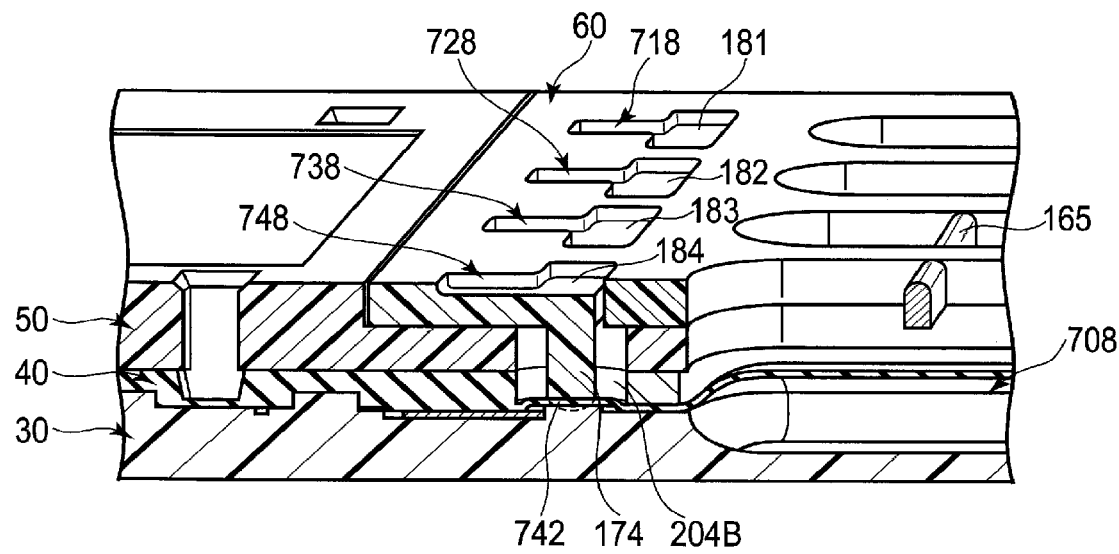
FIG. 28 is a perspective sectional view showing the structure of the normally closed valve shown in FIG. 27 and a longitudinal section of the nucleic acid detection cassette shown in FIG. 2.
Figure 29:
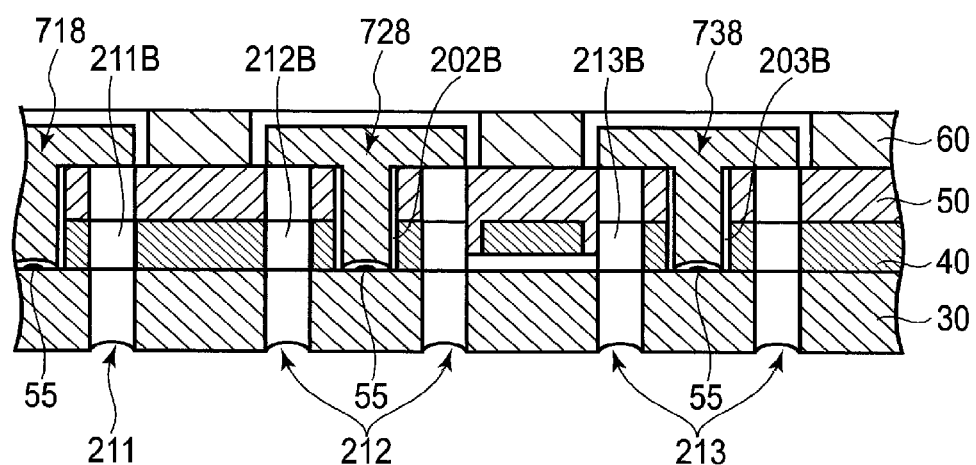
FIG. 29 is a transverse sectional view showing the structure of the normally closed valve shown in FIG. 27.

FIG. 28 is a perspective view schematically showing a portion of the nucleic acid detection cassette as a longitudinal section and FIG. 29 is a perspective view of a transverse section of the normally closed valves 718, 728, 738, 748 along the B-B line in FIG. 9.

The cover plate 60 is provided with, as shown in FIG. 28, the tongues 181, 182, 184, 186 movable along the width direction of the nucleic acid detection cassette 10 and a cantilever structure of the normally closed valves 718, 728, 738, 748 is provided behind these tongues 181, 182, 184, 186. When the cantilever structure is operated to open by the valve rod 752 of the liquid sending control mechanism 16 from the back face side of the cover plate 60, the normally closed valves 718, 728, 738, 748 behind these tongues 181, 182, 184, 186 are opened.

Each of the normally closed valves 718, 728, 738, 748 forms the cantilever structure by the base portion being pivotally supported by the cover plate 60 and the tongues 181, 182, 184, 186 being extended from the base portion. The protruding portions 171, 172, 173, 174 are provided on the back face of the tongues and arranged inside the depressions 201B, 202B, 203B, 204B provided in the packing 40. The tubular portion 55 in a thin film is provided inside the grooves of the packing 40 and a channel is defined between the cavity of the tubular portion and the front surface of the lower plate. When the cover plate 60 is mounted on the upper plate 50, the protruding portions 171, 172, 173, 174 press against the tubular portions 55 from above in respective grooves provided in the packing 40 and the cavity portions therein are crushed to cut off the channel.

Thus, the normally closed valves 718, 728, 738, 748 have the function as normally open valves when not crushed by the protruding portions 171, 172, 173, 174 and the function as normally closed valves is provided when crushed by the protruding portions 171, 172, 173, 174.

The nucleic acid detection cassette 10 in which the syringe 702 is filled with a sample solution or a reagent and whose cap is locked is set up, as shown in FIG. 34, in a testing device. At this point, as shown in FIG. 28, the normally closed valves 718, 728, 738, 748 are closed. When a test is carried out, as shown in FIG. 26, the normally closed valve rod 752 passes through the rod hole 211 to push up the tongues 41, 42, 43 in a T shape above the normally closed valve 718. As a result, as shown in FIG. 15, the tubular portion 55 is opened and the channel between the channel 712 and the channel 802 is opened. Once opened, the normally closed valve 718 is maintained in an open state during the test. The normally closed valves 728, 738, 748 are successively opened according to the test process and when the liquid sending operation is finished, all the normally closed valves 718, 728, 738, 748 are open.

(Structure of the Packing)

Figure 30:
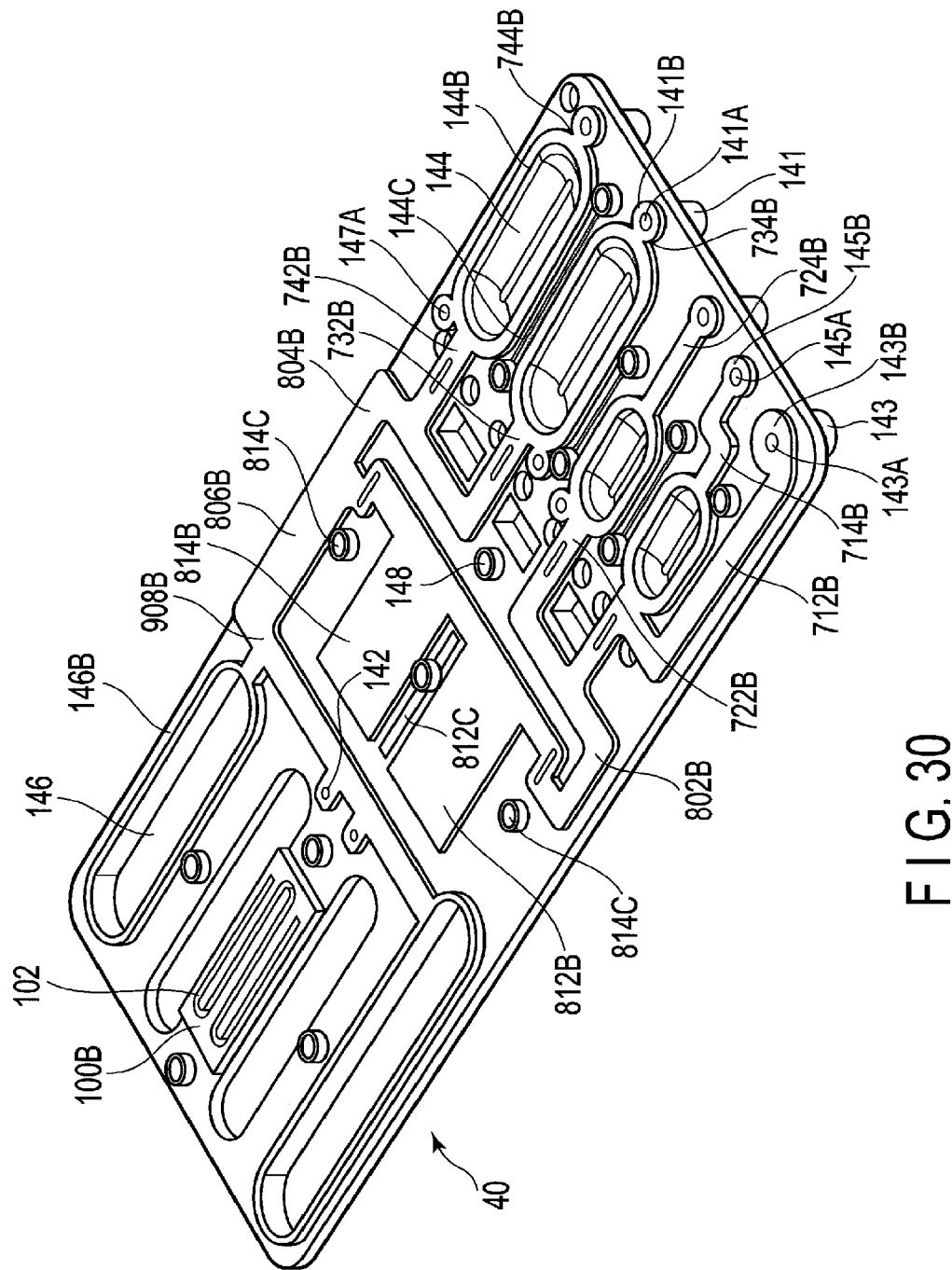
FIG. 30 is a perspective view schematically showing the shape of the back face of packing shown in FIG. 3.

The structure of the packing 40 will be described with reference to FIG. 30. FIG. 30 shows the shape of the back face of the packing 40. On the back face of the packing 40, the swelling portion 144 is shown as a depression and through holes 141A, 143A, 145A, 147A are drilled in locations corresponding to the opening protrusions 141, 143, 145, 147. Also in the packing 40, the insertion hole 148 into which the stud pin 158 provided on the undersurface of the upper plate 50 is inserted is drilled. Then, the back face of the packing 40 is formed in a shape having convex and concave areas (thin-film areas and thick-film areas) corresponding to the channel system. A convex area (thick-film area) on the back face of the packing 40 has a relatively thick thickness T1 and a concave area (thin-film area) between convex areas has a thickness T2 thicker than the thickness T1 (T2>T1). More specifically, a frame portion 144B having the thick thickness T1 is formed on the back face of the packing 40 like surrounding the swelling portion 144 defining the syringes 702, 704, 706, 708. Also ring protruding portions 141B, 143B, 145B, 147B having the thickness T1 are formed around the through holes 141A, 143A, 145A, 147A. Also, a frame portion 146B having the thick thickness T1 is formed around the lengthwise through groove 146 defining the tanks 930, 932 together with the depression 136 of the lower plate 30. Further, zonal areas 712B, 714B, 722B, 724B, 732B, 734B, 742B, 744B, 802B, 804B, 806B, 908B defining the channels 712, 714, 722, 724, 732, 734, 742, 744, 802, 804, 806, 908, 926, with which the groove 132 of the lower plate 30 is brought into close contact are formed so as to have the thick thickness T1. Therefore, the lower plate 30 is brought into close contact with the areas having the thickness T1 fluid-tightly so that fluid-tight sealing of the liquid sending system can reliably be secured.

Also, rectangular areas 812B, 814B of the packing 40 corresponding to the amplification channels 812, 816 of the amplification unit 80 are formed as a flat area in a rectangular shape capable of covering the amplification channels 812, 816 of the amplification unit 80 and the flat area also has the thickness T1 thicker than a thickness T2 of the peripheral area. Therefore, also the amplification channels 812, 816 of the amplification unit 80 formed in the lower plate 30 are fluid-tightly brought into close contact with an area where the lower plate 30 has the thickness T1 so that fluid-tight sealing of the amplification channels 812, 816 can reliably be secured. The fluid-tight sealing can adequately withstand heating of the amplification unit 80.

Further, a pair of U-shaped through grooves 102 connected to each other are formed in a channel forming area 100B of the packing 40 corresponding to the detection channel 100 of the DNA chip 6. The packing 40 is brought into close contact with the a flat substrate of the DNA chip 6 in such a way that the through grooves 102 of the channel forming area 100B of the packing 40 form the detection channel 100 of the DNA chip 6. Here, the packing 40 and the DNA chip 6 are aligned and brought into close contact with each other such that the working electrode 940, the reference electrode 944, and the counter electrodes 946, 948 are arranged inside the groove 102. The channel forming area 100B of the packing 40 similarly has the thickness T1 thicker than the thickness T2 of a peripheral area thereof. Therefore, when the lower plate 30 is brought into close contact with the channel forming area 100B of the packing 40 having the thickness T1, the detection channel 100 can fluid-tightly be formed on the DNA chip 6.

When the upper plate 50 is crimped to the lower plate 30 via the packing 40, the packing 40 that is flexible is deformed, but the thickness change accompanying the deformation is absorbed by an extrusion from a convex area (thick-film area) having the thickness T1 to a concave area (thin-film area) having the thickness T2.

The frame portion 144B defining the syringes 702, 704, 706, 708 has, as described above, the thickness T1, but preferably a slit 144C is formed in an area between the frame portions 144B as cutting penetrating the packing 40. The slit 144C can reliably permit deformation of the packing 40 that is flexible when the upper plate 50 is crimped to the lower plate 30 via the packing 40, absorb and remove distortions generated in the packing 40, and make close contact between the lower plate 30 and the packing 40 more reliable. An area (thin-film area) provided on the outer circumference of the syringes 702, 704, 706, 708 to absorb the thickness change accompanying the deformation of the packing 40 and having the thickness T2 may be cut off and removed if necessary.

Similarly, a slit (cutting) or through holes 812C, 816C are preferably provided between areas 812B, 814B of the packing 40 corresponding to the amplification channels 812, 816 and on both sides thereof. The slit or the through holes 812C, 816C can remove distortions generated in the packing 40 during close contact.

The insertion hole 148 into which the stud pin 158 is inserted is preferably formed to have an inside diameter larger than an outside diameter of the stud pin 158 to absorb the deformation of the packing 40, the circumference thereof is formed in a tubular shape having the thickness T2, and a gap is provided between the outer circumference of the stud pin 158 and the inner surface of the tubular portion. When the upper plate 50 is crimped onto the lower plate 30 by thermal caulking of the stud pin 158, the tubular portion of the insertion hole 148 is deformed and the packing 40 enters the insertion hole 148 so that the gap between the outer circumference of the stud pin 158 and the inner surface of the tubular portion generated during manufacturing is filled with the material of the packing 40. Therefore, the stud pin 158 is reliably held and the upper plate 50 can reliably be fixed to the lower plate 30.

As an example, the thickness T1 of the convex area (thick-film area) described above is defined in the range of 1.0 mm to 3.0 mm and preferably as 1.8 mm if the packing is made of silicon rubber and the thickness T2 of the concave area (thin-film area) is defined in the range of 0.3 mm to 2.0 mm and preferably as 1.0 mm if the packing is made of silicon rubber. Also, if the material of the packing 40 is silicon rubber, the gap between the outer circumference of the stud pin 158 and the inner surface of the tubular portion generated during manufacturing is defined in the range of 0.1 mm to 1.5 mm and preferably as 0.6 mm.

(Assembly of the Nucleic Acid Detection Cassette)

The assembly process of the nucleic acid detection cassette shown in FIG. 2 will be described with reference to FIGS. 31, 32, and 33.

Figure 31:
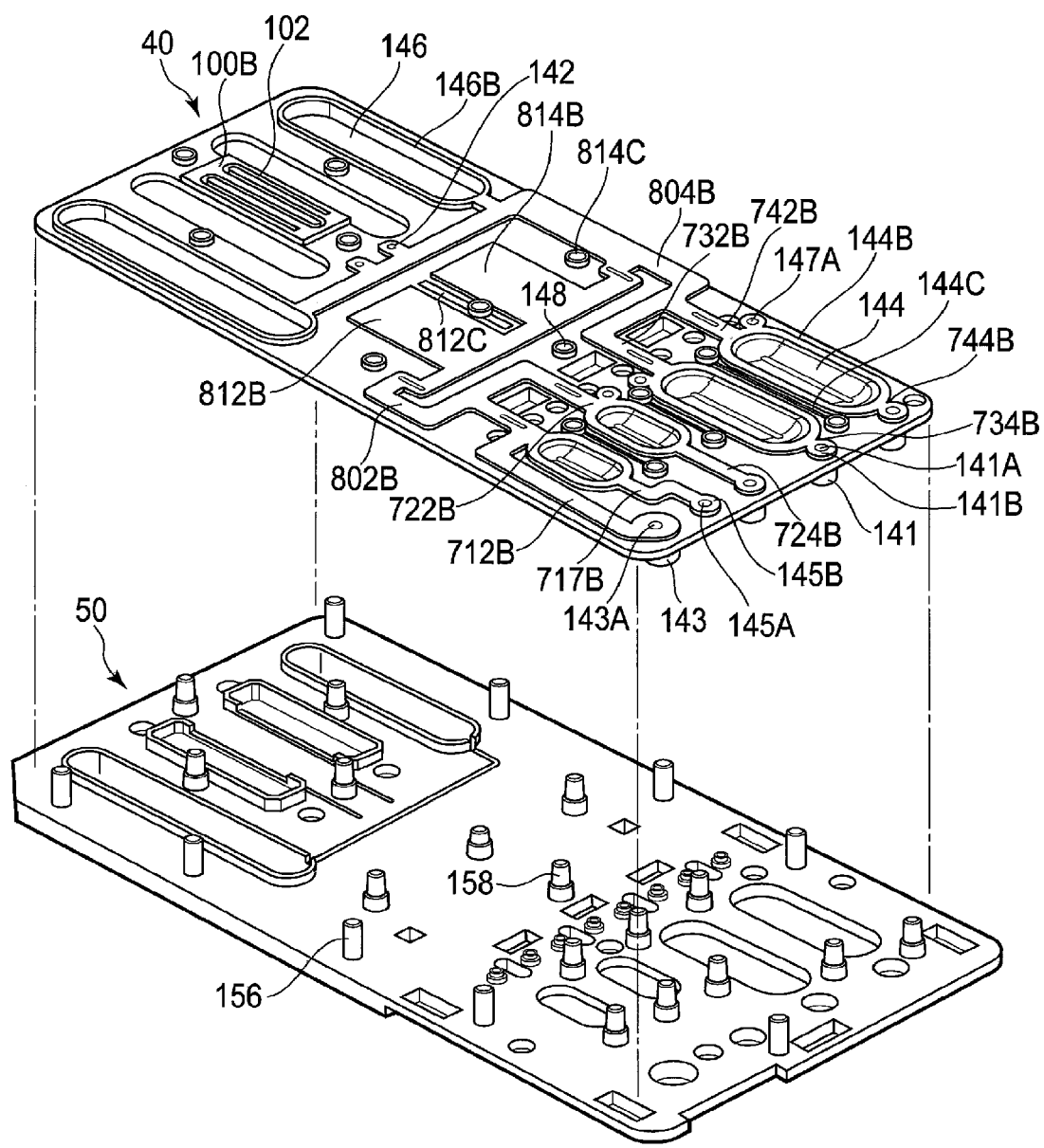
FIG. 31 is a perspective view from a back face side schematically showing an upper plate and the packing of a nucleic acid inspection cassette aligned for assembly shown in FIG. 3.

First, as shown in FIG. 31, the undersurface of the upper plate 50 is directed upward and arranged and the packing 40 to be mounted on the undersurface of the upper plate 50 is prepared. The stud pin 158 provided on the undersurface of the upper plate 50 is inserted into the insertion hole 148 provided in the packing 40 and, as shown in FIG. 31, the packing 40 is placed on the undersurface of the upper plate 50. Here, the stud pin 156 provided on the outer circumference of the upper plate 50 is arranged, as shown in FIG. 32, on the circumference of the packing 40.

Next, the assembly of the upper plate 50 and the packing 40 shown in FIG. 31 is turned upside down and, as shown in FIG. 33, the packing 40 and the upper plate 50 are placed on the lower plate 30 on which the DNA chip 6 is placed. The stud pins 156, 158 of the assembly are inserted into the stud holes 138 of the lower plate 30. Then, by performing thermal caulking of the tip of the stud pins 156, 158 to the lower plate 30, the upper plate 50, the packing 40, and the lower plate 30 are integrated.

(Testing Device)

FIG. 34 shows an internal structure of the testing device into which the nucleic acid detection cassette 10 shown in FIG. 2 is inserted. In the testing device, a heater 850 to heat the amplification unit 80 and a Peltier device 852 to maintain the detection channel 100 of the DNA chip 6 at a reaction temperature are provided in the back face side of the nucleic acid detection cassette 10 that has been inserted so as to be movable up and down indicated by arrows by lift mechanisms 854, 856 respectively. The heater 850, the Peltier device 852, and the lift mechanisms 854, 856 constitute the temperature control mechanism 14 shown in FIG. 1.

Also, a current probe 960 that fetches a detection current by being electrically connected to electrode pads of the electrode pad areas 110, 112 of the DNA chip 6 is provided on the top surface side of the nucleic acid detection cassette 10 so as to be movable up and down. The current probe 960 is electrically connected to a circuit board 962 including a processor for signal processing and constitutes the measuring unit 12 shown in FIG. 1.

Further, the syringe rod 750 to send a sample solution, a cleaning fluid, or an intercalating agent solution from the syringes 702, 704, 706, 708 is provided in the top surface side of the nucleic acid detection cassette 10 and also the normally open valve rod 59 to close the normally open valves 810, 820 is provided. A normally closed valve rod 752 to open the normally closed valves 718, 728, 738, 748 is provided on the undersurface side of the nucleic acid detection cassette 10. The syringe rod 750, the normally open valve rod 59, and the normally closed valve rod 752 constitute the liquid sending control mechanism 16.

Figure 36:
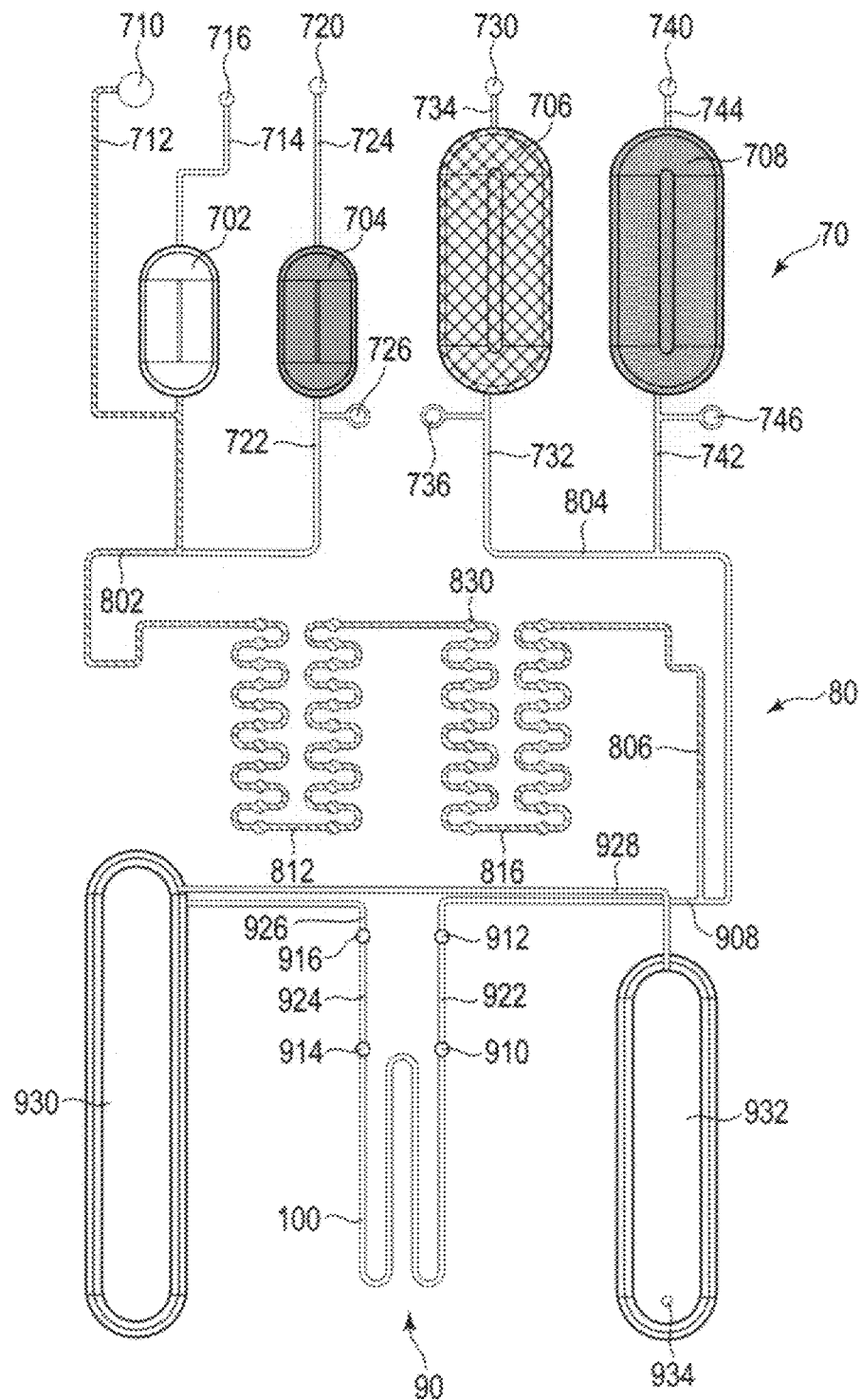
FIG. 36 is a plan view schematically showing the supply of a sample solution to the amplification unit inside the nucleic acid detection cassette shown in FIG. 4.

Each unit constituting the measuring unit 12, the temperature control mechanism 14, and the liquid sending control mechanism 16 is controlled by a program stored in the controller 18 and, as shown in FIG. 36, an electrochemical test of a sample is performed.

(Electrochemical Test of a Sample)

An electrochemical test of a sample by the nucleic acid testing device shown in FIG. 1 will be described with reference to the flowchart shown in FIG. 35 and a liquid sending operation shown in FIGS. 36 to 39.

When the nucleic acid detection cassette 10 is manufactured, the first cleaning fluid syringe 704 is filled with a first cleaning fluid, the intercalating agent syringe 706 is filled with an intercalating agent solution, and the second cleaning fluid syringe 708 with a second cleaning fluid to prepare the nucleic acid detection cassette 10. Then, the user (operator) injects a sample solution into the sample syringe 702. Then, the nucleic acid detection cassette 10 is inserted into the nucleic acid testing device 8 to start a test (step S10). To inject a sample solution into the sample syringe 702, the user (operator) grips the nucleic acid detection cassette 10 and injects the sample solution into the sample injection port 710 using a micro-syringe or a medical syringe. When the injection of the sample solution into the sample syringe 702 is completed, the cap 20 is mounted on the nucleic acid detection cassette 10. By mounting the cap 20 on the nucleic acid detection cassette 10 unremovably, the sample injection port 710 and the air vent opening 716 are closed.

After the nucleic acid detection cassette 10 is inserted into the testing device 8, the current probe 960 is descended toward the nucleic acid detection cassette 10 and brought into electric contact with the electrode pad 942 in the electrode pad areas 110, 112 of the DNA chip 6 so that a reaction current in the detection channel 100 can be detected.

When the test is started, first the normally closed valve rod 752 is communicatively connected to the sample syringe 702 and pressed against the normally closed valve 718 to open the normally closed valve 718. Then, the sample syringe 702 is crushed by the syringe rod 750 and the sample solution inside is supplied, as shown in FIG. 36, to the amplification channels 812, 816 via the channel 802 (step S12). When the amplification channels 812, 816 are fully filled with the sample solution, the normally open valve rod 59 crushes the normally open valves 810, 820 to close the rod holes 52, 54. Also, the heater 850 is pressed against the amplification unit 80 of the nucleic acid detection cassette 10 so that the amplification channels 812, 816 of the amplification unit 80 are heated by the heater and maintained at a constant temperature. Therefore, in the amplification channels 812, 816 that are closed, a plurality of types of target DNA contained in the sample solution is multi-amplified by a plurality of corresponding types of primer sets released from the wall surface of the amplification channels 812, 816 (step S14).

Figure 37:
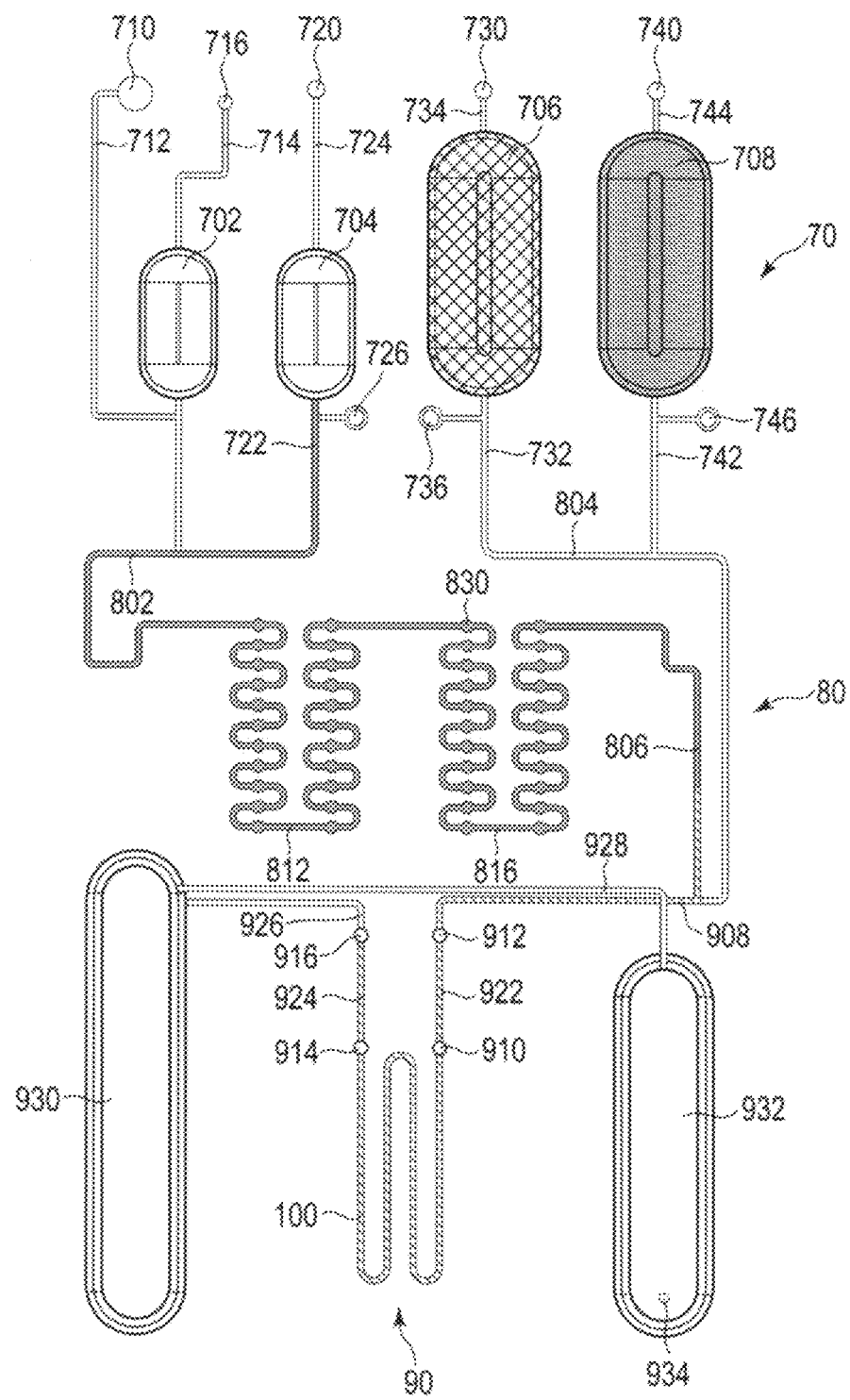
FIG. 37 is a plan view schematically showing the supply of a first cleaning fluid to the amplification unit and the supply of a sample solution to a detection unit inside the nucleic acid detection cassette shown in FIG. 4.

Next, the normally open valve rod 59 moves away from the normally open valves 810, 820 and returns to its original position to open the normally open valves 810, 820 again. Subsequently, the normally closed valve rod 752 is pressed against the normally closed valve 728 communicatively connected to the first cleaning fluid syringe 704 to open the normally closed valve 728. Then, the first cleaning fluid syringe 704 is crushed by the syringe rod 750 and, as shown in FIG. 37, the first cleaning fluid inside is supplied to the amplification channels 812, 816 via the channel 802. At this point, the sample solution containing amplification products inside the amplification channels 812, 816 is supplied to the detection channel 100 of the detection unit 90 via the channels 806, 908, 922 (step S16). Here, the first cleaning fluid sends the sample solution containing amplification products from the amplification channels 812, 816 to the detection channel 100 by pushing out the air inside the channel 722. Therefore, the sample solution containing amplification products and the first cleaning fluid are in contact via an air layer and are sent through the channel 802 and the amplification channels 812, 816 without mixing with each other.

When the sample solution containing amplification products is sent to the detection channel 100, the Peltier device 852 of the nucleic acid testing device 8 is lifted toward the nucleic acid detection cassette 10 to come into contact with the detection unit 90. Then, the detection channel 100 is controlled by the Peltier device 852 to a temperature optimal for the hybridization reaction. In the detection channel 100, target DNA contained in amplification products in the sample solution is bound to a nucleic acid probe through hybridization (step S18). Then, the normally closed valve rod 752 is pressed against the normally closed valve 748 communicatively connected to the second cleaning fluid syringe 708 to open the normally closed valve 748. Then, the second cleaning fluid syringe 708 is crushed by the syringe rod 750 and, as shown in FIG. 38, the second cleaning fluid inside is supplied to the detection channel 100 via the channels 804, 908, 922 (step S20). Thus, a sample solution containing unreacted DNA that is not hybridized in the detection channel 100 is sent from the detection channel 100 to the waste liquid tank 930 via the channels 924, 926. Here, the detection channel 100 is controlled by the Peltier device 852 to a temperature optimal for cleaning and the inside of the detection channel 100 is cleaned (step S22).

When the second cleaning fluid is supplied to the channel 804, the second cleaning fluid pushes out the sample solution via an air layer. Here, while the channel 804 and the channel 806 are communicatively connected each other by the channel 908, a liquid sending pressure is added to the channel 804 and the channel 908 via the air layer and a back sending pressure is added to the channel 806 via the air layer. Therefore, the second cleaning fluid is supplied to the detection channel 100 and the sample solution is sent from the detection channel 100 to the waste liquid tank 930 without the first cleaning fluid being mixed into the second cleaning fluid.

Figure 39:
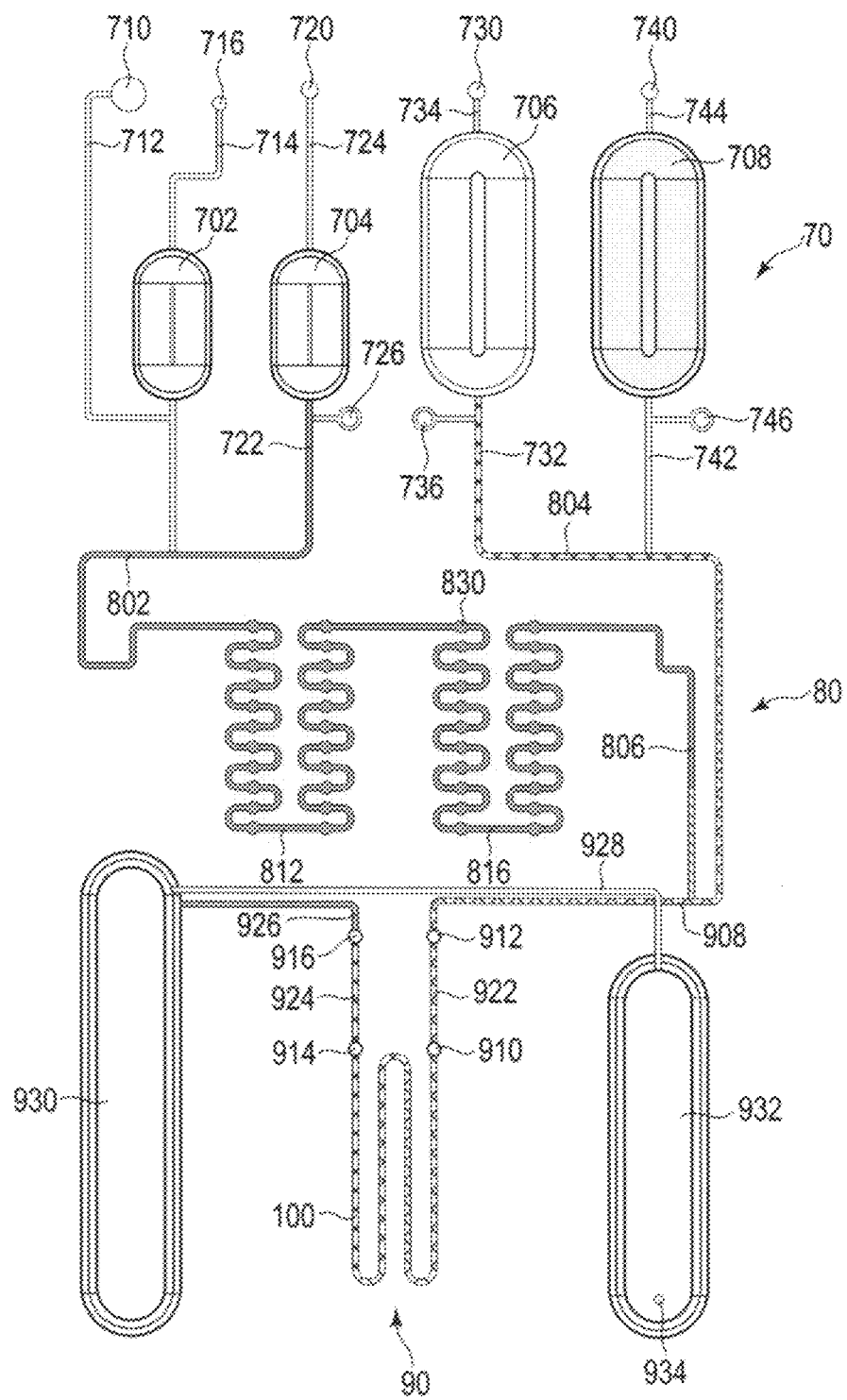
FIG. 39 is a plan view schematically showing the supply of an intercalating agent solution to the detection unit inside the nucleic acid detection cassette shown in FIG. 4.

When cleaning is finished, the normally closed valve rod 752 is pressed against the normally closed valve 738 communicatively connected to the intercalating agent syringe 706 to open the normally closed valve 738. Then, the intercalating agent syringe 706 is crushed by the syringe rod 750 and, as shown in FIG. 39, the intercalating agent solution inside is supplied to the detection channel 100 via the channels 804, 908, 922 (step S24). Here, a liquid sending pressure is added to the channel 804 and the channel 908 via the air layer and a back sending pressure is added to the channel 806 via the air layer. Therefore, the intercalating agent solution is supplied to the detection channel 100 without the first cleaning fluid being mixed into the intercalating agent solution. The second cleaning fluid in the detection channel 100 is sent from the detection channel 100 to the waste liquid tank 930 via the channels 924, 926.

After the intercalating agent solution is supplied to the detection channel 100, the detection channel 100 is controlled by the Peltier device 852 to a temperature optimal for intercalating agent reaction to cause the intercalating agent reaction in the detection channel 100 (step S26). In the intercalating agent reaction, for example, after a double strand portion is recognized by the intercalating agent, the intercalating agent enters the recognized double strand portion and the double strand portion is electrochemically activated to generate an electric signal. The intercalating agent reaction is detected by the current probe 960 via the electrode pad 942 in the electrode pad areas 110, 112 of the DNA chip 6 while a voltage is applied (step S28). A measured current detected by the current probe 960 is processed by the processor of the circuit board 962 and sent to the computer 4 as measured data for analysis.

According to an embodiment, as described above, a nucleic acid detection cassette that can be used by a nucleic acid testing device highly integrated and completely automated from amplification of a sample to detection of an electrochemical reaction of the sample can be provided.

(Volumes of the Amplification Unit and the Detection Unit)

The relationship between the volume of the amplification unit 80 and that of the detection unit 90 will be described with reference to FIGS. 40A to 41B.

FIG. 40A is a plan view schematically showing a channel model of a nucleic acid detector from the amplification unit 80 to the detection unit 90 and FIG. 40B is a cross section obtained by cutting the channel model of the nucleic acid detector shown in FIG. 40A along a line E-E. A nucleic acid detector 91 according to the channel model includes a detector body 92, a channel 93 formed therein, the amplification unit 80 including the primer set 832 immobilized on the inner wall of the channel, and the detection unit 90 including a nucleic acid probe 955 immobilized on the inner wall of the channel downstream of the amplification unit 80. Both ends of the channel 93 open to the outside of the detector body 92.

Such a nucleic acid detector can amplify a plurality of types of nucleic acid simultaneously or in parallel and detect a plurality of types of target DNA in obtained amplification products simultaneously or in parallel.

To detect, for example, n types of target nucleic acid, n types of primer sets to amplify each type of target nucleic acid specifically are prepared. n types of primer sets, that is, a primer set 832(1), . . . , a primer set 832(n) are immobilized in a primer immobilization area 830(1), . . . , a primer immobilization area 830(n) for each type respectively. n types of nucleic acid probes, each of which containing a sequence capable of specifically hybridizing with a plurality of types of amplification products produced by amplification caused by primer sets or a portion thereof, are prepared. These n types of nucleic acid probes, that is, a nucleic acid probe 955(1), . . . , a nucleic acid probe 955(n) are immobilized in n nucleic acid probe immobilization areas, that is, a nucleic acid probe immobilization area 950(1), . . . , a nucleic acid probe immobilization area 950(n) for each type. Here, n is an integer equal to 2 or greater.

The nucleic acid detector 91 according to such an embodiment has the first to n-th primer sets of mutually different types immobilized on the inner wall of a channel as the primer sets and the first to n-th nucleic acid probes of mutually different types immobilized on the inner wall of a channel as the nucleic acid probes.

Here, the amplification unit 80 is an area including all of the primer set immobilization areas 830(1) to 830(n). The detection unit 90 is an area including all of the nucleic acid probe immobilization areas 950(1) to 950(n).

In order to detect all of amplification products amplified by each of n types of primer sets in the amplification unit 80 simultaneously or in parallel, the relationship between the volume of the amplification unit 80 and that of the detection unit 90 is as described below.

That is, if the volume of the amplification unit 80 is Va, the volume of the detection unit 90 is Vd, the standard deviation of a volume difference between the amplification unit 80 and the detection unit 90 is $\sigma_V$, the standard deviation of a liquid sending amount from the amplification unit 80 and the detection unit 90 is $\sigma_Q$, the cross-sectional area of a specific area of a relevant channel continuously extending upstream and downstream of the detection unit 90 is B, and the reaching limit distance of amplification products is L, the relationship between the volume of the amplification unit 80 and that of the detection unit 90 satisfies the following formula:

$$(Vd+\Delta V_2) > Va > (Vd+\Delta V_1)$$

$$\Delta V_1 = 3(2\sigma_Q + \sigma_V)$$

$$\Delta V_2 = 2BL - 3(2\sigma_Q + \sigma_V)$$

Regarding the construction of the above formula, the lower limit and the upper limit will be described with reference to FIGS. 41A and 41B.

For the lower limit, as shown in FIGS. 41A and 41B, one condition of the amplification unit volume (Va) and the detection unit volume (Vd) is that the amplification unit volume is larger than the detection unit volume. In this case, the difference between the amplification unit volume the detection unit volume is present as ΔVu and ΔVl on the upstream side and the downstream side respectively. That is, $$\Delta V_1 = Va - Vd = \Delta Vu + \Delta Vl$$

holds. Then, ideally $$\Delta Vu = \Delta Vl = \Delta V_1/2$$

holds.

If the standard deviation of the volume difference is $\sigma_V$ and the standard deviation of the liquid sending amount is $\sigma_Q$, the following formula is derived from the viewpoint of quality:

$$(\Delta V_1 - 3\sigma_V)/2 > 3\sigma_Q, \text{ that is,}$$

$$\Delta V_1 > 3(3\sigma_Q + \sigma_V)$$

On the other hand, as shown in FIGS. 41A and 41B, the upper limit is determined as described below. The liquid for an amplification unit volume exceeding the detection unit volume spreads in a specific range upstream and downstream of the detection unit 90, that is, in a channel across an area wider than the detection unit area arranged in the channel when the liquid contained in the amplification unit 80 is sent to the detection unit 90. In this case, the area where a liquid spreading upstream or downstream of the detection unit 90 is present is an area outside the detection unit provided in the channel. That is, when the liquid contained in the amplification unit 80 and subjected to an amplification reaction is sent to the detection unit 90 after the amplification reaction, the liquid is contained in the channel corresponding to the detection unit 90 and at the same time, an excessive liquid reaches a specific area upstream and downstream of the detection unit 90 (specific area outside the detection unit) in the channel that continues from the detection unit 90. Here, the range to which amplification products can be sent is, among areas upstream and downstream of the detection unit 90, a range in which amplification products sent to the area thereof can reach the detection unit 90 by diffusion or convection.

Information about amplification products produced by the amplification unit 80 can be detected by the detection unit 90 by amplification products being sent to such a range. That is, amplification products sent to an area outside the detection unit are moved to the detection unit 90 by diffusion or convection.

Such a specific area outside the detection unit only needs to be a range in which amplification products can reach the detection unit 90 by diffusion or convection and can be defined by the cross-sectional area B of the channel defining a specific area continuous to the detection unit 90 and outside the detection unit and the reaching limit distance L.

Therefore, if the cross-sectional area of the channel continuously extending upstream and downstream of the detection unit 90 is B and the reaching limit distance is L, the upper limit of the difference between the amplification unit volume and the detection unit volume is $\Delta V_2$ and $\Delta V_2$ is given by $\{2BL - 3(2\sigma_Q + \sigma_V)\}$.

In FIGS. 41A and 41B, the relationship between the volume of the amplification unit 80, the volume of the detection unit 90, an area 90A outside the detection unit 90 of the channel extending upstream of the detection unit 90, and an area 90B outside the detection unit 90 of the channel extending downstream of the detection unit 90 is shown as conceptual diagrams. In the area 90A and the area 90B, a liquid that cannot be contained in the channel corresponding to the detection unit 90 of the liquid sent from the amplification unit 80 to the detection unit 90 is accommodated. Amplification products contained in the above portion can be detected by the detection unit 90 by the amplification unit and the detection unit being designed to satisfy the above conditions.

The upper limit and the lower limit are both represented by the standard deviation of the difference between the detection unit volume and the amplification unit volume normally distributed among a plurality of nucleic acid detectors. In FIGS. 41A and 41B, ($\sigma_Q + \sigma_V$) as a value that defines the normal distribution, the standard deviation, and the pertinent conditions is denoted as "a" to represent the volume difference between the amplification unit 80 and the detection unit 90 as a conceptual diagram showing an intuitive image.

Therefore, the amplification unit volume Va is larger than the detection unit volume Vd at most by $\{2BL - 3(2\sigma_Q + \sigma_V)\}$. In other words, the amplification unit volume Va is larger than the detection unit volume Vd and the difference therebetween is less than $\{2BL - 3(2\sigma_Q + \sigma_V)\}$.

Here, if the standard deviation of the volume difference is $\sigma_V$ and the standard deviation of the liquid sending amount is $\sigma_Q$, the following formula is derived from the value of "2BL" as a volume permitted when the upstream side and the downstream side of the detection unit are combined and from the viewpoint of quality:

$$\Delta V_2 = 2BL - 3(2\sigma_Q + \sigma_V)$$

The relationship between the volume of the amplification unit 80 and the volume of the detection unit 90, that is, an element about the volume and further, the capacity of the liquid sending mechanism and variations of the capacity of channels other than the amplification unit 80 and the volume of the detection unit 90, that is, an element about the position are controlled by the above formula being satisfied by the nucleic acid amplification detector. Accordingly, in one device, nucleic acid can be amplified and amplification products produced therein can be detected.

If the volume of the amplification unit 80 is smaller than that of the detection unit 90 in a range in which the above relationship is not satisfied, a plurality of types of amplification products and all nucleic acid probes corresponding thereto are prevented from detectably encountering the detection unit 90, which is not very preferable. If the volume of the amplification unit 80 is larger than that of the detection unit 90 in a range in which the above relationship is not satisfied, also in this case, a plurality of types of amplification products and all nucleic acid probes corresponding thereto are prevented from detectably encountering the detection unit 90, which is not very preferable.

In such a nucleic acid detector, variations in terms of manufacturing may arise. Also, variations of capacity may individually arise in the liquid sending mechanism or channels other than the amplification unit 80 and the detection unit 90. Such variations may affect the relationship between the volume of the amplification unit 80 and that of the detection unit 90. In the above formula, variations in terms of manufacturing and variations of capacity of individual channels are taken into consideration. Therefore, by satisfying the above formula, amplification products produced by the amplification unit 80 in such a nucleic acid detector are all subjected to a reaction with a nucleic acid probe in the detection unit 90.

By considering the standard deviation of the liquid sending amount, the relationship between the center in the length direction of the amplification unit and the center in the length direction of the detection unit determined along the axis in the flow direction of the channel. Accordingly, the liquid positioned in the center in the length direction of the amplification unit moves to a position approximately matching the center in the length direction of the detection unit after liquid sending. In this case, the liquid position may slightly deviate without perfectly matching the center of the amplification unit or the center of the detection unit, but the magnitude of deviation may be within the range permitted for comprehensive detection of amplification products sent to the detection unit throughout the detection unit.

In a preferable embodiment, a plurality of types of primer sets and a plurality of types of nucleic acid probes immobilized on the inner wall of the channel have the immobilization position in the amplification unit 80 and the immobilization position in the detection unit 90 corresponding to each other. That is, the first amplification product produced by the first primer set immobilized most upstream of the amplification unit 80 is configured to be detected by the first nucleic acid probe immobilized most upstream of the detection unit 90. Then, the n-th amplification product produced by the n-th primer set immobilized most downstream of the amplification unit 80 is configured to be detected by the n-th nucleic acid probe immobilized most downstream of the detection unit 90. That is, the order of immobilization of primer sets immobilized in the amplification unit 80 from upstream to downstream and the order of immobilization of nucleic acid probes to detect each amplification product produced by each primer set immobilized in the detection unit 90 from upstream to downstream preferably correspond to each other. To put still another way, the position of the area where the primer set to amplify specific target nucleic acid is immobilized in the amplification unit 80 can be indicated as a ranking when the area immobilized in the amplification unit 80 is counted from upstream, which is equal to the ranking of the area where the nucleic acid probe to detect the specific target nucleic acid is immobilized when nucleic acid probes immobilized in the detection unit 90 are counted from upstream. However, for a combination that is not preferable to be adjacent to each other due to interactions between sequences, it is important to attain an order in which amplification and detection are done suitably by interchanging such sequences.

In the nucleic acid detector configured as described above, an amplification product produced by a specific primer set in a specific position of the amplification unit 80 can reach the corresponding position when sent to the detection unit 90 with a certain level of precision, that is, with precision to the extent that target nucleic acid to be detected can be detected by the above formula being satisfied by the relationship of volumes of the amplification unit 80 and the detection unit 90 and requirements of positions. Accordingly, any of amplification products produced based on target nucleic acid to be amplified by all primer sets immobilized in the amplification unit 80 can react with the corresponding nucleic acid probe in the detection unit 90 with a certain level of precision.

The detector body included in the nucleic acid detector according to an embodiment may be made of a material allowing an amplification reaction therein and may be a material arbitrarily selected from, for example, silicon, glass, resin, and metal. The detector body may be an approximate rectangular parallelepiped, an approximate cube, a flat rectangular parallelepiped, or a flat and lengthwise rectangular parallelepiped or a rod-shaped body, a plate-shaped body, or a laminated body in which such bodies are stacked. A channel may be formed inside the detector body in such a ground form by any one of methods.

For example, in the nucleic acid detector according to an embodiment, the detector body may include, in addition to the channel, a plurality of syringes that stores a sample solution or an intercalating agent solution, a first channel that connects, among the plurality of syringes, a syringe that stores the sample solution, and the amplification unit and the detection unit, and a second channel that connects, among the plurality of syringes, a syringe that stores the intercalating agent solution.

In the nucleic acid detector according to an embodiment, the detector body may be a laminated structure including an upper plate made of a rigid material, packing made of an elastic material, and a lower plate made of a rigid material that seals the packing together with the upper plate.

Further, in the nucleic acid detector according to an embodiment, the amplification unit may include a plurality of wells in which wells adjacent to each other are connected by an interval channel and which have a width larger than that of the interval channel so that a plurality of types of primer sets may be immobilized inside the wells for each type.

Example 3, Calculation of the Lower Limit (1) Standard Deviation of the Volume Difference 10 units of the nucleic acid detection cassette according to an embodiment shown in FIGS. 41A and 41B were produced. The volume of the amplification unit and the volume of the detection unit of each of these nucleic acid detection cassettes were measured.

For each of the 10 nucleic acid detection cassettes, the difference between the volume of the amplification unit and the volume of the detection unit obtained as described above was determined. The standard deviation of the volume difference between the amplification unit and the detection unit was determined for the 10 nucleic acid detection cassettes obtained as described above.

As a result, the standard deviation ($\sigma_V$) of the volume difference was 0.8 µL.

(2) Standard Deviation of the Liquid Sending Amount

The liquid sending amounts other than the amplification unit and the detection unit of the 10 nucleic acid detection cassettes in (1) described above were measured. The standard deviation of the liquid sending amount obtained for each of the 10 nucleic acid detection cassettes was determined.

As a result, the standard deviation ($\sigma_Q$) of the liquid sending amount was 1.6 µL.

(3) Relationship of Volumes of the Amplification Unit and the Detection Unit $\Delta V_1$ was determined by substituting results of (1) and (2) described above into the following formula:

$$(\Delta V_1 - 3\sigma_V)/2 > 3\sigma_Q$$

$$\Delta V_1 > 3(2\sigma_Q + \sigma^V)$$

$$\Delta V_1 > 3 \times (2 \times 1.6 + 0.8)$$

$$\Delta V_1 > 12$$

From the above results, it becomes clear that it is necessary to make the volume of the amplification unit larger than the volume of the detection unit by exceeding 12 µL in a nucleic acid detection cassette produced as an embodiment shown in FIGS. 41A and 41B. In other words, in a nucleic acid detection cassette produced as an embodiment shown in FIGS. 41A and 41B, it becomes clear that the difference between the volume of the amplification unit and the volume of the detection unit needs to be larger by exceeding 12 μL.

Example 4, Calculation of the Upper Limit 10 units of the nucleic acid detection cassette according to an embodiment shown in FIGS. 41A and 41B were produced. The cross-sectional area (B) and the reaching limit distance (L) of the channel continuously extending upstream and downstream of the detection unit of each of the nucleic acid detection cassettes were measured.

As a result, the cross-sectional area (B) was 0.49 mm² and the reaching limit distance (L) was 40 mm. Also, the standard deviation ($\sigma_V$) of the volume difference between the amplification unit and the detection unit was 0.8 μL and the standard deviation ($\sigma_Q$) of the liquid sending amount was 1.6 μL.

$\Delta V_2$ was determined by substituting the above results into the following formula:

$\Delta V_2 < 2BL - 3(2\sigma Q + \sigma_V)$ $\Delta V_2 < 2 \times 0.49 \times 40 - 3(2 \times 1.6 + 0.8)$ $\Delta V_2 < 39.2 - 12$ $\Delta V_2 < 27.2$ From the above results, it becomes clear that it is necessary to make the volume of the amplification unit larger than the volume of the detection unit in a range less than 27.2 μL in a nucleic acid detection cassette produced as an embodiment shown in FIGS. 41A and 41B. In other words, in a nucleic acid detection cassette produced as an embodiment shown in FIGS. 41A and 41B, it becomes clear that the difference between the volume of the amplification unit and the volume of the detection unit needs to be in a range less than 27.2 μL.

By using such a nucleic acid detection cassette, it becomes possible to amplify a plurality of nucleic acid simultaneously or in parallel and to detect a plurality of types of target nucleic acid in the obtained amplification products simultaneously or in parallel.

Example 5, Design of the Nucleic Acid Detection Cassette from Target Nucleic Acid to be Detected Assuming that 40 types of DNA fragments are detected as target nucleic acid, the nucleic acid detection cassette shown in FIGS. 41A and 41B was designed. In this case, 40 pairs of primer sets are needed to amplify all DNA fragments. Here, to prevent amplification inhibition due to interactions of primer sets, the distance between spots where primers are arranged was designed to be separated by 4 mm or more.

Here, the cross section of the channel of the produced nucleic acid detection cassette is 0.7 mm×0.7 mm and the volume of the amplification unit is about 60 μL. The standard deviation $\sigma_V$ of the volume difference between the amplification unit and the detection unit and the standard deviation $\sigma_Q$ of the liquid sending amount are 0.8 μL, and 1.6 μL respectively. The volume of the amplification unit is set to about 60 μL. In this case, therefore, the volume of the detection unit was designed so as to be smaller than the volume of the amplification unit of about 60 μL by exceeding 12 μL.

The upper limit of the detection unit in the nucleic acid detection cassette in (1) described above was designed as described below. Because the cross-sectional area was 0.49 mm², the reaching limit distance was 40 mm, the standard deviation of the volume difference between the amplification unit and the detection unit was 0.8 μL, and the standard deviation of the liquid sending amount was 1.6 μL, $\Delta V_2$ was 27.2 μL. Therefore, the volume of the detection unit was designed so as not to be smaller than the volume of the amplification unit of about 60 μL by exceeding 27.2 μL. In other words, the volume of the amplification unit was made larger than the volume of the detection unit and the difference therebetween was set to be less than 27.2 μL.

By using such a nucleic acid detection cassette, it becomes possible to amplify a plurality of nucleic acid simultaneously or in parallel and to detect a plurality of types of target nucleic acid in the obtained amplification products simultaneously or in parallel.

Example 6. Nucleic Acid Detection Test

A nucleic acid detection cassette according to an embodiment shown in FIGS. 41A and 41B was produced. A nucleic acid detection test was performed using the nucleic acid detection cassette.

1. Preparation of the Nucleic Acid Detection Cassette
1-1. Preparation of the DNA Chip First, nine types of nucleic acid probes having mutually different base sequences were prepared. Probe names of these probes are a nucleic acid probe A, a nucleic acid probe B, a nucleic acid probe C, a nucleic acid probe D, a nucleic acid probe E, a nucleic acid probe F, a nucleic acid probe G, a nucleic acid probe H, and a nucleic acid probe I and the base sequences of these nucleic acid probes are shown in Table 2.

TABLE 2

| Nucleic acid probe | | |
|---|---|---|
| Probe name | Sequence | Number of bases |
| A (SEQ ID NO: 1) | ACAAGGTCATAATAATGGTATTTGTTGGGGCAATC | 35 |
| B (SEQ ID NO: 2) | TGGTCCTGGCACTGATAATAGGGAATGTATATCAA TGGATTATAAACAAACACAA | 55 |
| C (SEQ ID NO: 3) | TTGTAACCAGTACGGTTTATTAAATAATTGGGATT CTGAGG | 41 |
| D (SEQ ID NO: 4) | AGTACTGCTACAGAACAGTTAAGTAAATATGATGC ACGAAAAATTAATCAGTACC | 55 |
| E (SEQ ID NO: 5) | GCCCCGACCGATTTCAACACCTACACAGGCCCAGA CCAAGCGT | 43 |
| F (SEQ ID NO: 6) | AGCTACAGCTGTTATTACGCAGGATGTTAGGGATA ATGTGTCAGTTGATTATAAG | 55 |
| G (SEQ ID NO: 7) | ACCAATAAGGTTTATTGAATATTTGGGCATCAGA | 34 |
| H (SEQ ID NO: 8) | ATTATCTACCTCTATAGAGTCTTCCATACCTTCTA CATATGATCCTTCTAAGTTT | 55 |

TABLE 2-continued

Nucleic acid probe

| Probe name | Sequence | Number of bases |
|---|---|---|
| I (SEQ ID NO: 9) | CTTTAATATAAAGGTCATCCGGGACAGCCTCGCCAAGTTTT | 41 |

These nine types of nucleic acid probes were immobilized on each electrode arranged on a substrate for DNA chip to detect nucleic acid. More specifically, nucleic acid probes were immobilized as described below. A probe DNA solution containing 3 μM of each of the nucleic acid probe A, the nucleic acid probe B, the nucleic acid probe C, the nucleic acid probe D, the nucleic acid probe E, the nucleic acid probe F, the nucleic acid probe G, the nucleic acid probe H, and the nucleic acid probe I was prepared. 100 nL of the probe DNA solution was spotted on each working electrode. Three working electrodes were allocated to each nucleic acid probe (see Table 3). Then, these working electrode were dried at 40° C. Accordingly, nucleic acid probes were fixed to the electrodes on the chip substrate to obtain a DNA chip. Here, the nucleic acid probe G is a nucleic acid probe for negative control.

TABLE 3

Electrode allocation

| Electrode | Purpose | Immobilized nucleic acid probe |
|---|---|---|
| 1st electrode | Gene A detection | Nucleic acid probe A |
| 2nd electrode | | |
| 3rd electrode | | |
| 4th electrode | Gene B detection | Nucleic acid probe B |
| 5th electrode | | |
| 6th electrode | | |

TABLE 3-continued

Electrode allocation

| Electrode | Purpose | Immobilized nucleic acid probe |
|---|---|---|
| 7th electrode | Gene C detection | Nucleic acid probe C |
| 8th electrode | | |
| 9th electrode | | |
| 10th electrode | Gene D detection | Nucleic acid probe D |
| 11th electrode | | |
| 12th electrode | | |
| 13th electrode | Gene E detection | Nucleic acid probe E |
| 14th electrode | | |
| 15th electrode | | |
| 16th electrode | Gene F detection | Nucleic acid probe F |
| 17th electrode | | |
| 18th electrode | | |
| 19th electrode | Negative control | Nucleic acid probe G |
| 20th electrode | | |
| 21st electrode | | |
| 22nd electrode | Gene H detection | Nucleic acid probe H |
| 23rd electrode | | |
| 24th electrode | | |
| 25th electrode | Gene I detection | Nucleic acid probe I |
| 26th electrode | | |
| 27th electrode | | |

1-2. Assembly of the Nucleic Acid Detection Cassette

To construct a nucleic acid detection cassette, the upper plate 50, the lower plate 30, and the packing 40 were prepared. These members were stacked and fixed to form a laminated structure. The upper plate 50, the lower plate 30, and the packing 40 have concave portions, convex portions, and grooves formed or drilled so that channels, the amplification unit and the detection unit 90 constructed by mounting the DNA chip in 1-1, and syringes in which reagents are sealed are formed inside the laminated structure. Also, one end of a channel is opened to the outside of the laminated structure to provide the sample injection port 710 to inject a sample into the channel. A plurality of wells is formed on the channel of the amplification unit 80 and one type of primer set is releasably immobilized on the inner wall of each well.

Primer sets for amplification that are immobilized are designed for amplification reaction by the LAMP method. The base sequence of primer DNA contained in each primer set is shown in Table 4.

TABLE 4

Primer set

| Set name | Sequence name | Sequence | Number of bases |
|---|---|---|---|
| A | A-FIP (SEQ ID NO: 10) | GCACTGCTTTGAATAGAGGCACTGTTCCCGATGACCTG | 38 |
| | A-BIP (SEQ ID NO: 11) | CCATATTGGCTACAACGTGCTACCTGATTGCCCCAACA | 38 |
| | A-F3 (SEQ ID NO: 12) | AGGGCTGGTACATTAGGAGA | 20 |
| | A-B3 (SEQ ID NO: 13) | GTCATATTAGTACTGCGAGTGG | 22 |
| | A-LPF (SEQ ID NO: 14) | CAGTAGTTCCTGAACCTTTAATGTACA | 27 |
| B | B-FIP (SEQ ID NO: 15) | GGATGACCACTAATACCTACACCCTGTGTTGGTTTAGAGGTAGGTC | 46 |
| | B-BIP (SEQ ID NO: 16) | CACTGAAAACTCTAATAGATATGCCGGTGCAACCAAGTAAACACAGTTGTG | 51 |
| | B-F3 (SEQ ID NO: 17) | AACTCAACGCTTAGTTTGGGC | 21 |
| | B-B3 (SEQ ID NO: 18) | CCTTTACCCCAATGCTCTCC | 20 |
| | B-LPF (SEQ ID NO: 19) | TAATGGCTGCCCGCGA | 16 |

TABLE 4 -continued

Primer set

| Set name | Sequence name | Sequence | Number of bases |
|---|---|---|---|
| C | C-FIP (SEQ ID NO: 20) | ATTATTGTGGCCCTGCGCACGTTCTATGGTAACCTCAGAATCCC | 44 |
|  | C-BIP (SEQ ID NO: 21) | ACCACTCGTAGCACTAACATGACTCGCCATGACGAAGGTATTCCT | 45 |
|  | C-F3 (SEQ ID NO: 22) | GCCACTGTACAAAGCAGTGC | 20 |
|  | C-B3 (SEQ ID NO: 23) | TGAATGTATGTCATAACATCAGCTG | 25 |
|  | C-LPB (SEQ ID NO: 24) | GCTGAGGTTAAAAAGGAAAGCACA | 24 |
| D | D-FIP (SEQ ID NO: 25) | AATTGATTACCCCAGCAAATGCCGTCTATGATTACGTCTGAGGCAC | 46 |
|  | D-BIP (SEQ ID NO: 26) | ATACTACTAGAAGTACTAACATGACCCTCCACATGTCTAAGGTACTG | 47 |
|  | D-F3 (SEQ ID NO: 27) | GTATATGTTGCTACGCCTAGTG | 22 |
|  | D-B3 (SEQ ID NO: 28) | GCCATAACCTCTGCAGACAAAG | 22 |
|  | D-LPF (SEQ ID NO: 29) | GCACGTTGCAACCAATAAGG | 20 |
| E | E-FIP (SEQ ID NO: 30) | CACTGAGTCCTACCCCTAAAGGTTGTCTCAACGCTTGGTCTGG | 43 |
|  | E-BIP (SEQ ID NO: 31) | GATGACACTGAAAACTCTCATGTAGCGCTGAGTTTGTTTATAATCCACAG | 50 |
|  | E-F3 (SEQ ID NO: 32) | CCAGATAACACAGTATATGATCCTAAC | 27 |
|  | E-B3 (SEQ ID NO: 33) | GCAGGTACACAGCCAATAATACAC | 24 |
|  | E-LPB (SEQ ID NO: 34) | GCTGTTGATACCAAAGATACACGTG | 25 |
| F | F-FIP (SEQ ID NO: 35) | TAAAATGGATGGCCACTTAGGCCGGTATGGAAATTGGTCGTGGGC | 45 |
|  | F-BIP (SEQ ID NO: 36) | GGATGATACAGAAAGTGCTCAAAATACACAGCTGTGTTTGC | 41 |
|  | F-F3 (SEQ ID NO: 37) | GAAACACAACGTTTGGTTTGGGC | 23 |
|  | F-B3 (SEQ ID NO: 38) | GTGCTCACCAATAGCAGGTAC | 21 |
|  | F-LPF (SEQ ID NO: 39) | CAATACCTAAAGGCTGCC | 18 |
| G |  | No primer due to negative control |  |
| H | H-FIP (SEQ ID NO: 40) | AACATATACCATTGTTGTGGCCCTTCCATGGTAACCTCTGATTCCC | 46 |
|  | H-BIP (SEQ ID NO: 41) | CTACCCGTAGTACCAACTTTACCCACGTGCCTGGTATATTCC | 42 |
|  | H-F3 (SEQ ID NO: 42) | GTTCTGTATACTGCCCCTCTC | 21 |
|  | H-B3 (SEQ ID NO: 43) | GACATAACATCAGTTGTTAATGTGAC | 26 |
|  | H-LPF (SEQ ID NO: 44) | CCTTATGTAGCCAATAAGGC | 20 |
| I | I-FIP (SEQ ID NO: 45) | GGATAACTGCAGTATTACCGGACCTAGGGCTGGAAAACTTGG | 42 |
|  | I-BIP (SEQ ID NO: 46) | TCCAACTCCTAGTGGCTCTATAGCGCTGTAGCCAATAAGGC | 41 |
|  | I-F3 (SEQ ID NO: 47) | GACGTGAGCAGATGTTTGT | 19 |
|  | I-B3 (SEQ ID NO: 48) | CCATTGTTATGACCTTGTGC | 20 |
|  | I-LPB (SEQ ID NO: 49) | CCTCAGAATCACAATTATTTAATAAGCC | 28 |

A set A, a set B, a set C, a set D, a set E, a set F, a set H, and a set I were prepared as primer sets. Each primer set was designed to contain an FI primer (FIP), a BI primer (BIP), an F3 primer (F3), a B3 primer (B3), and a loop primer (LPF or LPB). To prepare a primer solution containing each primer set, primer solutions each containing 200 μM of FIP, BIP, F3, B3, and LPF or LPB were prepared. 0.036 μL, 0.036 μL, 0.005 μL, 0.005 μL, and 0.018 μL of an FIP solution, a BIP solution, an F3 solution, a B3 solution, and an LPF (or LPB) solution obtained as described were mixed respectively. Accordingly, a primer set solution of the total amount of 0.100 μL containing all primers needed to amplify each one type of target DNA was prepared. Each primer set solution was dripped into a well of the amplification unit and dried at 40° C. for two minutes to fix the primer set to the amplification unit. Here, the primer set was fixed to the well with 2-mm pitches, 4-mm pitches, or 8-mm pitches. A total of six nucleic acid detection cassettes including two cassettes with 2-mm pitches, two cassettes with 4-mm pitches, and two cassettes with 8-mm pitches were created.

2. Detection of Nucleic Acid 2-1. Preparation of a Sample Solution

Eight types of nucleic acid used as replicative DNA, that is, a gene A, a gene B, a gene C, a gene D, a gene E, a gene F, a gene H, and a gene I were prepared. The sequences of replicative DNA contains in the gene A, the gene B, the gene C, the gene D, the gene E, the gene F, the gene H, and the gene I are shown in Table 5. The replicative DNA are sequences amplified by the above primer sets and these are a template A, a template B, a template C, a template D, a template E, a template F, a template H, and a template I corresponding to the genes A, B, C, D, E, F, H, and I respectively.

TABLE 5

| Template name | Sequence (excerpts from partial sequences) | Number of bases |
|---|---|---|
| A (SEQ ID NO: 50) | AGGGCTGGTACATTAGGAGAGGCTGTTCCCGATGACCTGTACATTAAAGGTTCAGGAACTACTGCC TCTATTCAAAGCAGTGCTTTTTTTCCCACTCCTAGTGGATCAATGGTTACTTCCGAATCTCAGTTAT TTAATAAGCCATATTGGCTACAACGTGCACAAGGTCATAATAATGGTATTGTTGGGGCAATCAGG TATTTGTTACTGTGGTAGATACCACTCGCAGTACTAATATGAC | 2.7 kbp |
| B (SEQ ID NO: 51) | AACTCAACGCTTAGTTTGGGCCTGTGTTGGTTTAGAGGTAGGTCGCGGGCAGCCATTAGGTGTAGG TATTAGTGGTCATCCATTATTAAATAAATTTGATGACACTGAAAACTCTAATAGATATGCCGGTGGT CCTGGCACTGATAATAGGGAATGTATATCAATGGATTATAAACAAACACAACTGTGTTTACTTGGTT GCAAACCACCTATTGGAGAGCATTGGGGTAAAGG | 2.7 kbp |
| C (SEQ ID NO: 52) | GCCACTGTACAAAGCAGTGCTTTTTTTCCTACTCCTAGTGGTTCTATGGTAACCTCAGAATCCCAAT TATTTAATAAACCGTACTGGTTACAACGTGCGCAGGGCCACAATAATGGCATATGTTGGGGCAATC AGTTGTTTGTCACAGTTGTGGATACCACTCGTAGCACTAACATGACTTTATGTGCTGAGGTTAAAAA GGAAAGCACATATAAAAATGAAAATTTTAAGGAATACCTTCGTCATGGCGAGGAATTTGATTTACAA TTTATTTTTCAATTGTGCAAAATTACATTAACAGCTGATGTTATGACATACATTCA | 2.7 kbp |
| D (SEQ ID NO: 53) | GTATATGTTGCTACGCCTAGTGGGTCTATGATTACGTCTGAGGCACAGTTATTTAATAAACCTTATT GGTTGCAACGTGCCCAAGGCCATAATAATGGCATTTGCTGGGGTAATCAATTATTTGTTACTGTAG TAGATACTACTAGAAGTACTAACATGACTATTAGTACTGCTACAGAACAGTTAAGTAAATATGATGC ACGAAAAATTAATCAGTACCTTAGACATGTGGAGGAATATGAATTACAATTTGTTTTTCAATTATGC AAAATTACTTTGTCTGCAGAGGTTATGGC | 2.7 kbp |
| E (SEQ ID NO: 54) | CCAGATAACACAGTATATGATCCTAACTCTCAACGCTTGGTCTGGGCCTGTGTAGGTGTTGAAATCGG TCGGGGCCAACCTTTAGGGGTAGGACTCAGTGGTCATCCATTATATAATAAATTGGATGACACTGAAA ACTCTCATGTAGCATCTGCTGTTGATACCAAAGATACACGTGATAATGTATCTGTGGATTATAAACAA ACTCAGCTGTGTATTATTGGCTGTGTACCTGC | 2.7 kbp |
| F (SEQ ID NO: 55) | GAAACACAACGTTTGGTTTGGGCATGTGTAGGTATGGAAATTGGTCGTGGGCAGCCTTTAGGTATTGG CCTAAGTGGCCATCCATTTTATAATAAATTGGATGATACAGAAAGTGCTCATGCAGCTACAGCTGTTA TTACGCAGGATGTTAGGGATAATGTGTCAGTTGATTATAAGCAAACACAGCTGTGTATTTTAGGTTGT GTACCTGCTATTGGTGAGCAC | 2.7 kbp |
| G | No template sequence due to negative control | |
| H (SEQ ID NO: 56) | GTTCTGTATACTGCCCCTCTCCCAGCGGTTCCATGGTAACCTCTGATTCCCAGTTATTTAATAAGCCT TATTGGCTACATAAGGCCCAGGGCCACAACAATGGTATATGTTGGCATAATCAATTATTTCTTACTGT TGTGGACACTACCCGTAGTACCAACTTTACATTATCTACCTCTATAGAGTCTTCCATACCTTCTACAT ATGATCCTTCTAAGTTTAAGGAATATACCAGGCACGTGGAGGAGTATGATTTACAATTTATATTTCAA CTGTGTACTGTCACATTAACAACTGATGTTATGTC | 2.7 kbp |
| I (SEQ ID NO: 57) | GACGTGAGCAGATGTTTGTTAGACACTTTTTTAATAGGGCTGGAAAACTTGGCGAGGCTGTCCCGGAT GACCTTTATATTAAAGGGTCCGGTAATACTGCAGTTATCCAAAGTAGTGCATTTTTTCCAACTCCTAG TGGCTCTATAGTTACCTCAGAATCACAATTATTTAATAAGCCTTATTGGCTACAGCGTGCACAAGGTC ATAACAATGG | 2.7 kbp |

As a sample solution to be injected into the nucleic acid detection cassette, a solution containing the above eight types of nucleic acid, Bst DNA polymerase, and a reaction mix was prepared. The concrete composition of the sample solution is shown in Table 5. The total amount was made 50 μL by adding distilled water (that is, DW)

TABLE 6

Composition of the sample solution

| Composition | Gene name | Amount of addition (μL) |
|---|---|---|
| Reaction Mixture | | 14.00 |
| DNA Polymerase | | 8.00 |
| Replicative DNA | A | 2.00 |
| | B | 2.00 |
| | C | 2.00 |
| | D | 2.00 |
| | E | 2.00 |
| | F | 2.00 |
| | H | 2.00 |
| | I | 2.00 |
| DW | | 12.00 |
| Total | | 50.00 |

The nucleic acid detection cassettes used in the following test are designed to promote the reaction as described below.

The sample solution contains the template A, the template B, the template C, the template D, the template E, the template F, the template H, and the template I. The sample solution is added to the channel of the nucleic acid detection cassette through the sample injection port. Each of the primer set A, the primer set B, the primer set C, the primer set D, the primer set E, the primer set F, the primer set H, and the primer set I is releasably immobilized in two wells of the amplification unit of the nucleic acid detection cassette. That is, the primer set A is immobilized in a well A1 and a well A2, the primer set B is immobilized in a well B1 and a well B2, the primer set C is immobilized in a well C1 and a well C2, the primer set D is immobilized in a well D1 and a well D2, the primer set E is immobilized in a well E1 and a well E2, the primer set F is immobilized in a well F1 and a well F2, the primer set H is immobilized in a well H1 and a well H2, and the primer set I is immobilized in a well I1 and a well I2.

These primer sets are released by the sample solution sent to the amplification unit. The replicative DNA is amplified by the corresponding primer set in each well as described below while the amplification unit is heated. In the well A1 and the well A2, the template A is amplified by the primer set A. In the well B1 and the well B2, the template B is amplified by the primer set B. In the well C1 and the well C2, the template C is amplified by the primer set C. In the well D1 and the well D2, the template D is amplified by the primer set D. In the well E1 and the well E2, the template E is amplified by the primer set E. In the well F1 and the well F2, the template F is amplified by the primer set F. In the well H1 and the well H2, the template H is amplified by the primer set H. In the well I1 and the well I2, the template I is amplified by the primer set I. The sample solution containing amplification products generated by the amplification unit as described above is sent to the detection unit.

In the detection unit, the nucleic acid probe A, the nucleic acid probe B, the nucleic acid probe C, the nucleic acid probe D, the nucleic acid probe E, the nucleic acid probe F, the nucleic acid probe G, the nucleic acid probe H, and the nucleic acid probe I are immobilized. In the sample solution sent to the detection unit and containing amplification products, an amplification product A, an amplification product B, an amplification product C, an amplification product D, an amplification product E, an amplification product F, an amplification product H, and an amplification product I derived from the template A, the template B, the template C, the template D, the template E, the template F, the template H, and the template I respectively are contained. These amplification products hybridize with corresponding nucleic acid probes. In the test of a nucleic acid detection cassette, whether a corresponding gene is present in the sample solution is determined by detecting a hybridize signal generated by the hybridization. More specifically, the amplification product A, the amplification product B, the amplification product C, the amplification product D, the amplification product E, the amplification product F, the amplification product H, and the amplification product I are designed to hybridize with the nucleic acid probe A, the nucleic acid probe B, the nucleic acid probe C, the nucleic acid probe D, the nucleic acid probe E, the nucleic acid probe F, the nucleic acid probe H, and the nucleic acid probe I. By detecting a signal from the electrodes to which the nucleic acid probe A, the nucleic acid probe B, the nucleic acid probe C, the nucleic acid probe D, the nucleic acid probe E, the nucleic acid probe F, the nucleic acid probe H, and the nucleic acid probe I are fixed, whether the gene A, the gene B, the gene C, the gene D, the gene E, the gene F, the gene H, and the gene I are contained in the sample solution subjected to the test can be determined.

2-2. Addition of the Template Solution

50 μL of the template solution prepared in 2-1 was sent to the reaction area, that is, the amplification unit and then, to the detection unit.

2-3. Reaction of Nucleic Acid

Various reactions were caused by heating and cooling the reaction area under conditions shown in Table 7 below:

TABLE 7

Reaction conditions of various reactions

| Reaction type | Reaction temperature | Reaction time |
|---|---|---|
| Nucleic acid amplification reaction | 64° C. | 60 min |
| Hybridization reaction | 50° C. | 10 min |
| Cleaning reaction | 30° C. | 5 min |
| Current detection reagent (Hoechst 33258) reaction | 25° C. | 3 min |

2-4. Detection of Nucleic Acid

A potential was swept to each probe nucleic acid immobilization working electrode to measure an oxidation current of Hoechst 33258 molecules specifically bound to double strands formed from a nucleic acid probe and an amplification product.

Result

FIGS. 42A, 42B, and 42C schematically show states in which primer sets are immobilized on the amplification unit of the nucleic acid detection cassette with 2-mm pitches, 4-mm pitches, and 8-mm pitches respectively. In the nucleic acid detection cassette, wells are basically formed with 2-mm pitches. Therefore, in the case of 2-mm pitches, primer sets are immobilized in neighboring wells (see FIG. 42A). In the case of 4-mm pitches, a well where no primer set is immobilized is arranged therebetween (see FIG. 42B). In the case of 8-mm pitches, as shown in FIG. 42C, primer sets are immobilized in wells arranged such that the pitch becomes 8 mm.

The result obtained from such a nucleic acid detection cassette is shown in Table 8.

TABLE 8

| | Detection result | | |
|---|---|---|---|
| | Immobilized well pitch | | |
| Gene name | 2 mm | 4 mm | 8 mm |
| A | 19 | 69 | 64 |
| B | 56 | 53 | 51 |
| C | 62 | 57 | 58 |
| D | 49 | 51 | 52 |
| E | 66 | 61 | 58 |
| F | 22 | 55 | 59 |
| G | 18 | 21 | 18 |
| H | 62 | 62 | 65 |
| I | 53 | 59 | 56 |
| Positive rate | 75% | 100% | 100% |

The positive rate was calculated by considering a nucleic acid probe from which a significantly large current was obtained when compared with the negative control as positive. The positive rate was low when a nucleic acid probe is immobilized with 2-mm pitches and the positive rate of 100% was achieved by immobilizing a nucleic acid probe with 4-mm pitches or 8-mm pitches. From the above results, it becomes clear that multi-amplification of a sample solution containing a plurality of different templates can satisfactorily be performed by immobilizing primer sets with 4-mm pitches or more. Therefore, it is verified that a plurality of target nucleic acid can be detected more correctly simultaneously by using a nucleic acid detection cassette in which primer sets are immobilized with 4-mm pitches or more. That is, according to the nucleic acid detection cassette in an embodiment, it is verified that a plurality of mutually different genes contained in a sample solution can reliably be detected.

The above embodiment includes various aspects described below and an example according to a combination of these aspects may also be included.

(1-1)

A nucleic acid detection cassette comprising:

a plurality of syringes that stores a sample solution or an intercalating agent solution;

an amplification unit that generates an amplification product by amplifying DNA in the sample solution;

a detection unit connected to the amplification unit so that the amplification product is supplied from the amplification unit to detect the amplification product supplied;

a first channel that connects, among the plurality of syringes, a first syringe in which the sample solution is stored to the detection unit via the amplification unit; and a second channel that connects, among the plurality of syringes, a second syringe in which the intercalating agent solution is stored to the detection unit.

(1-2)

The nucleic acid detection cassette of (1-1), comprised of first and second plates made of a rigid material and packing provided fixedly between the first and second plates like being compressed and made of an elastic material, further comprising: first, second, third, and fourth channels connected to a fifth channel in common and the fifth channel, wherein the plurality of syringes is formed by the first plate and the packing and includes first, second, third, and fourth syringes deformable from outside, the first syringe comprises an injection portion capable of injecting the sample solution from outside, the first syringe corresponds to the syringe storing the sample solution and connected to the first channel, the third syringe corresponds to the syringe storing the intercalating agent solution and connected to the second channel, a first cleaning fluid is stored in the second syringe, a second cleaning fluid having a same composition as the first cleaning fluid's is stored in the fourth syringe, the amplification unit is formed by the first plate and the packing between the first plate and the packing has a primer set that generates an amplification product by amplifying the sample DNA in the sample solution fixed thereto, the detection includes a DNA chip placed on the first plate and having an electrode to electrically detect a hybridization reaction and a plurality of electrode pads connected to the electrode, the detection unit further includes a detection channel formed between the DNA chip and the packing, connected to the amplification unit so that the sample solution containing the amplification product is supplied from the amplification unit, and having the electrode arranged therein, the first, second, third, fourth, and fifth channels are formed between the first plate and the packing, the first and second channels are communicatively connected to the first and second syringes respectively and connected to the amplification unit in common so that the sample solution is supplied and then, the first cleaning fluid is supplied to the amplification unit, and the fifth channel is connected between the amplification channel and the detection channel so that the sample solution containing the amplification product is supplied from the amplification unit by the first cleaning fluid being supplied, and the third and fourth channels are communicatively connected to the third and fourth syringes respectively so that the sample solution is pushed out of the detection unit by supplying the second cleaning fluid to the detection channel and then, the second cleaning fluid in the detection channel is pushed out by supplying the intercalating agent solution.

(1-3)

A liquid sending method of the nucleic acid detection cassette according of (1-2), comprising:

supplying the sample solution from the first syringe to the amplification unit via the first channel by crushing the first syringe;

generating an amplification product by heating the amplification unit from outside to amplify sample DNA in the sample solution;

supplying the sample solution containing the amplification product in the amplification unit to the detection unit via the fifth channel by supplying the first cleaning fluid from the second syringe to the amplification unit via the second channel by crushing the second syringe;

causing a hybridization reaction in the detection unit;

pushing out the sample solution out of the detection unit by supplying the second cleaning fluid from the third syringe to the detection unit via the third channel by crushing the third syringe; and pushing out the second cleaning fluid out of the detection unit by supplying the intercalating agent solution from the fourth syringe to the detection unit via the fourth channel by crushing the fourth syringe.

(2-1)

A nucleic acid detection cassette including:

an injection portion that injects a sample solution;

a storage portion that stores the sample solution;

an elastic member that covers the storage portion; and a channel through which the sample solution injected from the injection portion flows to the storage portion, wherein the injection portion further includes an opening provided like protruding from the elastic member and communicatively connected to the channel to inject the sample solution, an air vent opening, and a sealing member that deforms and fluid-tightly closes these openings.

(3-1)

A nucleic acid detection cassette including:

a first plate and a second plate, each of which having a through hole;

an elastic member provided between the first plate and the second plate and having a first area having a predetermined thickness and a second area having a second thickness thinner than the predetermined thickness;

an injection portion that injects a sample solution;

a storage portion that stores the sample solution injected from the injection portion; and a channel through which the sample solution injected from the injection portion flows to the storage portion, wherein the first area of the elastic member is provided so as to cover at least the channel and the storage portion.

(3-2)

A nucleic acid detection cassette including:

a first plate made of a rigid material and having a through hole;

a second plate made of the rigid material and having a syringe depression and a channel groove;

packing made of an elastic material and provided with a zonal convex area having a deformable swelling portion and a first thickness and a concave area having a second thickness thinner than the first thickness and provided around the convex area in a predetermined pattern on a first surface, wherein the packing is placed on the second plate such that the swelling portion covers the syringe depression, the syringe depression us surrounded by the convex area, and the convex area covers the channel groove and the first plate is placed on the packing such that the swelling portion is arranged inside the through hole and the packing is fixed so as to be compressed between the first and second plates;

a syringe fluid-tightly formed from the syringe depression, the swelling portion, and the convex area so as to be deformable from outside via the through hole; and a channel formed from the channel groove and the convex area and communicatively connected to the syringe.

(3-3)

The nucleic acid detection cassette of (3-2), wherein the first plate has a frame portion defining a cavity of a waste liquid tank, a through hole through which the frame portion is inserted is formed in the packing, the convex area is provided like surrounding the through hole, and the frame portion is inserted through the through hole of the packing and the convex area is fluid-tightly brought into close contact with an undersurface of the first plate to form the waste liquid tank.

(3-4)

The nucleic acid detection cassette of (3-2), wherein the first plate has a stud pin, the packing has a through hole through which the stud pin is inserted and which has an inside diameter larger than the stud pin, the convex area is provided like surrounding the through hole, the second plate has a stud hole into which the stud pin is inserted and when the first plate is mounted and fixed to the second plate, the stud is secured to the stud hole and the convex area is pushed into the through hole so that the stud is retained by the stud hole.

(3-5)

The nucleic acid detection cassette of (3-2), wherein the first plate has an auxiliary groove and the packing has the convex area formed on the first surface corresponding to the auxiliary groove like causing a flat surface provided on a second surface opposed to the first surface to be brought into close contact with the auxiliary groove to form an auxiliary channel between the auxiliary groove and the flat surface and the packing has a through hole that communicatively connects the auxiliary channel and the channel.

(3-6)

The nucleic acid detection cassette of (3-2), wherein the first plate has an injection port through which a solution can be injected into the syringe from outside, the packing has a protruding portion inserted into the injection port, a channel hole communicatively connected to the channel is formed in the protruding portion, and when the protruding portion is inserted into the injection port, the solution can be supplied to the syringe via the channel hole and the channel.

(3-7)

The nucleic acid detection cassette of (3-2), further including an amplification unit formed by the second plate and the packing and comprised of an amplification channel where a primer set that generates an amplification product by amplifying sample DNA in a sample solution is fixed, wherein the amplification unit has an amplification channel defined between the channel groove of the second plate and the packing.

(3-8)

The nucleic acid detection cassette of (3-7), further including a detection unit including a DNA chip placed on the second plate and having an electrode to electrically detect a hybridization reaction and a plurality of electrode pads connected to the electrode, formed between the DNA chip and the packing, connected to the amplification unit so that the sample solution containing the amplification product is supplied from the amplification unit, and further including a detection channel on which the electrode is arranged.

(4-1)

A nucleic acid detection cassette comprising:

a first plate and a second plate, each of which having a through hole;

an elastic member provided between the first plate and the second plate and having a first area having a predetermined thickness and a second area having a second thickness thinner than the predetermined thickness;

an injection portion that injects a sample solution;

a storage portion that stores the sample solution injected from the injection portion; and a channel through which the sample solution injected from the injection portion is supplied to the storage portion, wherein the first area of the elastic member is provided so as to cover at least the channel and the storage portion.

(4-2)

The nucleic acid detection cassette of (4-2), wherein the first and second plates are made of a rigid material and the second plate has a syringe depression and a channel groove, the elastic member includes packing made of an elastic material, the packing has a swelling portion that can be deformed, a convex area in a zonal shape having a first thickness corresponding to the first area, and a concave area having a second thickness thinner than the first thickness and provided around the convex area corresponding to the second area, and the swelling portion, the convex area in the zonal shape, and the concave area are provided on a first surface in a predetermined pattern, the swelling portion covers the syringe depression, the convex area surrounds the syringe depression, and the packing is placed on the second plate so that the convex area covers the channel groove, the first plate is placed on the packing so that the swelling portion is arranged inside the through hole and the packing is fixed like being compressed between the first and second plates, the storage portion includes a syringe and the syringe is fluid-tightly formed by the syringe depression, the swelling portion, and the convex portion so as to be deformable from outside via the through hole, and the channel is formed from the channel groove and the convex area covering the channel and communicatively connected to the syringe.

(5-1)

A nucleic acid detection cassette including:

a plurality of syringes that stores a sample solution or an intercalating agent solution;

an amplification unit that generates an amplification product by amplifying DNA in the sample solution;

a detection unit connected to the amplification unit so that the amplification product is supplied from the amplification unit to detect the amplification product supplied;

a first channel that connects, among the plurality of syringes, a syringe in which the sample solution is stored, the amplification unit, and the detection unit; and a second channel that connects, among the plurality of syringes, a syringe in which the intercalating agent solution is stored and the detection unit.

(5-2)

A nucleic acid detection cassette comprised of first and second plates made of a rigid material and packing made of an elastic material, the packing being provided fixedly between the first and second plates like being compressed, including:

first, second, third, and fourth syringes formed by the first plate and the packing and which can be deformed from outside;

an injection portion capable of injecting a sample solution into the first syringe from outside;

a first cleaning fluid stored in the second syringe;

an intercalating agent solution stored in the third syringe;

a second cleaning fluid stored in the fourth syringe and having a same composition as the first cleaning fluid's;

an amplification unit formed by the first plate and the packing and comprised of an amplification channel where a primer set that generates an amplification product by amplifying sample DNA in the sample solution is fixed;

a detection unit including a DNA chip placed on the first plate and having an electrode to electrically detect a hybridization reaction and a plurality of electrode pads connected to the electrode and further including a detection channel formed between the DNA chip and the packing, connected to the amplification unit so that the sample solution containing the amplification product is supplied from the amplification unit, and having the electrode arranged therein; and first, second, third, fourth, and fifth channels formed between the first plate and the packing, wherein the first and second channels are communicatively connected to the first and second syringes respectively and connected to the amplification unit in common so that the sample solution is supplied and then, the first cleaning fluid is supplied to the amplification unit, the fifth channel is connected between the amplification channel and the detection channel so that the sample solution containing the amplification product is supplied from the amplification unit by the first cleaning fluid being supplied, and the third and fourth channels are communicatively connected to the third and fourth syringes respectively so that so that the sample solution is pushed out of the detection unit by supplying the second cleaning fluid to the detection channel and then, the second cleaning fluid in the detection channel is pushed out by supplying the intercalating agent solution.

(5-3)

The nucleic acid detection cassette of (5-2), further including:

first and second normally closed valves provided in the first and second channels to close the first and second channels respectively, wherein the first normally closed valve is opened when the sample solution is supplied to the amplification unit and the first normally closed valve is opened when the first cleaning fluid is supplied to the amplification unit and third and fourth normally closed valves provided in the third and fourth channels to close the third and fourth channels respectively, wherein the third normally closed valve is opened when the second cleaning fluid is supplied to the amplification unit and the fourth normally closed valve is opened when the intercalating agent solution is supplied to the amplification unit.

(5-4)

The nucleic acid detection cassette of (5-2), wherein the amplification unit has an input port to which the first and second channels are connected in common and an output port to which the fifth channel is connected, further including:

a first normally open valve that maintains a connection of the input port to a common connection of the first and second channels open and a second normally open valve that maintains a connection of the output port to the fifth channel open, wherein the first and second normally open valves are provided in the input port and the output port so that the first and second normally open valves are closed when the amplification unit is heated from outside.

(5-5)

The nucleic acid detection cassette of (5-2), further including:

a waste liquid tank formed from a depression provided in the first and second plates and a through groove drilled in the packing; and a sixth channel provided between the first plate and the packing, wherein the sixth channel connects the detection unit to the waste liquid tank and guides the sample solution pushed out of the detection unit with the second cleaning fluid being supplied to the detection channel.

(5-6)

The nucleic acid detection cassette of (5-2), wherein the first, second, third, and fourth syringes are formed from first, second, third, and fourth syringe grooves formed in the first plate and first, second, third, and fourth swelling portions provided in the packing and covering the first, second, third, and fourth swelling portions respectively and the first, second, third, and fourth swelling portions are arranged in the first, second, third, and fourth syringe grooves provided in the second plate respectively and deformed from outside via the first, second, third, and fourth syringe grooves.

(5-7)

The nucleic acid detection cassette of (5-2), wherein the amplification unit is formed by covering a channel groove provided in the second plate with the packing and the electrode of the DNA chip includes a plurality of working electrodes to which a nucleic acid probe is fixed, a counter electrode to apply a voltage to the working electrodes, and a reference electrode to detect a reference voltage and the electrode pad is connected to the working electrode, the counter electrode, and the reference electrode.

(6-1)

A nucleic acid detection cassette comprising:

a first plate and a second plate, each of which having a through hole;

packing provided between the first plate and the second plate, having a first area having a predetermined thickness and a second area having a second thickness thinner than the predetermined thickness, and made of an elastic member;

an injection portion through which a sample is injected;

a first storage portion that stores a sample solution injected from the injection port and first and second syringes defining a second storage portion that stores an intercalating agent solution;

an amplification unit that generates an amplification product by amplifying DNA in the sample solution;

a detection unit connected to the amplification unit so that the amplification product is supplied from the amplification unit to detect the amplification product supplied;

an injection channel that supplies the sample injected from the injection portion to the first syringe;

a first channel that connects the first syringe to the detection unit via the amplification unit; and a second channel that connects the second syringe to the detection unit, wherein the first area of the packing is provided so as to cover at least the first channel and the storage portion.

(6-2)

The nucleic acid detection cassette described above items, wherein the first channel has a passing portion passing through the amplification unit, the passing portion includes a plurality of wells having a width larger than that of the channel, wells adjacent to each other are disposed by providing a predetermined interval from a center of one of the wells adjacent to each other to that of the other well by passing through an axis of the channel.

(6-3)

The nucleic acid detection cassette of (6-3), wherein wells adjacent to each other of the plurality of wells are liquid-joined by an interval channel and have the width larger than that of the interval channel, a plurality of types of primer sets is releasably immobilized on an inner wall of the well for each type, and a distance from the center of one of two relevant wells connected by the interval channel and in which relevant primer sets adjacent to each other along the channel are immobilized to that of the other well by passing through the axis of the channel is 4 mm or more.

(6-4)

The nucleic acid detection cassette of described above items, wherein the distance is 6 mm or more.

(6-5)

The nucleic acid detection cassette of described above items, wherein the width of the well is 1.5 to 3.0 times larger than that of the interval channel.

(6-6)

The nucleic acid detection cassette of described above items, wherein the injection portion includes an opening provided like protruding from the packing and communicatively connected to the injection portion to inject the sample solution, an air vent opening, and a sealing member that deforms and fluid-tightly closes these openings.

(6-7)

The nucleic acid detection cassette of (6-6), wherein the injection hole of the sample and the air vent hole of the sample are inserted and arranged in first and second through holes drilled in the first plate respectively and provided like protruding from the packing and the nucleic acid detection cassette comprises a cap and the cap is provided on the second plate in such a way that the cap can be brought into close contact with the injection opening of the sample and the air vent opening and fluid-tightly closed by deforming the injection opening of the sample and the air vent portion.

(6-8)

The nucleic acid detection cassette of (6-7), further comprising:

a cover plate mounted and fixed like covering the second plate and having a notched portion that exposes the opening for injecting the sample and the air vent opening;

a normally closed valve provided in the first and second channels communicatively connected to the first and second syringes, wherein the normally closed syringe includes:

a tubular portion provided in the packing, defining the first and second channels between the first plate and the packing, and having flexibility;

a through hole in which the tubular portion is arranged and which is drilled in the second plate; and a protruding portion provided on the cover plate, wherein when the cover plate is mounted on the second plate, the tubular portion arranged inside the through hole and having the flexibility is crushed to close the tubular portion.

(6-9)

The nucleic acid detection of described above items, wherein the first, second, third, and fourth syringes are each comprised of an elongated depression formed in the second plate to form a tubular space internally and a swelling portion in an elongated shape formed in the packing opposed to the depression and protruding in a direction opposite to the depression, a liquid in the tubular space of the syringe is sent to any one of the first, second, third, and fourth channels by crushing the swelling portion by imposing a load thereon using a syringe rod in an elongated shape provided in the liquid sending control mechanism, when a syringe width is $W_B$, a syringe rod width is $W_R$, and a thickness of the swelling portion is $t_E$, the syringe width is set so that a relationship of a formula below is satisfied:

$$W_R + 3t_E \leq W_B \leq W_R + 4t_E \qquad (1)$$

(6-10)

The nucleic acid detection cassette of described above items, wherein the amplification unit comprises an amplification channel having a volume (Va) and the detection unit comprises a detection channel having a volume (Vd) and when the volume of the amplification unit is Va, the volume of the detection unit is Vd, a standard deviation of a volume difference between the amplification unit and the detection unit is $\sigma_V$, the standard deviation of a liquid sending amount from the amplification unit to the detection unit is $\sigma_Q$, and the cross-sectional area of a specific area of a relevant detection channel continuously extending upstream and downstream of the detection unit is B, and the reaching limit distance of amplification products is L, the relationship between the volume (Va) of the amplification unit and the volume (Vd) of the detection unit satisfies a formula below:

$$(Vd+\Delta V_2) > Va > (Vd+\Delta V_1)$$

$$\Delta V_1 = 3(2\sigma_Q + \sigma_V)$$

$$\Delta V_2 = 2BL - 3(2\sigma_Q + \sigma_V)$$

(6-11)

The nucleic acid detection cassette of (6-10), wherein the amplification unit comprises a plurality of wells in which wells adjacent to each other are connected by the interval channel and the plurality of types of primer sets is immobilized in the wells for each type.

Thus, according to the embodiment, there is provided a highly-integrated nucleic acid detection cassette having high sealing properties that can be used for a nucleic acid testing device achieving automation from amplification of a sample to detection of an electrochemical reaction of the sample.

Also according to the embodiment, there is provided a nucleic acid detection cassette that can be used for a nucleic acid testing device including a handy sample injection port and a fluid-tight mechanism around the sample injection port.

Furthermore according to the embodiment, there is provided a nucleic acid detector capable of amplifying a plurality of types of nucleic acid simultaneously or in parallel and detecting the plurality of types of target nucleic acid in an obtained amplification product simultaneously or in parallel.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nucleic acid detection cassette comprising:
a laminated structure including;
an upper plate made of a rigid material,
a packing sheet made of an elastic material, and
a lower plate made of a rigid material, which seals the packing sheet together with the upper plate;
channels including an amplification channel to which a sample solution is supplied, a coupling channel, and a detection channel connected to the amplification channel through the coupling channel in series, which are formed in the laminated structure;
an amplification part formed in the laminated structure, which performs an amplification reaction using a plurality of types of primer sets with sample nucleic acid in the sample solution to produce an amplification product including a target DNA, the amplification part including a plurality of wells and interval channel portions, the wells having inner surfaces on which the primer sets are releasably immobilized, and interval channel portions coupling the wells in series so that the adjacent wells are liquid-jointed by the interval channel portions and the wells and the interval channel portions forms the amplification channel; and a detection part formed in the laminated structure, and including the detection channel, electrical electrodes arranged in the channel, and nucleic acid probes fixed on the electrical electrodes, wherein the amplification product is supplied from the amplification channel, and the target DNA in the amplification product reacts with the nucleic acid probe so that a hybridize signal is generated from the electrodes to detect a target DNA, wherein the wells have a width larger than a width of the interval channel portions, the plurality of types of primer sets which are releasably immobilized on inner walls of the wells for each type, and a distance between centers of the adjacent wells which is set within 4 mm to 8 mm along an axis of the arrangement of the channel portions, which connects the centers of the adjacent wells, and the width of the wells is 1.5 to 3.0 times larger than the width of the interval channel portions.

2. The nucleic acid detection cassette of claim 1, wherein the distance is set within 6 mm to 8 mm.

3. The nucleic acid detection cassette of claim 2, wherein the width of the wells is 1.7 to 2.3 times larger than the width of the interval channel portions.

4. The nucleic acid detection cassette of claim 1, wherein the width of the wells is 1.7 to 2.3 times larger than the width of the interval channel portions.

5. The nucleic acid detection cassette of claim 1, further comprising a first supplying part which supplies the sample solution to the amplification channel, and a second supply part which supplies the amplification product to the detection channel.

6. The nucleic acid detection cassette of claim 1, wherein the width of the interval channel is in a range from 0.05 to 1.5 mm.

7. The nucleic acid detection cassette of claim 1, wherein the width of the well is in a range from 0.2 mm to 3.0 mm.

\* \* \* \* \*

SEQUENCE LISTING

```
<160> NUMBER OF SEQ ID NOS: 57

<210> SEQ ID NO 1
<211> LENGTH: 35
<212> TYPE: DNA
<213> ORGANISM: Artificial Sequence
<220> FEATURE:
<223> OTHER INFORMATION: Synthetic probe

<400> SEQUENCE: 1
acaaggtcat aataatggta tttgttgggg caatc                           35

<210> SEQ ID NO 2
<211> LENGTH: 55
<212> TYPE: DNA
<213> ORGANISM: Artificial Sequence
<220> FEATURE:
<223> OTHER INFORMATION: Synthetic probe

<400> SEQUENCE: 2
tggtcctggc actgataata gggaatgtat atcaatggat tataaacaaa cacaa     55

<210> SEQ ID NO 3
<211> LENGTH: 41
<212> TYPE: DNA
<213> ORGANISM: Artificial Sequence
<220> FEATURE:
<223> OTHER INFORMATION: Synthetic probe

<400> SEQUENCE: 3
ttgtaaccag tacggtttat taaataattg ggattctgag g                    41

<210> SEQ ID NO 4
<211> LENGTH: 55
<212> TYPE: DNA
<213> ORGANISM: Artificial Sequence
<220> FEATURE:
```

<223> OTHER INFORMATION: Synthetic probe

<400> SEQUENCE: 4
agtactgcta cagaacagtt aagtaaatat gatgcacgaa aaattaatca gtacc    55

<210> SEQ ID NO 5
<211> LENGTH: 43
<212> TYPE: DNA
<213> ORGANISM: Artificial Sequence
<220> FEATURE:
<223> OTHER INFORMATION: Synthetic probe

<400> SEQUENCE: 5
gccccgaccg atttcaacac ctacacaggc ccagaccaag cgt    43

<210> SEQ ID NO 6
<211> LENGTH: 55
<212> TYPE: DNA
<213> ORGANISM: Artificial Sequence
<220> FEATURE:
<223> OTHER INFORMATION: Synthetic probe

<400> SEQUENCE: 6
agctacagct gttattacgc aggatgttag ggataatgtg tcagttgatt ataag    55

<210> SEQ ID NO 7
<211> LENGTH: 34
<212> TYPE: DNA
<213> ORGANISM: Artificial Sequence
<220> FEATURE:
<223> OTHER INFORMATION: Synthetic probe

<400> SEQUENCE: 7
accaataagg tttattgaat atttgggcat caga    34

<210> SEQ ID NO 8
<211> LENGTH: 55
<212> TYPE: DNA
<213> ORGANISM: Artificial Sequence
<220> FEATURE:
<223> OTHER INFORMATION: Synthetic probe

<400> SEQUENCE: 8
attatctacc tctatagagt cttccatacc ttctacatat gatccttcta agttt    55

<210> SEQ ID NO 9
<211> LENGTH: 41
<212> TYPE: DNA
<213> ORGANISM: Artificial Sequence
<220> FEATURE:
<223> OTHER INFORMATION: Synthetic probe

<400> SEQUENCE: 9
ctttaatata aaggtcatcc gggacagcct cgccaagttt t    41

<210> SEQ ID NO 10
<211> LENGTH: 38
<212> TYPE: DNA
<213> ORGANISM: Artificial Sequence
<220> FEATURE:
<223> OTHER INFORMATION: Synthetic primer

<400> SEQUENCE: 10
gcactgcttt gaatagaggc actgttcccg atgacctg    38

```
<210> SEQ ID NO 11
<211> LENGTH: 38
<212> TYPE: DNA
<213> ORGANISM: Artificial Sequence
<220> FEATURE:
<223> OTHER INFORMATION: Synthetic primer

<400> SEQUENCE: 11
ccatattggc tacaacgtgc tacctgattg ccccaaca                                  38

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
agggctggta cattaggaga                                                      20

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
gtcatattag tactgcgagt gg                                                   22

<210> SEQ ID NO 14
<211> LENGTH: 27
<212> TYPE: DNA
<213> ORGANISM: Artificial Sequence
<220> FEATURE:
<223> OTHER INFORMATION: Synthetic primer

<400> SEQUENCE: 14
cagtagttcc tgaacccttta atgtaca                                             27

<210> SEQ ID NO 15
<211> LENGTH: 46
<212> TYPE: DNA
<213> ORGANISM: Artificial Sequence
<220> FEATURE:
<223> OTHER INFORMATION: Synthetic primer

<400> SEQUENCE: 15
ggatgaccac taatacctac accctgtgtt ggtttagagg taggtc                         46

<210> SEQ ID NO 16
<211> LENGTH: 51
<212> TYPE: DNA
<213> ORGANISM: Artificial Sequence
<220> FEATURE:
<223> OTHER INFORMATION: Synthetic primer

<400> SEQUENCE: 16
cactgaaaac tctaatagat atgccggtgc aaccaagtaa acacagttgt g                   51

<210> SEQ ID NO 17
<211> LENGTH: 21
<212> TYPE: DNA
<213> ORGANISM: Artificial Sequence
<220> FEATURE:
<223> OTHER INFORMATION: Synthetic primer
```

<400> SEQUENCE: 17
aactcaacgc ttagtttggg c                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
cctttacccc aatgctctcc                                                20

<210> SEQ ID NO 19
<211> LENGTH: 16
<212> TYPE: DNA
<213> ORGANISM: Artificial Sequence
<220> FEATURE:
<223> OTHER INFORMATION: Synthetic primer

<400> SEQUENCE: 19
taatggctgc ccgcga                                                    16

<210> SEQ ID NO 20
<211> LENGTH: 44
<212> TYPE: DNA
<213> ORGANISM: Artificial Sequence
<220> FEATURE:
<223> OTHER INFORMATION: Synthetic primer

<400> SEQUENCE: 20
attattgtgg ccctgcgcac gttctatggt aacctcagaa tccc                     44

<210> SEQ ID NO 21
<211> LENGTH: 45
<212> TYPE: DNA
<213> ORGANISM: Artificial Sequence
<220> FEATURE:
<223> OTHER INFORMATION: Synthetic primer

<400> SEQUENCE: 21
accactcgta gcactaacat gactcgccat gacgaaggta ttcct                    45

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
gccactgtac aaagcagtgc                                                20

<210> SEQ ID NO 23
<211> LENGTH: 25
<212> TYPE: DNA
<213> ORGANISM: Artificial Sequence
<220> FEATURE:
<223> OTHER INFORMATION: Synthetic primer

<400> SEQUENCE: 23
tgaatgtatg tcataacatc agctg                                          25

<210> SEQ ID NO 24
<211> LENGTH: 24

<212> TYPE: DNA
<213> ORGANISM: Artificial Sequence
<220> FEATURE:
<223> OTHER INFORMATION: Synthetic primer

<400> SEQUENCE: 24
gctgaggtta aaaggaaag caca                                     24

<210> SEQ ID NO 25
<211> LENGTH: 46
<212> TYPE: DNA
<213> ORGANISM: Artificial Sequence
<220> FEATURE:
<223> OTHER INFORMATION: Synthetic primer

<400> SEQUENCE: 25
aattgattac cccagcaaat gccgtctatg attacgtctg aggcac            46

<210> SEQ ID NO 26
<211> LENGTH: 47
<212> TYPE: DNA
<213> ORGANISM: Artificial Sequence
<220> FEATURE:
<223> OTHER INFORMATION: Synthetic primer

<400> SEQUENCE: 26
atactactag aagtactaac atgaccctcc acatgtctaa ggtactg            47

<210> SEQ ID NO 27
<211> LENGTH: 22
<212> TYPE: DNA
<213> ORGANISM: Artificial Sequence
<220> FEATURE:
<223> OTHER INFORMATION: Synthetic primer

<400> SEQUENCE: 27
gtatatgttg ctacgcctag tg                                      22

<210> SEQ ID NO 28
<211> LENGTH: 22
<212> TYPE: DNA
<213> ORGANISM: Artificial Sequence
<220> FEATURE:
<223> OTHER INFORMATION: Synthetic primer

<400> SEQUENCE: 28
gccataacct ctgcagacaa ag                                      22

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
gcacgttgca accaataagg                                         20

<210> SEQ ID NO 30
<211> LENGTH: 43
<212> TYPE: DNA
<213> ORGANISM: Artificial Sequence
<220> FEATURE:
<223> OTHER INFORMATION: Synthetic primer

<400> SEQUENCE: 30
cactgagtcc taccectaaa ggttgtctca acgcttggtc tgg       43

<210> SEQ ID NO 31
<211> LENGTH: 50
<212> TYPE: DNA
<213> ORGANISM: Artificial Sequence
<220> FEATURE:
<223> OTHER INFORMATION: Synthetic primer

<400> SEQUENCE: 31
gatgacactg aaaactctca tgtagcgctg agtttgttta taatccacag       50

<210> SEQ ID NO 32
<211> LENGTH: 27
<212> TYPE: DNA
<213> ORGANISM: Artificial Sequence
<220> FEATURE:
<223> OTHER INFORMATION: Synthetic primer

<400> SEQUENCE: 32
ccagataaca cagtatatga tcctaac       27

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
gcaggtacac agccaataat acac       24

<210> SEQ ID NO 34
<211> LENGTH: 25
<212> TYPE: DNA
<213> ORGANISM: Artificial Sequence
<220> FEATURE:
<223> OTHER INFORMATION: Synthetic primer

<400> SEQUENCE: 34
gctgttgata ccaaagatac acgtg       25

<210> SEQ ID NO 35
<211> LENGTH: 45
<212> TYPE: DNA
<213> ORGANISM: Artificial Sequence
<220> FEATURE:
<223> OTHER INFORMATION: Synthetic primer

<400> SEQUENCE: 35
taaaatggat ggccacttag gccggtatgg aaattggtcg tgggc       45

<210> SEQ ID NO 36
<211> LENGTH: 41
<212> TYPE: DNA
<213> ORGANISM: Artificial Sequence
<220> FEATURE:
<223> OTHER INFORMATION: Synthetic primer

<400> SEQUENCE: 36
ggatgataca gaaagtgctc aaaatacaca gctgtgtttg c       41

<210> SEQ ID NO 37
<211> LENGTH: 23
<212> TYPE: DNA
<213> ORGANISM: Artificial Sequence

```
<220> FEATURE:
<223> OTHER INFORMATION: Synthetic primer

<400> SEQUENCE: 37
gaaacacaac gtttggtttg ggc                                              23

<210> SEQ ID NO 38
<211> LENGTH: 21
<212> TYPE: DNA
<213> ORGANISM: Artificial Sequence
<220> FEATURE:
<223> OTHER INFORMATION: Synthetic primer

<400> SEQUENCE: 38
gtgctcacca atagcaggta c                                                21

<210> SEQ ID NO 39
<211> LENGTH: 18
<212> TYPE: DNA
<213> ORGANISM: Artificial Sequence
<220> FEATURE:
<223> OTHER INFORMATION: Synthetic primer

<400> SEQUENCE: 39
caatacctaa aggctgcc                                                    18

<210> SEQ ID NO 40
<211> LENGTH: 46
<212> TYPE: DNA
<213> ORGANISM: Artificial Sequence
<220> FEATURE:
<223> OTHER INFORMATION: Synthetic primer

<400> SEQUENCE: 40
aacatatacc attgttgtgg cccttccatg gtaacctctg attccc                     46

<210> SEQ ID NO 41
<211> LENGTH: 42
<212> TYPE: DNA
<213> ORGANISM: Artificial Sequence
<220> FEATURE:
<223> OTHER INFORMATION: Synthetic primer

<400> SEQUENCE: 41
ctacccgtag taccaacttt acccacgtgc ctggtatatt cc                         42

<210> SEQ ID NO 42
<211> LENGTH: 21
<212> TYPE: DNA
<213> ORGANISM: Artificial Sequence
<220> FEATURE:
<223> OTHER INFORMATION: Synthetic primer

<400> SEQUENCE: 42
gttctgtata ctgcccctct c                                                21

<210> SEQ ID NO 43
<211> LENGTH: 26
<212> TYPE: DNA
<213> ORGANISM: Artificial Sequence
<220> FEATURE:
<223> OTHER INFORMATION: Synthetic primer

<400> SEQUENCE: 43
gacataacat cagttgttaa tgtgac                                           26
```

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
ccttatgtag ccaataaggc                                               20

<210> SEQ ID NO 45
<211> LENGTH: 42
<212> TYPE: DNA
<213> ORGANISM: Artificial Sequence
<220> FEATURE:
<223> OTHER INFORMATION: Synthetic primer

<400> SEQUENCE: 45
ggataactgc agtattaccg gacctagggc tggaaaactt gg                      42

<210> SEQ ID NO 46
<211> LENGTH: 41
<212> TYPE: DNA
<213> ORGANISM: Artificial Sequence
<220> FEATURE:
<223> OTHER INFORMATION: Synthetic primer

<400> SEQUENCE: 46
tccaactcct agtggctcta tagcgctgta gccaataagg c                       41

<210> SEQ ID NO 47
<211> LENGTH: 19
<212> TYPE: DNA
<213> ORGANISM: Artificial Sequence
<220> FEATURE:
<223> OTHER INFORMATION: Synthetic primer

<400> SEQUENCE: 47
gacgtgagca gatgtttgt                                                19

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
ccattgttat gaccttgtgc                                               20

<210> SEQ ID NO 49
<211> LENGTH: 28
<212> TYPE: DNA
<213> ORGANISM: Artificial Sequence
<220> FEATURE:
<223> OTHER INFORMATION: Synthetic primer

<400> SEQUENCE: 49
cctcagaatc acaattattt aataagcc                                      28

<210> SEQ ID NO 50
<211> LENGTH: 242
<212> TYPE: DNA
<213> ORGANISM: Artificial Sequence
<220> FEATURE:
<223> OTHER INFORMATION: template

<400> SEQUENCE: 50

```
agggctggta cattaggaga ggctgttccc gatgacctgt acattaaagg ttcaggaact      60
actgcctcta ttcaaagcag tgcttttttt cccactccta gtggatcaat ggttacttcc     120
gaatctcagt tatttaataa gccatattgg ctacaacgtg cacaaggtca taataatggt     180
atttgttggg gcaatcaggt atttgttact gtggtagata ccactcgcag tactaatatg     240
ac                                                                    242
```

<210> SEQ ID NO 51
<211> LENGTH: 234
<212> TYPE: DNA
<213> ORGANISM: Artificial Sequence
<220> FEATURE:
<223> OTHER INFORMATION: template

<400> SEQUENCE: 51

```
aactcaacgc ttagtttggg cctgtgttgg tttagaggta ggtcgcgggc agccattagg      60
tgtaggtatt agtggtcatc cattattaaa taaatttgat gacactgaaa actctaatag     120
atatgccggt ggtcctggca ctgataatag ggaatgtata tcaatggatt ataaacaaac     180
acaactgtgt ttacttggtt gcaaaccacc tattggagag cattggggta aagg           234
```

<210> SEQ ID NO 52
<211> LENGTH: 323
<212> TYPE: DNA
<213> ORGANISM: Artificial Sequence
<220> FEATURE:
<223> OTHER INFORMATION: template

<400> SEQUENCE: 52

```
gccactgtac aaagcagtgc tttttttcct actcctagtg gttctatggt aacctcagaa      60
tcccaattat ttaataaacc gtactggtta caacgtgcgc agggccacaa taatggcata     120
tgttggggca atcagttgtt tgtcacagtt gtggatacca ctcgtagcac taacatgact     180
ttatgtgctg aggttaaaaa ggaaagcaca tataaaaatg aaaattttaa ggaatacctt     240
cgtcatggcg aggaatttga tttacaattt atttttcaat tgtgcaaaat tacattaaca     300
gctgatgtta tgacatacat tca                                             323
```

<210> SEQ ID NO 53
<211> LENGTH: 296
<212> TYPE: DNA
<213> ORGANISM: Artificial Sequence
<220> FEATURE:
<223> OTHER INFORMATION: template

<400> SEQUENCE: 53

```
gtatatgttg ctacgcctag tgggtctatg attacgtctg aggcacagtt atttaataaa      60
ccttattggt tgcaacgtgc ccaaggccat aataatggca tttgctgggg taatcaatta     120
tttgttactg tagtagatac tactagaagt actaacatga ctattagtac tgctacagaa     180
cagttaagta aatatgatgc acgaaaaatt aatcagtacc ttagacatgt ggaggaatat     240
gaattacaat ttgtttttca attatgcaaa attactttgt ctgcagaggt tatggc         296
```

<210> SEQ ID NO 54
<211> LENGTH: 236
<212> TYPE: DNA
<213> ORGANISM: Artificial Sequence
<220> FEATURE:

```
<223> OTHER INFORMATION: template

<400> SEQUENCE: 54
ccagataaca cagtatatga tcctaactct caacgcttgg tctgggcctg tgtaggtgtt      60
gaaatcggtc ggggccaacc tttaggggta ggactcagtg gtcatccatt atataataaa     120
ttggatgaca ctgaaaactc tcatgtagca tctgctgttg ataccaaaga tacacgtgat     180
aatgtatctg tggattataa acaaactcag ctgtgtatta ttggctgtgt acctgc         236

<210> SEQ ID NO 55
<211> LENGTH: 225
<212> TYPE: DNA
<213> ORGANISM: Artificial Sequence
<220> FEATURE:
<223> OTHER INFORMATION: template

<400> SEQUENCE: 55
gaaacacaac gtttggtttg ggcatgtgta ggtatggaaa ttggtcgtgg gcagccttta      60
ggtattggcc taagtggcca tccattttat aataaattgg atgatacaga aagtgctcat     120
gcagctacag ctgttattac gcaggatgtt agggataatg tgtcagttga ttataagcaa     180
acacagctgt gtatttttagg ttgtgtacct gctattggtg agcac                    225

<210> SEQ ID NO 56
<211> LENGTH: 307
<212> TYPE: DNA
<213> ORGANISM: Artificial Sequence
<220> FEATURE:
<223> OTHER INFORMATION: template

<400> SEQUENCE: 56
gttctgtata ctgcccctct cccagcggtt ccatggtaac ctctgattcc cagttattta      60
ataagcctta ttggctacat aaggcccagg gccacaacaa tggtatatgt tggcataatc     120
aattatttct tactgttgtg gacactaccc gtagtaccaa cttttacatta tctacctcta    180 tagagtcttc catacctttct acatatgatc cttctaagtt taaggaatat accaggcacg    240
tggaggagta tgatttacaa tttatatttc aactgtgtac tgtcacatta acaactgatg    300
ttatgtc                                                              307

<210> SEQ ID NO 57
<211> LENGTH: 214
<212> TYPE: DNA
<213> ORGANISM: Artificial Sequence
<220> FEATURE:
<223> OTHER INFORMATION: template

<400> SEQUENCE: 57
gacgtgagca gatgtttgtt agacactttt ttaatagggc tggaaaactt ggcgaggctg      60
tcccggatga cctttatatt aaagggtccg gtaatactgc agttatccaa agtagtgcat     120
tttttccaac tcctagtggc tctatagtta cctcagaatc acaattattt aataagcctt     180
attggctaca gcgtgcacaa ggtcataaca atgg                                 214
```